(12) United States Patent
Maruoka et al.

(10) Patent No.: US 8,614,316 B2
(45) Date of Patent: Dec. 24, 2013

(54) OPTICALLY ACTIVE QUATERNARY AMMONIUM SALT HAVING AXIAL ASYMMETRY AND PROCESS FOR PRODUCING α-AMINO ACID AND DERIVATIVE THEREOF WITH THE SAME

(75) Inventors: Keiji Maruoka, Kyoto (JP); Yukifumi Nishimoto, Kobe (JP); Kenichiro Yamamoto, Kobe (JP)

(73) Assignee: Nagase & Co., Ltd., Osaka-shi (JP)

( * ) Notice: Subject to any disclaimer, the term of this patent is extended or adjusted under 35 U.S.C. 154(b) by 652 days.

(21) Appl. No.: 11/910,364

(22) PCT Filed: Mar. 24, 2006

(86) PCT No.: PCT/JP2006/306791
§ 371 (c)(1),
(2), (4) Date: Oct. 1, 2007

(87) PCT Pub. No.: WO2006/104226
PCT Pub. Date: Oct. 5, 2006

(65) Prior Publication Data
US 2009/0270614 A1    Oct. 29, 2009

(30) Foreign Application Priority Data
Mar. 29, 2005   (JP) .................. 2005-094873

(51) Int. Cl.
*C07D 223/18* (2006.01)
(52) U.S. Cl.
USPC .......................................................... 540/587
(58) Field of Classification Search
USPC .......................................................... 540/587
See application file for complete search history.

(56) References Cited

U.S. PATENT DOCUMENTS

| | | | |
|---|---|---|---|
| 6,340,753 B1 | 1/2002 | Maruoka | |
| 2002/0065414 A1 | 5/2002 | Maruoka | |
| 2006/0183896 A1 | 8/2006 | Maruoka | |
| 2007/0135654 A1 | 6/2007 | Maruoka | |
| 2007/0161624 A1 | 7/2007 | Maruoka | |
| 2009/0054679 A1 | 2/2009 | Maruoka et al. | |
| 2010/0029935 A1 | 2/2010 | Maruoka et al. | |

FOREIGN PATENT DOCUMENTS

| | | |
|---|---|---|
| EP | 1 854 796 A1 | 11/2007 |
| EP | 1 870 403 A1 | 12/2007 |
| JP | 2001-48866 | 2/2001 |
| JP | 2002-173492 | 6/2002 |
| JP | 2002 326992 | 11/2002 |
| JP | 2002-326992 | 11/2002 |
| JP | 2003-081976 | 3/2003 |
| JP | 2004-189696 | 7/2004 |
| JP | 2004-238362 | 8/2004 |
| JP | 2004-359578 | 12/2004 |
| JP | 2004 359578 | 12/2004 |
| JP | 2005-41791 | 2/2005 |
| WO | WO 2006/054366 A | 5/2006 |
| WO | 2006 093269 | 9/2006 |

OTHER PUBLICATIONS

U.S. Appl. No. 12/443,588, filed Mar. 30, 2009, Maruoka, et al.
Takashi Ooi, et al., "Design of N-Spiro $C_2$-Symmetric Chiral Quaternary Ammonium Bromides as Novel Chiral Phase-Transfer Catalysts: Synthesis and Application to Practical Asymmetric Synthesis of α-Amino Acids", J. Am. Chem. Soc., 2003, vol. 125, pp. 5139-5151.
Andrew P. Abbott, et al., "Electrochemical recognition of analytes using quaternary ammonium binaphthyl salts", Analyst, vol. 128, No. 3, XP-002532001, 2003, pp. 245-248 (Abstract only).
Hall, et al., "JCSOA9", Journal of the Chemical Society, XP-002532004, 1955, pp. 1242-1247 (Abstract only).
Ooi, et al., "A new N-Spiro $C_2$-Symmetric Chiral Quaternary Ammonium Bromide Consisting of 4,6-Disubstituted Biphenyl Subunit as an Efficient Chiral Phase-Transfer Catalyst", Synlett, No. 12, pp. 1931-1933, 2003.
Kashiwada, et al., "New Hexahydroxybiphenyl Derivatives as Inhibitors of Protein Kinase C", Journal of Medical Chemistry, vol. 37, No. 1, pp. 195-200, 1994.
Insole, "Steric Effects of Methoxy-groups in 2,2'-Bridged Biphenyls. Part II [1]", Journal of the Chemi Society, Perkin Transactions II : Physical organic Chemistry, No. 9, pp. 1168-1173, 1972.
Beaven, et al., Relation between configuration and conjugation in diphenyl derivatives. I. The enantiomorphism and ultraviolet absorption spectra of some 2,2' bridged compounds., Journal of the Chemical society, vol. 46, pp. 854-868, 1952.
Fitts, et al., "Configurational studies in the biphenyl series. IV. Conformation and optical rotation of restricted biphenyls. Configurational correlation of biaryls by optical displacement. The absolute configuration of restricted 1,1'-binaphthyles", Journal of the American Chemical Society, Chemical Abstract 52:55790, vol. 52, pp. 480-486, 1958.

(Continued)

*Primary Examiner* — Brenda Coleman
(74) *Attorney, Agent, or Firm* — Oblon, Spivak, McClelland, Maier & Neustadt, L.L.P.

(57) ABSTRACT

The present invention provides a chiral phase-transfer catalyst of the following formula (I):

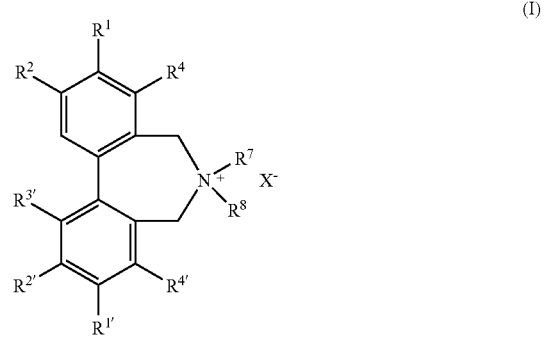

(I)

The compound (I) can be produced by reacting a 2,2'-dimethylene bromide-1,1'-biphenyl derivative, which can be produced through comparatively small number of steps, with an easily available secondary amine.

12 Claims, No Drawings

(56) References Cited

OTHER PUBLICATIONS

Ahmed, et al., "Stric effects in 2,2'-bridged biphenyls with a heterocyclic bridging ring. I. Optically active dihydrodibenzazepines", Journal of the Chemical Society, Chemical abstract 53:2119, pp. 3043-3047, 1958.
Ahmed, et al., "Steric effects in 2,2'- bridged biphenyls with a heterocyclic bridging ring. III. Ultraviolet absorption spectra of some dihydrodibenzazepinium compounds", Journal of the Chemical Society, Chemical Abstract 55: 38083, pp. 4165-4169, 1960.
Lygo, et al., "Identification of a highly effective asymmetric phase-transfer catalyst derived from α- methylnaphthylamine", Tetrahedron Letters, vol. 44, No. 30, pp. 5629-5632, 2003.
Shi, et al., "Synthesis of Axially Dissymmetric Chiral Ammonium Salts by Quaternization of Secondary Amines with (R)-(+)-2,2'-Bis(bromomethyl)-6,6'-dinitrobiphenyl and (R)-(+)-2,2'- Bis (bromomethyl)-1,1'-binaphthyl and an Examination of their Abilities as Chiral Phase-transfer Catalysts", Journal of Chemical Research (S), No. 2, pp. 46-47, 1995.
Ooi, et al., "Molecular Design of a $C_2$-Symmetric Chiral Phase-Transfer Catalyst for Practical Asymmetric Synthesis of α-Amino Acids", Journal of American Chemical Society, vol. 121, No. 27, pp. 6519-6520, 1999.
Han, et al., "Convenient preparation of highly active phase-transfer catalyst or catalytic asymmetric synthesis of α alkyl- and α,α-dialkyl-α-amino acids: application to the short asymmetric synthesis of BIRT-377", Tetrahedron Letter, vol. 46, pp. 8555-8558, 2005.
Kilamura, et al., "Powerful Chiral Phase-Transfer Catalysts for the Asymmetric Synthesis of α-Alkyl- and α α,-Dialkyl- α-amino acids", Angew. Chem. Int. Ed., vol. 44, pp. 1549-1551, 2005.
Kano, et al., "Design of new polyamine-based chiral phase-transfe catalysts for the enantioselective synthesis of phenylalanine", Tetrahedron: Asymmetry, vol. 15, pp. 1243-1245, 2004.
Bruno Bellier, et al., "Synthesis and Biological Properties of New Constrained CCK-B Antagonists: Discrimination of Two Affinity States of the CCK-B Receptor on Transfected Cho Cells", J. Med. Chem., vol. 40, 1997, pp. 3947-3956.
Eric Mossel, et al., "Aspartame Dipeptide Analogues: Effect of Number of Side-Chain Methylene Group Spacers and $C^\alpha$-Methylation in the Second Position", Tetrahedron Asymmetry, vol. 8, No. 8, 1997, pp. 1305-1314.
Takayuki Shioiri, et al., "Asymmetric Phase Transfer Catalysis", Stimulating Concepts in Chemistry, 2000, pp. 123-143.
Martin J. O'Donnell, "The Preparation of Optically Active $_\alpha$-Amino Acids From the Benzophenone Imines of Glycine Derivatives", Aldrichimica Acta, vol. 34, No. 1, 2001, pp. 3-15.
Takashi Ooi, et al., "Practical Catalytic Enantioselective Synthesis of α,α-Dialkyl-α-Amino Acids by Chiral Phase-Transfer Catalysis", Journal of the American Chemical Society, vol. 122, 2000, pp. 5228 and 5229.
Otto Th. Schmidt, et al., "Optisch Aktive 2, 3, 4, 2', 3', 4'-Hexamethoxy-Diphenyldicarbonsaure-6, 6' XIII. Mitteilung Über Natürliche Gerbstoffe", Ann Chem. vol. 576, No. 85, Feb. 18, 1952, pp. 85-93.
J. D. Reitze, et al., "The Further Chemistry of Ellagic Acid I. Synthesis of Tetramethylellagic Acid and Associated Polymer Precursors", Holzforschung, vol. 55, No. 2, 2001, pp. 171-175.
Andrew P. Abbott, et al., "Electrochemical recognition of charged species using quaternary ammonium binaphthyl salts", Analyst, vol. 126, 2001, 1892-1896.
Fréderic Cottineau, et al., "Reductive Cleavage of Axially Disymmetric Tertiary Amines and Quaternary Ammonium Salts by Lithium Aluminium Hydride. Synthesis of New 1,1'-Binaphthyl Substituted Amines", Tetrahedron Letters, vol. 26, No. 4, 1985, pp. 421-424.
Lorenzo Di Bari, et al., "Conformational Study of 2,2'-Homosubstituted 1,1'-Binaphthyls by Means of UV and CD Spectroscopy", J. Am. Chem. Soc., vol. 121, 1999, pp. 7998-8004.
Masaya Ikunaka, et al., "A Scalable Synthesis of (R)-3,5-Dihydro-4H-dinaphth[2,1-c:1'2'-e]azepine", Organic Process Research & Development, vol. 7, 2003, pp. 644-648.
S. F. Mason, et al., "Optical Activity in the Biaryl Series", Tetrahedron, vol. 30, 1974, pp. 1671-1682.

Takashi Ooi, et al., "New, Improved Procedure for the Synthesis of Structurally Diverse N-Spiro $C_2$-Symmetric Chiral Quaternary Ammonium Bromides", J. Org. Chem., vol. 68, 2003, pp. 4576-4578.
Masahiko Seki, et al., "A Practical Synthesis of $C_2$-Symmetric Chiral Binaphthyl Ketone Catalyst", Synthesis, No. 12, 2000, pp. 1677-1680.
Irena G. Stará, et al., "Nucleophilic Cleavage of 4,5-Dihydro-3H-dinaphth[2,1-c:1',2'-e]azepinium Quaternary Salts. A Convenient Approach to New Axially Dissymmetric and Axially Asymmetric Ligands", J. Org. Chem., vol. 57, 1992, pp. 6966-6969.
Irena G. Stará, et al., "Optically Pure (S)- and (R)-4,5-Dihydro-3H-4-Methyldinaphth[2,1-c;1',2'-e]Azepines. Application to the Synthesis of new Bidentate Ligands with Axial Asymmetry", Tetrahedron: Asymmetry, vol. 3, No. 11, 1992, pp. 1365-1368.
Irena G. Stará, et al., "Stereochemical Dichotomy in the Stevens Rearrangement of Axially Twisted Dihydroazepinium and Dihydrothiepinium Salts. A Novel Enantioselective Synthesis of Pentahelicene", J. Am. Chem. Soc., vol. 116, 1994, pp. 5084-5088.
Irena G. Stará, et al., "Nucleophilic Attack on 4,5-Dihydro-4-alkyl-3H-dinaphtho[2,1-c:1',2'-e]thiepinium Salts. A Convenient Approach to New 2,2'-Bidentate 1,1'-Binaphthalene Ligands with Sulfur Donor Atoms", J. Org. Chem., vol. 59, 1994, pp. 1326-1332.
A.M. Costero, et al., "Sistemas Macrociclicos Derivados De Bifenilos Sustituidos", Anales de Quimica, vol. 89, 1993, pp. 95-98 (with English Abstract).
Yong-Gang Wang, et al., "Convenient preparation of chiral phase-transfer catalysts with conformationally fixed biphenyl core for catalytic asymmetric synthesis of α-alkyl- and α,α-dialkyl-α-amino acids: application to the short asymmetric synthesis of BIRT-377", Tetrahedron, vol. 63, 2007, pp. 6042-6050 (with an additional page).
Yong-Gang Wang, et al., "Design of Chiral Phase Transfer Catalyst with Conformationally Fixed Biphenyl Core: Application to Asymmetric Alkylation of Glycine Derivatives", Organic Process Research & Development, vol. 11, 2007, pp. 628-632 (with an additional page).
Yuri N. Belokon, et al., "Copper(II)salen catalysed, asymmetric synthesis of α,α-disubstituted amino acids", Tetrahedron, vol. 60, 2004, 1849-1861.
Jin-Tai Chen, et al., "Synthesis of D-Phenylalanine Using Chiral Phase-Transfer Catalyst", Youji Huaxue, vol. 8, 1988, pp. 164-166 (with English Abstract and an additional page).
Keiji Maruoka, et al., "Enantioselective Amino Acid Synthesis by Chiral Phase-Transfer Catalysis", Chem. Rev., vol. 103, 2003, pp. 3013-3028.
P. Bey, et al., "Synthesis of α-Alkyl and α-Functionalized Methyl-α-Amino Acids", Tetrahedron Letters, No. 17, 1977, pp. 1455-1458.
Martin J. O'Donnell, et al., "The Stereoselective Synthesis of α-Amino Acids by Phase-Transfer Catalysis", J. Am. Chem. Soc., vol. 111, 1989, pp. 2353-2355.
Hyeung-geun Park, et al., "Highly Enantioselective Phase-Transfer Catalytic Alkylation in the Preparation of Non-natural α-Amino Acids via Solid Phase Synthesis Using Aldimine Linker", J. Org. Chem., vol. 70, 2005, pp. 1904-1906.
Yuichiro Arimura, et al., "Highly Enantioselective Monoalkylation of Aldimine Schiff Base of Glycine Ester by Designer Chiral Phase-Transfer Catalysts", The Chemical Society of Japan, Dai 86 Shunki Nenkai (2006), Koen Yokoshu II, 2 H5-44, Mar. 13, 2006, p. 1073 (with partial English Translation).
Otto Th. Schmidt, et al., "Optisch Aktive 2, 3, 4, 2', 3', 4'-Hexamethoxy-Diphenyldicarbonsaure-6, 6' XIII. Mitteilung Über Natürliche Gerbstoffe", Ann Chem. vol. 576, No. 85, Feb. 18, 1952, pp. 85-93 (English translation of p. 87, line 14 to end of p. 89).
Theodora W. Greene, "Protective Groups in Organic Synthesis", John Wiley & Sons, 1981, pp. 168-169.
Office Action mailed Nov. 5, 2012, in co-pending U.S. Appl. No. 13/338,301.
Frank R. Hewgill, et al., "Phenanthrene-4,5-quinones: a Synthesis of Morphenol", J. Chem. Soc. Perkin Trans. I, Issue 6, Jan. 1988, pp. 1305-1311.
U.S. Appl. No. 13/338,301, filed Dec. 28, 2011, Maruoka, et al.
U.S. Appl. No. 13/338,313, filed Dec. 28, 2011, Maruoka, et al.
U.S. Appl. No. 13/338,601, filed Dec. 28, 2011, Maruoka, et al.
U.S. Appl. No. 13/338,659, filed Dec. 28, 2011, Maruoka, et al.
U.S. Appl. No. 13/337,658, filed Dec. 27, 2011, Maruoka, et al.
U.S. Appl. No. 13/039,645, filed Mar. 3, 2011, Maruoka.

US 8,614,316 B2

OPTICALLY ACTIVE QUATERNARY AMMONIUM SALT HAVING AXIAL ASYMMETRY AND PROCESS FOR PRODUCING α-AMINO ACID AND DERIVATIVE THEREOF WITH THE SAME

CROSS-REFERENCE TO RELATED APPLICATIONS

This application is a 371 of PCT/JP2006/306791 filed Mar. 24, 2006 and claims the benefit of JP 2005-094873 filed Mar. 29, 2005.

TECHNICAL FIELD

The present invention relates to optically active quaternary ammonium salts having axial asymmetry and methods for producing the same. The present invention further relates to methods for producing optically active α-amino acids and derivatives thereof by using this optically active quaternary ammonium salt having axial asymmetry as a phase-transfer catalyst.

BACKGROUND ART

α-Alkyl-α-amino acids represented by the formula $H_2NCH(R)COOH$ are very important naturally-occurring α-amino acids. α-Alkyl-α-amino acids in which the α-carbon has the L-configuration are a structural component of proteins (polypeptide chains) that exist in animals, plants, and microorganisms, for example. The D-form of α-alkyl-α-amino acids exists in plants, fungi and microorganisms as a structural component of non-proteogenic compounds. On the other hand, α,α-dialkyl-α-amino acids are recently gaining attention because of their unique functions, including the fact that they are stereochemically stable and that when they are incorporated into peptides, those peptides are not susceptible to enzymatic hydrolysis by proteases (see Bellier, B. et al. (1997). *J. Med. Chem.* 40:3947 and Mossel, E. et al. (1997). *Tetrahedron Asymmetry* 8:1305). These properties have led α,α-dialkyl-α-amino acids to be considered for use as chiral building blocks for the synthesis of peptides having enhanced activity, effective enzyme inhibitors, and compounds having other biological activities. Methods for synthesizing non-proteogenic α-amino acids, particularly α,α-dialkyl-α-amino acids, by selectively building the stereochemistry of the α-carbon have been investigated, but at the present time, a practical method has not yet been found.

Chiral phase-transfer catalysts allow stereoselective alkylation of glycine derivatives and are easy to use and can be applied widely, and thus have become increasingly important in the field of process chemistry. A large number of researches into designing phase-transfer catalysts have been conducted mainly by using cinchona alkaloid derivatives, and to date several useful methods have been reported (e.g., see Shioiri, T. et al., Stimulating Concepts in Chemistry, edited by Vogtle, F. et al., WILEY-VCH: Weinheim, p. 123, 2000; and O'Donnell, M. J. (2001). *Aldrichimica Acta*, 34:3). However, when such phase-transfer catalysts are used, various problems are caused, including the fact that halogen-based solvents are employed, the reaction is sluggish, and low temperature conditions are required. In particular, the use of chiral phase-transfer catalysts derived from such cinchona alkaloids is not particularly efficient in the synthesis of α,α-dialkyl-α-amino acids.

The present inventors have prepared an optically active quaternary ammonium salt having axial asymmetry, and have clearly shown that it can be used as a phase-transfer catalyst for stereoselectively synthesizing α-alkyl-α-amino acids and α,α-dialkyl-α-amino acids (see Japanese Laid-Open Patent Publication No. 2001-48866; Japanese Laid-Open Patent Publication No. 2003-81976; and Ooi, T. et al. (2000). *J. Am. Chem. Soc.* 122:5228). For example, a spiro-compound represented by the following formula is very effective for stereoselectively producing α,α-dialkyl-α-amino acids because it catalyzes the stereoselective double alkylation of glycine derivatives and the stereoselective monoalkylation α-alkyl-α-amino acid derivatives:

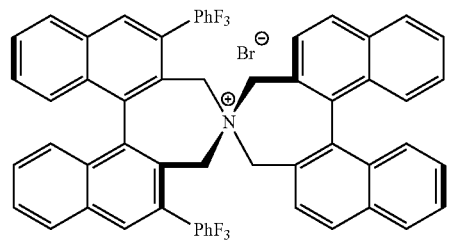

(where $PhF_3$ represents a 3,4,5-trifluorophenyl group). However, the preparation of such spiro-type catalysts requires many steps, and for example, if chiral binaphthol, which is easily available, is used as the starting raw material, then eleven process steps are required just to prepare the left half of this catalyst structure. Therefore, drawbacks of conventional optically active quaternary ammonium salts having axial asymmetry are extremely time-consuming and costly nature of their preparation.

DISCLOSURE OF INVENTION

It is an object of the present invention to provide a chiral phase-transfer catalyst that has a simple structure and that can be produced in a fewer number of steps.

The present invention provides a compound represented by the following formula (I):

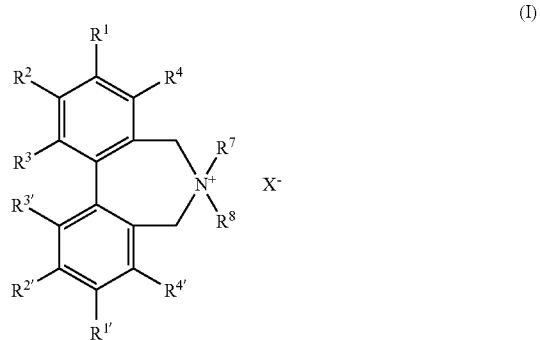

wherein
$R^1$, $R^{1'}$, $R^2$, and $R^{2'}$ are each independently:
    a hydrogen atom;
    a halogen atom;
    a $C_1$ to $C_5$ alkyl group that may be substituted with a halogen atom and/or an aryl group, and/or that may be branched or form a cyclic group; or
    a $C_1$ to $C_5$ alkoxy group that may be substituted with a halogen atom and/or an aryl group, and/or that may be branched or form a cyclic group;

$R^3$ and $R^{3'}$ are each independently:
  a halogen atom;
  a $C_1$ to $C_5$ alkyl group that may be substituted with a halogen atom and/or an aryl group, and/or that may be branched or form a cyclic group; or
  a $C_1$ to $C_5$ alkoxy group that may be substituted with a halogen atom and/or an aryl group, and/or that may be branched or form a cyclic group;

$R^4$ and $R^{4'}$ are groups independently selected from the group consisting of:
  (i) a hydrogen atom;
  (ii) —$NR^{30}R^{31}$ (where $R^{30}$ and $R^{31}$ are each independently a hydrogen atom or a $C_1$ to $C_4$ alkyl group that may be substituted with a halogen atom);
  (iii) a cyano group;
  (iv) a nitro group;
  (v) a carbamoyl group;
  (vi) an N—($C_1$ to $C_4$ alkyl)carbamoyl group;
  (vii) an N,N-di($C_1$ to $C_4$ alkyl)carbamoyl group;
  (viii) —$NHCOR^9$ (where $R^9$ is a $C_1$ to $C_4$ alkyl group that may be branched and that may be substituted with a halogen atom);
  (ix) a halogen atom;
  (x) a $C_1$ to $C_6$ alkyl group that may be branched or form a cyclic group and that may be substituted with a halogen atom;
  (xi) a $C_2$ to $C_6$ alkenyl group that may be branched or form a cyclic group and that may be substituted with a halogen atom;
  (xii) a $C_2$ to $C_6$ alkynyl group that may be branched or form a cyclic group and that may be substituted with a halogen atom;
  (xiii) an aralkyl group, wherein the aryl moiety of the aralkyl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  (xiv) a heteroaralkyl group having a heteroaryl moiety, wherein the heteroaryl moiety may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  (xv) an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
    or may be substituted with —O—$(CH_2)_p$—O— (where p is 1 or 2) at positions 3 and 4 that are taken together;
  (xvi) a heteroaryl group, wherein the heteroaryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom)
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(xvii) —S(O)$_n$—R (where n is 0, 1, or 2, and R is a C$_1$ to C$_4$ alkyl group that may be branched and that may be substituted with a halogen atom);
R$^7$ and R$^8$ are groups independently selected from the group consisting of:
(i) a C$_1$ to C$_{30}$ alkyl group that may be branched or form a cyclic group and that may be substituted with a halogen atom;
(ii) a C$_2$ to C$_{12}$ alkenyl group that may be branched or form a cyclic group and that may be substituted with a halogen atom;
(iii) a C$_2$ to C$_{12}$ alkynyl group that may be branched or form a cyclic group and that may be substituted with a halogen atom;
(iv) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
(v) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
(vi) —(CH$_2$)$_n$OCONR$^{10}$R$^{11}$ (where R$^{10}$ and R$^{11'}$ are groups independently selected from the group consisting of:
(1) a hydrogen atom;
(2) a C$_1$ to C$_4$ alkyl group that may be branched and that may be substituted with a halogen atom;
(3) a C$_2$ to C$_6$ alkenyl group that may be branched or form a cyclic group and that may be substituted with a halogen atom;
(4) a C$_2$ to C$_6$ alkynyl group that may be branched or form a cyclic group and that may be substituted with a halogen atom;
(5) an aralkyl group, wherein the aryl moiety of the aralkyl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
(6) a heteroaralkyl group having a heteroaryl moiety, wherein the heteroaryl moiety may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom, an aryl group that may be substituted with a halogen atom,
a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom;
(7) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom; and
(8) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom;
and n is an integer from 1 to 12);
(vii) —$(CH_2)_n CONR^{12}R^{13}$ (where $R^{12}$ and $R^{13}$ are groups independently selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom; and
(4) a heteroaryl group, wherein the heteroaryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);
(viii) —(CH$_2$)$_n$NR$^{12}$COR$^{13}$ (where R$^{12}$ and R$^{13}$ are groups independently selected from the group consisting of:
  (1) a hydrogen atom;
  (2) a C$_1$ to C$_4$ alkyl group that may be branched and that may be substituted with a halogen atom;
  (3) an aryl group, wherein the aryl group may be substituted with at least one group selected from the group consisting of:
  a C$_1$ to C$_4$ alkyl group that may be branched and that may be substituted with a halogen atom,
  a C$_1$ to C$_5$ alkoxy group that may be branched and that may be substituted with a halogen atom,
  an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
  a cyano group,
  —NR$^{30}$R$^{31}$ (where R$^{30}$ and R$^{31}$ are each independently a hydrogen atom or a C$_1$ to C$_4$ alkyl group that may be substituted with a halogen atom),
  a nitro group,
  a carbamoyl group,
  an N—(C$_1$ to C$_4$ alkyl)carbamoyl group,
  an N,N-di(C$_1$ to C$_4$ alkyl)carbamoyl group,
  —NHCOR$^9$ (where R$^9$ is a C$_1$ to C$_4$ alkyl group that may be branched and that may be substituted with a halogen atom), and
  a halogen atom; and
  (4) a heteroaryl group, wherein the heteroaryl group may be substituted with at least one group selected from the group consisting of:
  a C$_1$ to C$_4$ alkyl group that may be branched and that may be substituted with a halogen atom,
  a C$_1$ to C$_5$ alkoxy group that may be branched and that may be substituted with a halogen atom,
  an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);
(ix) —(CH$_2$)$_n$NR$^{12}$R$^{13}$ (where R$^{12}$ and R$^{13}$ are groups independently selected from the group consisting of:
  (1) a hydrogen atom;
  (2) a C$_1$ to C$_4$ alkyl group that may be branched and that may be substituted with a halogen atom;
  (3) an aryl group, wherein the aryl group may be substituted with at least one group selected from the group consisting of:
  a C$_1$ to C$_4$ alkyl group that may be branched and that may be substituted with a halogen atom,
  a C$_1$ to C$_5$ alkoxy group that may be branched and that may be substituted with a halogen atom,
  an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
  a cyano group,
  —NR$^{30}$R$^{31}$ (where R$^{30}$ and R$^{31}$ are each independently a hydrogen atom or a C$_1$ to C$_4$ alkyl group that may be substituted with a halogen atom),
  a nitro group,
  a carbamoyl group,
  an N—(C$_1$ to C$_4$ alkyl)carbamoyl group,
  an N,N-di(C$_1$ to C$_4$ alkyl)carbamoyl group,
  —NHCOR$^9$ (where R$^9$ is a C$_1$ to C$_4$ alkyl group that may be branched and that may be substituted with a halogen atom), and
  a halogen atom; and
  (4) a heteroaryl group, wherein the heteroaryl group may be substituted with at least one group selected from the group consisting of:
  a C$_1$ to C$_4$ alkyl group that may be branched and that may be substituted with a halogen atom,
  a C$_1$ to C$_5$ alkoxy group that may be branched and that may be substituted with a halogen atom,
  an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);

(x) —(CH$_2$)$_n$Y—OR$^{12}$ (where Y is a C$_1$ to C$_4$ divalent saturated hydrocarbon group that may be branched and that may be substituted with a halogen atom, and R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);

(xi) —(CH$_2$)$_n$—OR$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);

(xii) —(CH$_2$)$_n$—S—R$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);

(xiii) —(CH$_2$)$_n$—SO—R$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12); and
(xiv) —(CH$_2$)$_n$—SO$_2$—R$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12); or
R$^7$ and R$^8$ are taken together to form a divalent group selected from the group consisting of:
—(CH$_2$)$_m$— (where m is an integer from 2 to 8);

[chemical structures]

(wherein R$^{20}$, R$^{21}$, R$^{22}$, R$^{23}$, R$^{24}$, R$^{25}$, R$^{26}$, R$^{27}$, R$^{28}$, R$^{29}$, R$^{41}$, and R$^{42}$ are groups independently selected from the group consisting of:
a hydrogen atom;
a C$_1$ to C$_8$ alkyl group that may be branched or form a cyclic group, and/or that may be substituted with a halogen atom;
a C$_2$ to C$_8$ alkenyl group that may be branched or form a cyclic group, and/or that may be substituted with a halogen atom;
a C$_2$ to C$_8$ alkynyl group that may be branched or form a cyclic group, and/or that may be substituted with a halogen atom;
an aryl group, which may be substituted with a C$_1$ to C$_4$ alkyl group that may be substituted with a halogen atom, a C$_1$ to C$_3$ alkoxy group that may be substituted with a halogen atom, an aryl group that may be substituted with a C$_1$ to C$_4$ alkyl group that may be substituted with a halogen atom, a cyano group, a halogen atom, a nitro group, —NR$^{30}$R$^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaryl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaralkyl group, which has a hetroaryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a ($C_1$ to $C_3$ alkoxy)carbonyl group;
a carbamoyl group;
an N—($C_1$ to $C_4$ alkyl)carbamoyl group; and
an N,N-di($C_1$ to $C_4$ alkyl)carbamoyl group (where the $C_1$ to $C_4$ alkyl groups may be the same or different)); and
$X^-$ is an anion selected from the group consisting of a halide anion, $SCN^-$, $HSO_4^-$, $HF_2^-$, $CF_3SO_3^-$, $CH_3$-Ph-$SO_3^-$, and $CH_3SO_3^-$.

In one embodiment, each of $R^1$, $R^{1'}$, $R^2$, $R^{2'}$, $R^3$, and $R^{3'}$ of the compound represented by the formula (I) is a $C_1$ to $C_5$ alkoxy group that may be branched or form a cyclic group and that may be substituted with a halogen atom.

In one embodiment, each of $R^1$, $R^{1'}$, $R^2$, $R^{2'}$, $R^3$, and $R^{3'}$ of the compound represented by the formula (I) is a methoxy group, an ethoxy group, or a benzyloxy group.

In one embodiment, $R^4$ and $R^{4'}$ of the compound represented by the formula (I) are groups independently selected from the group consisting of:
a hydrogen atom; and
an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom.

In a further embodiment, each of $R^4$ and $R^{4'}$ of the compound represented by the formula (I) is a 3,4,5-trifluorophenyl group or a 3,5-bis(trifluoromethyl)phenyl group.

In one embodiment, $R^7$ and $R^8$ of the compound represented by the formula (I) are each independently a $C_1$ to $C_{30}$ alkyl group that may be branched or form a cyclic group and that may be substituted with a halogen atom.

In a further embodiment, $R^7$ and $R^8$ of the compound represented by the formula (I) are both n-butyl groups.

The present invention also provides a method for producing the compound represented by the formula (I) described above, comprising:

a step of reacting a compound represented by the following formula (II):

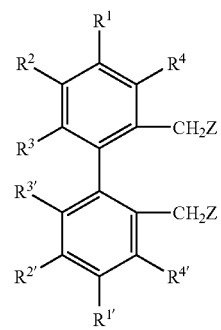

(II)

with a secondary amine represented by the following formula (III):

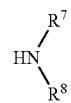

(III)

in an organic solvent in the presence of an acid-scavenging agent;
wherein in the formula (II):
$R^1$, $R^{1'}$, $R^2$, and $R^{2'}$ are each independently:
a hydrogen atom;
a $C_1$ to $C_5$ alkyl group that may be substituted with a halogen atom and/or an aryl group, and/or that may be branched or form a cyclic group; or
a $C_1$ to $C_5$ alkoxy group that may be substituted with a halogen atom and/or an aryl group, and/or that may be branched or form a cyclic group;

$R^3$ and $R^{3'}$ are each independently:
  a halogen atom;
  a $C_1$ to $C_5$ alkyl group that may be substituted with a halogen atom and/or an aryl group, and/or that may be branched or form a cyclic group; or
  a $C_1$ to $C_5$ alkoxy group that may be substituted with a halogen atom and/or an aryl group, and/or that may be branched or form a cyclic group;

$R^4$ and $R^{4'}$ are each independently:
  (i) a hydrogen atom;
  (ii) —$NR^{30}R^{31}$ (where $R^{30}$ and $R^{31}$ are each independently a hydrogen atom or a $C_1$ to $C_4$ alkyl group than may be substituted with a halogen atom);
  (iii) a cyano group;
  (iv) a nitro group;
  (v) a carbamoyl group;
  (vi) an N—($C_1$ to $C_4$ alkyl)carbamoyl group;
  (vii) an N,N-di($C_1$ to $C_4$ alkyl)carbamoyl group;
  (viii) —$NHCOR^9$ (where $R^9$ is a $C_1$ to $C_4$ alkyl group that may be branched and that may be substituted with a halogen atom);
  (ix) a halogen atom;
  (x) a $C_1$ to $C_6$ alkyl group that may be branched or form a cyclic group and that may be substituted with a halogen atom;
  (xi) a $C_2$ to $C_6$ alkenyl group that may be branched or form a cyclic group and that may be substituted with a halogen atom;
  (xii) a $C_2$ to $C_6$ alkynyl group that may be branched or form a cyclic group and that may be substituted with a halogen atom;
  (xiii) an aralkyl group, wherein the aryl moiety of the aralkyl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  (xiv) a heteroaralkyl group having a heteroaryl moiety, wherein the heteroaryl moiety may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  (xv) an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  or may be substituted with —O—$(CH_2)_p$—O— (where p is 1 or 2) at positions 3 and 4 that are taken together;
  (xvi) a heteroaryl group, wherein the heteroaryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(xvii) —S(O)$_n$—R (where n is 0, 1, or 2, and R is a C$_1$ to C$_4$ alkyl group that may be branched); and
Z is a halogen atom;
and in the formula (III):
R$^7$ and R$^8$ are groups independently selected from the group consisting of:
(i) a C$_1$ to C$_{30}$ alkyl group that may be branched or form a cyclic group and that may be substituted with a halogen atom;
(ii) a C$_2$ to C$_{12}$ alkenyl group that may be branched or form a cyclic group and that may be substituted with a halogen atom;
(iii) a C$_2$ to C$_{12}$ alkynyl group that may be branched or form a cyclic group and that may be substituted with a halogen atom;
(iv) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom,
a C$_1$ to C$_4$ alkyl group that may be branched and that may be substituted with a halogen atom, a cyano group, NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
(v) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom,
a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
(vi) —(CH$_2$)$_n$OCONR$^{10}$R$^{11}$ (where R$^{10}$ and R$^{11}$ are groups independently selected from the group consisting of:
(1) a hydrogen atom;
(2) a C$_1$ to C$_4$ alkyl group that may be branched and that may be substituted with a halogen atom;
(3) a C$_2$ to C$_6$ alkenyl group that may be branched or form a cyclic group and that may be substituted with a halogen atom;
(4) a C$_2$ to C$_6$ alkynyl group that may be branched or form a cyclic group and that may be substituted with a halogen atom;
(5) an aralkyl group, wherein the aryl moiety of the aralkyl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom,
a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
(6) a heteroaralkyl group having a heteroaryl moiety, wherein the heteroaryl moiety may be substituted with at least one group selected from the group consisting of:
a C$_1$ to C$_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where $R^9$ is a $C_1$ to $C_4$ alkyl group that may be branched and that may be substituted with a halogen atom), and a halogen atom;

(7) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where $R^9$ is a $C_1$ to $C_4$ alkyl group that may be branched and that may be substituted with a halogen atom), and a halogen atom; and (8) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where $R^9$ is a $C_1$ to $C_4$ alkyl group that may be branched and that may be substituted with a halogen atom), and a halogen atom;

and n is an integer from 1 to 12);

(vii) —$(CH_2)_n CONR^{12}R^{13}$ (where $R^{12}$ and $R^{13}$ are groups independently selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where $R^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom;

and n is an integer from 1 to 12);

(viii) —(CH$_2$)$_n$NR$^{12}$COR$^{13}$ (where R$^{12}$ and R$^{13}$ are groups independently selected from the group consisting of:

(1) a hydrogen atom;

(2) a C$_1$ to C$_4$ alkyl group that may be branched and that may be substituted with a halogen atom;

(3) an aryl group, wherein the aryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom; and (4) a heteroaryl group, wherein the heteroaryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom; and n is an integer from 1 to 12);

(ix) —(CH$_2$)$_n$NR$^{12}$R$^{13}$ (where R$^2$ and R$^{13}$ are groups independently selected from the group consisting of:

(1) a hydrogen atom;

(2) a C$_1$ to C$_4$ alkyl group that may be branched and that may be substituted with a halogen atom;

(3) an aryl group, wherein the aryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom), a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, —NHCOR$^9$ (where R$^9$ is a C$_1$ to C$_4$ alkyl group that may be branched and that may be substituted with a halogen atom), and a halogen atom; and (4) a heteroaryl group, wherein the heteroaryl group may be substituted with at least one group selected from the group consisting of:

a C$_1$ to C$_4$ alkyl group that may be branched and that may be substituted with a halogen atom, a C$_1$ to C$_5$ alkoxy group that may be branched and that may be substituted with a halogen atom, an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);

(x) —(CH$_2$)$_n$Y—OR$^{12}$ (where Y is a C$_1$ to C$_4$ divalent saturated hydrocarbon group that may be branched and that may be substituted with a halogen atom, and R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH-COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH-COR$^9$ (where R$^9$ is a C$_1$ to C$_4$ alkyl group that may be branched and that may be substituted with a halogen atom),
a cyano group,
NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);

(xi) —(CH$_2$)—OR$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH-COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR⁹ (where $R^9$ is a $C_1$ to $C_4$ alkyl group that may be branched and that may be substituted with a halogen atom),
- a cyano group,
- —$NR^{30}R^{31}$ (where $R^{30}$ and $R^{31}$ are each independently a hydrogen atom or a $C_1$ to $C_4$ alkyl group that may be substituted with a halogen atom),
- a nitro group,
- a carbamoyl group,
- an N—($C_1$ to $C_4$ alkyl)carbamoyl group,
- an N,N-di($C_1$ to $C_4$ alkyl)carbamoyl group,
- —$NHCOR^9$ (where $R^9$ is a $C_1$ to $C_4$ alkyl group that may be branched and that may be substituted with a halogen atom), and
- a halogen atom;

and n is an integer from 1 to 12);

(xii) —$(CH_2)_n$—S—$R^{12}$ (where $R^{12}$ is a group selected from the group consisting of:
 (1) a hydrogen atom;
 (2) a $C_1$ to $C_4$ alkyl group that may be branched;
 (3) an aryl group, wherein the aryl group may be substituted with at least one group selected from the group consisting of:
  - a $C_1$ to $C_4$ alkyl group that may be branched and that may be substituted with a halogen atom,
  - a $C_1$ to $C_5$ alkoxy group that may be branched and that may be substituted with a halogen atom,
  - an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
  - a cyano group,
  - $NR^{30}R^{31}$ (where $R^{30}$ and $R^{31}$ are each independently a hydrogen atom or a $C_1$ to $C_4$ alkyl group that may be substituted with a halogen atom),
  - a nitro group,
  - a carbamoyl group,
  - an N—($C_1$ to $C_4$ alkyl)carbamoyl group,
  - an N,N-di($C_1$ to $C_4$ alkyl)carbamoyl group,
  - —$NHCOR^9$ (where $R^9$ is a $C_1$ to $C_4$ alkyl group that may be branched and that may be substituted with a halogen atom), and
  - a halogen atom; and
 (4) a heteroaryl group, wherein the heteroaryl group may be substituted with at least one group selected from the group consisting of:
  - a $C_1$ to $C_4$ alkyl group that may be branched and that may be substituted with a halogen atom,
  - a $C_1$ to $C_5$ alkoxy group that may be branched and that may be substituted with a halogen atom,
  - an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NH-COR⁹ (where $R^9$ is a $C_1$ to $C_4$ alkyl group that may be branched and that may be substituted with a halogen atom),
  - a cyano group,
  - —$NR^{30}R^{31}$ (where $R^{30}$ and $R^{31}$ are each independently a hydrogen atom or a $C_1$ to $C_4$ alkyl group that may be substituted with a halogen atom),
  - a nitro group,
  - a carbamoyl group,
  - an N—($C_1$ to $C_4$ alkyl)carbamoyl group,
  - an N,N-di($C_1$ to $C_4$ alkyl)carbamoyl group,
  - —$NHCOR^9$ (where $R^9$ is a $C_1$ to $C_4$ alkyl group that may be branched and that may be substituted with a halogen atom), and
  - a halogen atom;

and n is an integer from 1 to 12);

(xiii) —$(CH_2)_n$—SO—$R^{12}$ (where $R^{12}$ is a group selected from the group consisting of:
 (1) a hydrogen atom;
 (2) a $C_1$ to $C_4$ alkyl group that may be branched and that may be substituted with a halogen atom;
 (3) an aryl group, wherein the aryl group may be substituted with at least one group selected from the group consisting of:
  - a $C_1$ to $C_4$ alkyl group that may be branched and that may be substituted with a halogen atom,
  - a $C_1$ to $C_5$ alkoxy group that may be branched and that may be substituted with a halogen atom,
  - an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NH-COR⁹ (where $R^9$ is a $C_1$ to $C_4$ alkyl group that may be branched and that may be substituted with a halogen atom),
  - a cyano group,
  - —$NR^{30}R^{31}$ (where $R^{30}$ and $R^{31}$ are each independently a hydrogen atom or a $C_1$ to $C_4$ alkyl group that may be substituted with a halogen atom),
  - a nitro group,
  - a carbamoyl group,
  - an N—($C_1$ to $C_4$ alkyl)carbamoyl group,
  - an N,N-di($C_1$ to $C_4$ alkyl)carbamoyl group,
  - —$NHCOR^9$ (where $R^9$ is a $C_1$ to $C_4$ alkyl group that may be branched and that may be substituted with a halogen atom), and
  - a halogen atom; and
 (4) a heteroaryl group, wherein the heteroaryl group may be substituted with at least one group selected from the group consisting of:
  - a $C_1$ to $C_4$ alkyl group that may be branched and that may be substituted with a halogen atom,
  - a $C_1$ to $C_5$ alkoxy group that may be branched and that may be substituted with a halogen atom,
  - an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12); and
(xiv) —(CH$_2$)$_n$—SO$_2$—R$^{12}$ (where R$^2$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12); or
R$^7$ and R$^8$ are taken together to form a divalent group selected from the group consisting of:
—(CH$_2$)$_m$— (where m is an integer from 2 to 8);

(wherein R$^{20}$, R$^{21}$, R$^{22}$, R$^{23}$, R$^{24}$, R$^{25}$, R$^{26}$, R$^{27}$, R$^{28}$, R$^{29}$, R$^{41}$, and R$^{42}$ are groups independently selected from the group consisting of:
a hydrogen atom;
a C$_1$ to C$_8$ alkyl group that may be branched or form a cyclic group, and/or that may be substituted with a halogen atom;
a C$_2$ to C$_8$ alkenyl group that may be branched or form a cyclic group, and/or that may be substituted with a halogen atom;
a C$_2$ to C$_8$ alkynyl group that may be branched or form a cyclic group, and/or that may be substituted with a halogen atom;
an aryl group, which may be substituted with a C$_1$ to C$_4$ alkyl group that may be substituted with a halogen atom, a C$_1$ to C$_3$ alkoxy group that may be substituted with a halogen atom, an aryl group that may be substituted with a C$_1$ to C$_4$ alkyl group that may be substituted with a halogen atom, a cyano group, a halogen atom, a nitro group, —NR$^{30}$R$^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaryl group, which may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaralkyl group, which has a hetroaryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a ($C_1$ to $C_3$ alkoxy)carbonyl group;
a carbamoyl group;
an N—($C_1$ to $C_4$ alkyl)carbamoyl group; and
an N,N-di($C_1$ to $C_4$ alkyl)carbamoyl group (where the $C_1$ to $C_4$ alkyl groups may be the same or different)).

In one embodiment, each of $R^1$, $R^{1'}$, $R^2$, $R^{2'}$, $R^3$, and $R^{3'}$ of the compound represented by the formula (II) is a $C_1$ to $C_5$ alkoxy group that may be branched or form a cyclic group and that may be substituted with a halogen atom.

In one embodiment, each of $R^1$, $R^{1'}$, $R^2$, $R^{2'}$, $R^3$, and $R^{3'}$ of the compound represented by the formula (II) is a methoxy group, an ethoxy group, or a benzyloxy group.

In one embodiment, $R^4$ and $R^{4'}$ of the compound represented by the formula (II) are groups independently selected from the group consisting of:
a hydrogen atom; and
an aryl group, wherein the aryl group may be substituted with at least one group selected from the group consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—NHCOR$^9$ (where $R^9$ is a $C_1$ to $C_4$ alkyl group that may be branched and that may be substituted with a halogen atom), and
a halogen atom.

In a further embodiment, each of $R^4$ and $R^{4'}$ of the compound represented by the formula (II) is a 3,4,5-trifluorophenyl group or a 3,5-bis(trifluoromethyl)phenyl group.

In one embodiment, $R^7$ and $R^8$ of the compound represented by the formula (III) are each independently a $C_1$ to $C_{30}$ alkyl group that may be branched or form a cyclic group and that may be substituted with a halogen atom.

In a further embodiment, $R^7$ and $R^8$ of the compound represented by the formula (III) are both n-butyl groups.

The present invention also provides a method for stereoselectively producing a compound represented by the formula (VI):

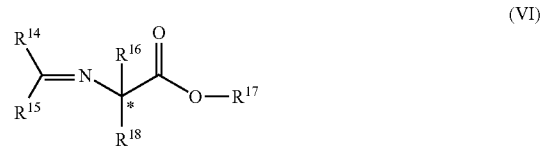

comprising:
a step of alkylating a compound represented by the formula (IV):

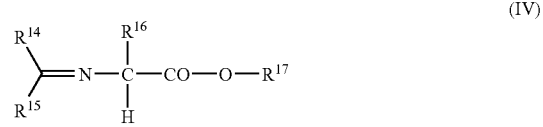

with a compound of the formula (V):

using a compound represented by the formula (I) that is pure with respect to its axial asymmetry as a phase-transfer catalyst:

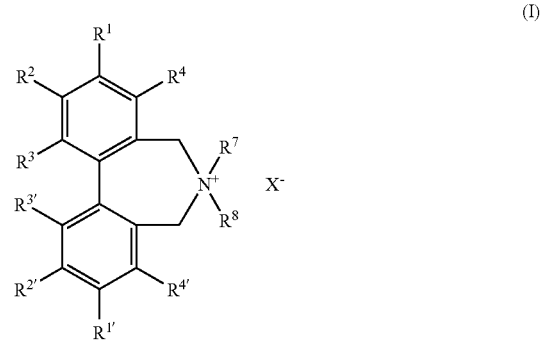

in a medium in the presence of an inorganic base,
wherein in the formula (I), $R^1$, $R^{1'}$, $R^2$, and $R^{2'}$ are each independently:
  a hydrogen atom;
  a halogen atom;
  a $C_1$ to $C_5$ alkyl group that may be substituted with a halogen atom and/or an aryl group, and/or that may be branched or form a cyclic group; or
  a $C_1$ to $C_5$ alkoxy group that may be substituted with a halogen atom and/or an aryl group, and/or that may be branched or form a cyclic group;

$R^3$ and $R^{3'}$ are each independently:
  a halogen atom;
  a $C_1$ to $C_5$ alkyl group that may be substituted with a halogen atom and/or an aryl group, and/or that may be branched or form a cyclic group; or
  a $C_1$ to $C_5$ alkoxy group that may be substituted with a halogen atom and/or an aryl group, and/or that may be branched or form a cyclic group;

$R^4$ and $R^{4'}$ are each independently a group selected from the group consisting of:
  (i) a hydrogen atom;
  (ii) —$NR^{30}R^{31}$ (where $R^{30}$ and $R^{31}$ are each independently a hydrogen atom or a $C_1$ to $C_4$ alkyl group than may be substituted with a halogen atom);
  (iii) a cyano group;
  (iv) a nitro group;
  (v) a carbamoyl group;
  (vi) an N—($C_1$ to $C_4$ alkyl)carbamoyl group;
  (vii) an N,N-di($C_1$ to $C_4$ alkyl)carbamoyl group;
  (viii) —$NHCOR^9$ (where $R^9$ is a $C_1$ to $C_4$ alkyl group that may be branched and that may be substituted with a halogen atom);
  (ix) a halogen atom;
  (x) a $C_1$ to $C_6$ alkyl group that may be branched or form a cyclic group and that may be substituted with a halogen atom;
  (xi) a $C_2$ to $C_6$ alkenyl group that may be branched or form a cyclic group and that may be substituted with a halogen atom;
  (xii) a $C_2$ to $C_6$ alkynyl group that may be branched or form a cyclic group and that may be substituted with a halogen atom;
  (xiii) an aralkyl group, wherein the aryl moiety of the aralkyl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  (xiv) a heteroaralkyl group having a heteroaryl moiety, wherein the heteroaryl moiety may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  (xv) an aryl group, wherein the aryl group may be substituted with at least one group selected from the group consisting of:
    a $C_1$ to $C_4$ alkyl group that may be branched and that may be substituted with a halogen atom,
    a $C_1$ to $C_5$ alkoxy group that may be branched and that may be substituted with a halogen atom,
    an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
    a cyano group,
    —$NR^{30}R^{31}$ (where $R^{30}$ and $R^{31}$ are each independently a hydrogen atom or a $C_1$ to $C_4$ alkyl group that may be substituted with a halogen atom),
    a nitro group,
    a carbamoyl group,
    an N—($C_1$ to $C_4$ alkyl)carbamoyl group,
    an N,N-di($C_1$ to $C_4$ alkyl)carbamoyl group,
    —$NHCOR^9$ (where $R^9$ is a $C_1$ to $C_4$ alkyl group that may be branched and that may be substituted with a halogen atom), and
    a halogen atom;
  or may be substituted with —O—$(CH_2)_p$—O— (where p is 1 or 2) at positions 3 and 4 that are taken together;
  (xvi) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (xvii) —$S(O)_n$—R (where n is 0, 1, or 2, and R is a $C_1$ to $C_4$ alkyl group that may be branched and that may be substituted with a halogen atom);

$R^7$ and $R^8$ are each independently a monovalent organic group or are taken together to form a divalent organic group; and $X^-$ is a halide anion;

in the formula (IV) and formula (VI), $R^{14}$ and $R^{15}$ are each independently a group selected from the group consisting of:

(i) a hydrogen atom; or (ii) an aryl group, wherein the aryl group may be substituted with at least one group selected from the group consisting of:

a $C_1$ to $C_4$ alkyl group that may be branched and that may be substituted with a halogen atom;

a $C_1$ to $C_5$ alkoxy group that may be branched and that may be substituted with a halogen atom;

an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom);

a cyano group;

—$NR^{30}R^{31}$ (where $R^{30}$ and $R^{31}$ are each independently a hydrogen atom or a $C_1$ to $C_4$ alkyl group that may be substituted with a halogen atom);

a nitro group;

a carbamoyl group;

an N—($C_1$ to $C_4$ alkyl)carbamoyl group;

an N,N-di($C_1$ to $C_4$ alkyl)carbamoyl group;

—$NHCOR^9$ (where $R^9$ is a $C_1$ to $C_4$ alkyl group that may be branched and that may be substituted with a halogen atom); and a halogen atom;

with the proviso that a case where both $R^{14}$ and $R^{15}$ are hydrogen atoms is excluded, $R^{16}$ is a group selected from the group consisting of:

(i) a hydrogen atom;

(ii) a $C_1$ to $C_{10}$ alkyl group that may be branched or form a cyclic group and that may be substituted with a halogen atom, wherein the alkyl group may be substituted with at least one group selected from the group consisting of:

a $C_1$ to $C_5$ alkoxy group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), a halogen atom, —$COR^9$ (where $R^9$ is a $C_1$ to $C_4$ alkyl group that may be branched and that may be substituted with a halogen atom), and —$CO_2R^9$ (where $R^9$ is a $C_1$ to $C_4$ alkyl group that may be branched and that may be substituted with a halogen atom);

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(vi) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or $—NHCOR^9$ (where $R^9$ is a $C_1$ to $C_4$ alkyl group that may be branched and that may be substituted with a halogen atom), a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, $—NHCOR^9$ (where $R^9$ is a $C_1$ to $C_4$ alkyl group that may be branched and that may be substituted with a halogen atom), and a halogen atom;

(vii) an aryl group, wherein the aryl group may be substituted with at least one group selected from the group consisting of:

a $C_1$ to $C_4$ alkyl group that may be branched and that may be substituted with a halogen atom a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or $—NHCOR^9$ (where $R^9$ is a $C_1$ to $C_4$ alkyl group that may be branched and that may be substituted with a halogen atom), a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, $—NHCOR^9$ (where $R^9$ is a $C_1$ to $C_4$ alkyl group that may be branched and that may be substituted with a halogen atom), and a halogen atom; and (viii) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or $—NHCOR^9$ (where $R^9$ is a $C_1$ to $C_4$ alkyl group that may be branched and that may be substituted with a halogen atom), a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, $—NHCOR^9$ (where $R^9$ is a $C_1$ to $C_4$ alkyl group that may be branched and that may be substituted with a halogen atom), and a halogen atom;

$R^{17}$ is a $C_1$ to $C_8$ alkyl group that may be branched or form a cyclic group and that may be substituted with a halogen atom;

in the formula (V) and formula (VI), $R^{18}$ is a group selected from the group consisting of:

(i) a $C_1$ to $C_{10}$ alkyl group that may be branched or form a cyclic group and that may be substituted with a halogen atom, wherein the alkyl group may be substituted with at least one group selected from the group consisting of:

a $C_1$ to $C_5$ alkoxy group that may be branched and that may be substituted with a halogen atom, a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, $—NHCOR^9$ (where $R^9$ is a $C_1$ to $C_4$ alkyl group that may be branched and that may be substituted with a halogen atom), a halogen atom, $—COR^9$ (where $R^9$ is a $C_1$ to $C_4$ alkyl group that may be branched and that may be substituted with a halogen atom), and $—CO_2R^9$ (where $R^9$ is a $C_1$ to $C_4$ alkyl group that may be branched and that may be substituted with a halogen atom);

(ii) a $C_3$ to $C_9$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, $—NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or $—NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(vi) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom; and (vii) a $C_3$ to $C_9$ propargyl group or substituted propargyl group that may be branched and that may be substituted with a halogen atom; and in the formula (V), W is a functional group having a leaving ability, and in the formula (VI),

* shows a newly produced asymmetric center.

In one embodiment, $R^7$ and $R^8$ of the compound represented by the formula (I) are groups independently selected from the group consisting of:

(i) a $C_1$ to $C_{30}$ alkyl group that may be branched or form a cyclic group and that may be substituted with a halogen atom;

(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom;

(iv) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(v) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(vi) —$(CH_2)_nOCONR^{10}R^{11}$ (where $R^{10}$ and $R^{11}$ are groups independently selected from the group consisting of:

(1) a hydrogen atom;

(2) a $C_1$ to $C_4$ alkyl group that may be branched and that may be substituted with a halogen atom;

(3) a $C_2$ to $C_6$ alkenyl group that may be branched or form a cyclic group and that may be substituted with a halogen atom;

(4) a $C_2$ to $C_6$ alkynyl group that may be branched or form a cyclic group and that may be substituted with a halogen atom;

(5) an aralkyl group, wherein the aryl moiety of the aralkyl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom;

(6) a heteroaralkyl group having a heteroaryl moiety, wherein the heteroaryl moiety may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom;

(7) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom; and (8) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom;

and n is an integer from 1 to 12);

(vii) —$(CH_2)_nCONR^{12}R^{13}$ (where $R^{12}$ and $R^{13}$ are groups independently selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom, and n is an integer from 1 to 12);

(viii) —(CH$_2$)$_n$NR$^{12}$COR$^{13}$ (where R$^{12}$ and R$^{13}$ are groups independently selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom; and (4) a heteroaryl group, wherein the heteroaryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NHCOR$^9$ (where R$^9$ is a $C_1$ to $C_4$ alkyl group that may be branched and that may be substituted with a halogen atom), a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —NHCOR$^9$ (where R$^9$ is a $C_1$ to $C_4$ alkyl group that may be branched and that may be substituted with a halogen atom), and a halogen atom;

and n is an integer from 1 to 12);

(ix) —(CH$_2$)$_n$NR$^{12}$R$^{13}$ (where R$^{12}$ and R$^{13}$ are groups independently selected from the group consisting of:

(1) a hydrogen atom;

(2) a $C_1$ to $C_4$ alkyl group that may be branched and that may be substituted with a halogen atom;

(3) an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —NR$^{30}$R$^{31}$ (where R$^{30}$ and R$^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom,
and n is an integer from 1 to 12);
(x) —(CH$_2$)$_n$Y—OR$^{12}$ (where Y is a C$_1$ to C$_4$ divalent saturated hydrocarbon group that may be branched and that may be substituted with a halogen atom, and R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12);
(xi) —(CH$_2$)—OR$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom,
and n is an integer from 1 to 12);
(xii) —(CH$_2$)$_n$—S—R$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom,
and n is an integer from 1 to 12);
(xiii) —(CH$_2$)$_n$—SO—R$^2$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12); and
(xiv) —(CH$_2$)$_n$—SO$_2$—R$^{12}$ (where R$^{12}$ is a group selected from the group consisting of:
(1) a hydrogen atom;
(2) a C$_1$ to C$_4$ alkyl group that may be branched and that may be substituted with a halogen atom;
(3) an aryl group, wherein the aryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NH- COR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom; and
(4) a heteroaryl group, wherein the heteroaryl group may be substituted with at least one group selected from the group consisting of:
a C$_1$ to C$_4$ alkyl group that may be branched and that may be substituted with a halogen atom,
a C$_1$ to C$_5$ alkoxy group that may be branched and that may be substituted with a halogen atom,
an aryl group that may be substituted with a halogen atom, a C$_1$ to C$_4$ alkyl group that may be branched and that may be substituted with a halogen atom, a cyano group, —NR$^{30}$R$^{31}$ (where R$^{30}$ and R$^{31}$ are each independently a hydrogen atom or a C$_1$ to C$_4$ alkyl group that may be substituted with a halogen atom), a nitro group, a carbamoyl group, an N—(C$_1$ to C$_4$ alkyl)carbamoyl group, an N,N-di(C$_1$ to C$_4$ alkyl)carbamoyl group, or —NHCOR$^9$ (where R$^9$ is a C$_1$ to C$_4$ alkyl group that may be branched and that may be substituted with a halogen atom),
a cyano group,
—NR$^{30}$R$^{31}$ (where R$^{30}$ and R$^{31}$ are each independently a hydrogen atom or a C$_1$ to C$_4$ alkyl group that may be substituted with a halogen atom),
a nitro group,
a carbamoyl group,
an N—(C$_1$ to C$_4$ alkyl)carbamoyl group,
an N,N-di(C$_1$ to C$_4$ alkyl)carbamoyl group,
—NHCOR$^9$ (where R$^9$ is a C$_1$ to C$_4$ alkyl group that may be branched and that may be substituted with a halogen atom), and
a halogen atom;
and n is an integer from 1 to 12); or
R$^7$ and R$^8$ are taken together to form a divalent group selected from the group consisting of:
—(CH$_2$)$_m$— (where m is an integer from 2 to 8);

-continued

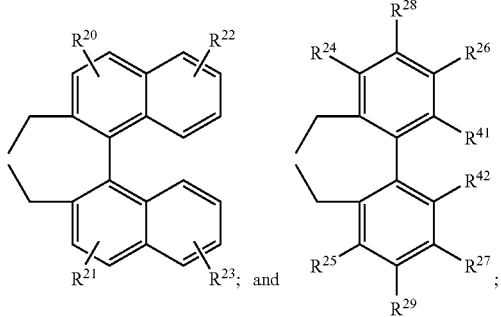

(where $R^{20}$, $R^{21}$, $R^{22}$, $R^{23}$, $R^{24}$, $R^{25}$, $R^{26}$, $R^{27}$, $R^{28}$, $R^{29}$, $R^{41}$, and $R^{42}$ are groups independently selected from the group consisting of:

a hydrogen atom;

a $C_1$ to $C_8$ alkyl group that may be branched or form a cyclic group, and/or that may be substituted with a halogen atom;

a $C_2$ to $C_8$ alkenyl group that may be branched or form a cyclic group, and/or that may be substituted with a halogen atom;

a $C_2$ to $C_8$ alkynyl group that may be branched or form a cyclic group, and/or that may be substituted with a halogen atom;

an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, $-NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_9$ alkylene group;

a hetroaryl group, which may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, $-NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, $-NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaralkyl group, which has a hetroaryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, $-NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a ($C_1$ to $C_3$ alkoxy)carbonyl group;

a carbamoyl group;

an N—($C_1$ to $C_4$ alkyl)carbamoyl group; and an N,N-di($C_1$ to $C_4$ alkyl)carbamoyl group (where the $C_1$ to $C_4$ alkyl groups may be the same or different)).

In a further embodiment, each of $R^1$, $R^{1'}$, $R^2$, $R^{2'}$, $R^3$, and $R^{3'}$ of the compound represented by the formula (I) is a $C_1$ to $C_5$ alkoxy group that may be branched or form a cyclic group and that may be substituted with a halogen atom.

In another embodiment, each of $R^1$, $R^{1'}$, $R^2$, $R^{2'}$, $R^3$, and $R^{3'}$ of the compound represented by the formula (I) is a methoxy group, an ethoxy group, or a benzyloxy group.

In a further embodiment, $R^4$ and $R^{4'}$ of the compound represented by the formula (I) are groups independently selected from the group consisting of:

a hydrogen atom; and an aryl group, wherein the aryl group may be substituted with at least one group selected from the group consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, $-NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or $-NH-COR^9$ (where $R^9$ is a $C_1$ to $C_4$ alkyl group that may be branched and that may be substituted with a halogen atom), a cyano group, $-NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, $-NHCOR^9$ (where $R^9$ is a $C_1$ to $C_4$ alkyl group that may be branched and that may be substituted with a halogen atom), and a halogen atom.

In a still further embodiment, each of $R^4$ and $R^{4'}$ of the compound represented by the formula (I) is a 3,4,5-trifluorophenyl group or a 3,5-bis(trifluoromethyl)phenyl group.

In a further embodiment, $R^7$ and $R^8$ of the compound represented by the formula (I) are each independently a $C_1$ to $C_{30}$ alkyl group that may be branched or form a cyclic group and that may be substituted with a halogen atom.

In a still further embodiment, $R^7$ and $R^8$ of the compound represented by the formula (I) are both n-butyl groups.

In one embodiment, the inorganic base is used in the form of an aqueous inorganic-base solution.

In a further embodiment, the inorganic base in the aqueous inorganic-base solution is used in a ratio of at least 0.5 equivalents up to 280 equivalents per 1 equivalent of the compound represented by the formula (IV).

In a still further embodiment, a concentration of the aqueous inorganic-base solution is from 10 w/w % to 70 w/w %.

In a still further embodiment, the compound represented by the formula (I) is used in a ratio of 0.0001 mol % to 10 mol % per 1 mol of the compound represented by the formula (IV).

In a still further embodiment, a volume ratio between the medium and the aqueous inorganic-base solution is 7:1 to 1:5.

The present invention also provides a method for producing an optically active α-amino acid, comprising:

a step of hydrolyzing an imino group ($R^{14}R^{15}C=N—$) of the compound represented by the formula (VI) that is obtained by any one of the above-described method under acidic conditions:

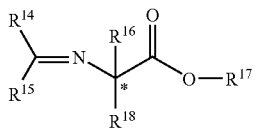

(wherein $R^{14}$, $R^{15}$, $R^{16}$, $R^{17}$, and $R^{18}$ are the same groups as defined above); and a step of hydrolyzing an ester group ($—CO_2R^{17}$) of the acid-hydrolysis product under acidic or basic conditions.

The present invention also provides a method for producing an optically active α-amino acid, comprising:

a step of hydrolyzing an ester group ($—CO_2R^{17}$) of the compound represented by the formula (VI) that is obtained by any one of the above-described method under basic conditions:

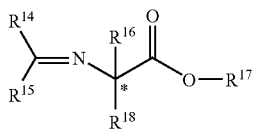

(wherein $R^{14}$, $R^{15}$, $R^{16}$, $R^{17}$, and $R^{18}$ are the same groups as defined above); and a step of hydrolyzing an imino group ($R^{14}R^{15}C=N—$) of the base-hydrolysis product under acidic conditions.

The present invention provides a chiral phase-transfer catalyst that has a more simplified structure. This phase-transfer catalyst can be produced in a fewer steps than conventional ones. Thus, the phase-transfer catalyst of the present invention that can be provided more easily can be used, for example, in the synthesis of α-alkyl-α-amino acid derivatives and α,α-dialkyl-α-amino acid.

BEST MODE FOR CARRYING OUT THE INVENTION

Hereinafter, the terms used in the present invention will be defined.

The phrase "$C_1$ to $C_n$ alkyl group that may be branched or form a cyclic group" (where n is an integer) includes any linear alkyl group having 1 to n carbon atoms, any branched alkyl group having 3 to n carbon atoms, and any cyclic alkyl group having 3 to n carbon atoms. Examples of linear alkyl groups having 1 to 6 carbon atoms include methyl, ethyl, n-propyl, n-butyl, n-pentyl, and n-hexyl. Examples of branched alkyl groups having 3 to 6 carbon atoms include isopropyl, isobutyl, tert-butyl, and isopentyl. Examples of cyclic alkyl groups having 3 to 6 carbon atoms include cyclobutyl, cyclopentyl, and cyclohexyl. Furthermore, when "$C_1$ to $C_{12}$ alkyl group that may be branched or form a cyclic group and/or may be substituted with a halogen atom" is referred to, any linear alkyl group having 1 to 12 carbon atoms, any branched alkyl group having 3 to 12 carbon atoms, and any cyclic alkyl group having 3 to 12 carbon atoms are included, and a hydrogen atom at any position of these alkyl groups may be substituted with a halogen atom. Examples of alkyl groups include n-heptyl, isoheptyl, n-octyl, isooctyl, n-decyl, and n-dodecyl.

In N—($C_1$ to $C_4$ alkyl) carbamoyl groups and N,N-di($C_1$ to $C_4$ alkyl) carbamoyl groups, "$C_1$ to $C_4$ alkyl" means a $C_1$ to $C_4$ linear alkyl group or a $C_3$ to $C_4$ branched alkyl group.

The phrase "$C_2$ to $C_n$ alkenyl group that may be branched or form a cyclic group" (where n is an integer) includes any linear alkenyl group having 2 to n carbon atoms, any branched alkenyl group having 3 to n carbon atoms, and any cyclic alkenyl group having 3 to n carbon atoms. Examples of linear alkenyl groups having 2 to 6 carbon atoms include ethenyl, 1-propenyl, 2-propenyl, 1-butenyl, 2-butenyl, 1-pentenyl, 2-pentenyl, 3-pentenyl, 4-pentenyl, and 1-hexenyl. Examples of branched alkenyl groups having 3 to 6 carbon atoms include isopropenyl, 1-methyl-1-propenyl, 1-methyl-2-propenyl, 2-methyl-1-propenyl, 2-methyl-2-propenyl, and 1-methyl-2-butenyl. Examples of cyclic alkenyl groups having 3 to 6 carbon atoms include cyclobutenyl, cyclopentenyl, and cyclohexenyl. Furthermore, when "$C_2$ to $C_{12}$ alkenyl group that may be branched or form a cyclic group and/or may be substituted with a halogen atom" is referred to, any linear alkenyl group having 2 to 12 carbon atoms, any branched alkenyl group having 3 to 12 carbon atoms, and any cyclic alkenyl group having 3 to 12 carbon atoms are included, and a hydrogen atom at any position of these alkenyl groups may be substituted with a halogen atom. Examples of such alkenyl groups include 1-heptenyl, 2-heptenyl, 1-octenyl, 1-decenyl, and 1-dodecenyl.

The phrase "$C_2$ to $C_n$ alkynyl group that may be branched or form a cyclic group" (where n is an integer) includes any linear alkynyl group having 2 to n carbon atoms, any branched alkynyl group having 3 to n carbon atoms, and any cyclic alkynyl group having 3 to n carbon atoms. Examples of linear alkynyl groups having 2 to 6 carbon atoms include ethynyl, 1-propynyl, 2-propynyl, 1-butynyl, 2-butynyl, 1-pentynyl, and 1-hexynyl. Examples of branched alkynyl groups having 3 to 6 carbon atoms include 1-methyl-2-propynyl. Examples of cyclic alkynyl groups having 3 to 6 carbon atoms include cyclopropylethynyl, and cyclobutylethynyl. Furthermore, when "$C_2$ to $C_{12}$ alkynyl group that may be branched or form a cyclic group and/or may be substituted with a halogen atom" is referred to, any linear alkynyl groups having 1 to 12 carbon atoms, any branched alkynyl groups having 3 to 12 carbon atoms, and any cyclic alkynyl groups having 3 to 12 carbon atoms are included, and a hydrogen atom at any position of these alkynyl groups may be substituted with a halogen atom. Examples of such alkynyl groups include 1-heptynyl, 1-octynyl, 1-decynyl, and 1-dodecynyl.

The phrase "$C_1$ to $C_n$ alkoxy group that may be branched" (where n is an integer) includes alkoxy groups having any linear alkyl groups having 1 to n carbon atoms and alkoxy groups having any branched alkyl groups having 3 to n carbon atoms. Examples thereof include methyloxy, ethyloxy, n-propyloxy, isopropyloxy, and tert-butyloxy.

Examples of "aralkyl group" in the present invention include benzyl, phenethyl, and naphthylmethyl.

Examples of "heteroaralkyl group" in the present invention include pyridylmethyl, indolylmethyl, furylmethyl, thienylmethyl, and pyrrolylmethyl.

Examples of "aryl group" in the present invention include phenyl, naphthyl, anthracenyl and phenanthryl.

Examples of "heteroaryl group" in the present invention include pyridyl, pyrrolyl, imidazolyl, furyl, indolyl, benzothiophen-2-yl, thienyl, oxazolyl, thiazolyl, 3,4-methylenedioxyphenyl, 3,4-ethylenedioxyphenyl and tetrazolyl.

Examples of "halogen atom" in the present invention include a chlorine atom, a bromine atom, an iodine atom, and a fluorine atom. In the present invention, the term "halide anion" refers to halogen ions and examples thereof include a chloride ion, a bromide ion, an iodide ion and a fluoride ion.

The phrase "$C_3$ to $C_n$ allyl group or substituted allyl group that may be branched or form a cyclic group" (where n is an integer) refers to allyl groups or any substituted allyl groups having a substituent(s) at position 1 and/or 2 and/or 3 and having 4 to n carbon atoms in total, and for example, includes 2-butenyl, 1-cyclopentenylmethyl, and 3-methyl-2-butenyl.

The phrase "$C_3$ to $C_n$ propargyl group or substituted propargyl group that may be branched" (where n is an integer) refers to propargyl groups or any substituted propargyl groups having a substituent(s) at position 1 and/or 3 and having 4 to n carbon atoms in total, and for example, includes 2-butynyl, and 3-trimethylsilyl-2-propynyl.

In the present invention, the term "functional group having a leaving ability" means an atom or a group of atoms that leaves from a substrate in a substitution reaction or an elimination reaction, that is, a leaving group, and for example, includes a halogen atom, and a sulfonyloxy group.

In the present specification, the term "group (Q)" is used to simplify the description, for convenience, and is referred to the group consisting of:

a $C_1$ to $C_4$ alkyl group that may be branched, a $C_1$ to $C_5$ alkoxy group that may be branched, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom.

Hereinafter, the present invention will be described more specifically.

<Quaternary Ammonium Salt>

A quaternary ammonium salt of the present invention is pure with respect to its axial asymmetry, and is a compound represented by the following formula (I):

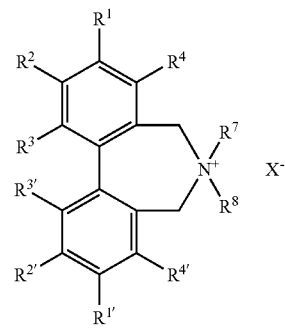

(I)

(where $R^1$, $R^{1'}$, $R^2$, and $R^{2'}$ are each independently:

a hydrogen atom;

a halogen atom;

a $C_1$ to $C_5$ alkyl group that may be substituted with a halogen atom and/or an aryl group, and/or that may be branched or form a cyclic group; or a $C_1$ to $C_5$ alkoxy group that may be substituted with a halogen atom and/or an aryl group, and/or that may be branched or form a cyclic group;

$R^3$ and $R^{3'}$ are each independently:

a halogen atom;

a $C_1$ to $C_5$ alkyl group that may be substituted with a halogen atom and/or an aryl group, and/or that may be branched or form a cyclic group; or a $C_1$ to $C_5$ alkoxy group that may be substituted with a halogen atom and/or an aryl group, and/or that may be branched or form a cyclic group;

$R^4$ and $R^{4'}$ are each independently a group selected from the group consisting of:

(i) a hydrogen atom;

(ii) —$NR^{30}R^{31}$ (where $R^{30}$ and $R^{31}$ are each independently a hydrogen atom or a $C_1$ to $C_4$ alkyl group that may be substituted with a halogen atom);

(iii) a cyano group;

(iv) a nitro group;

(v) a carbamoyl group;

(vi) an N—($C_1$ to $C_4$ alkyl)carbamoyl group;

(vii) an N,N-di($C_1$ to $C_4$ alkyl)carbamoyl group;

(viii) —$NHCOR^9$ (where $R^9$ is a $C_1$ to $C_4$ alkyl group that may be branched and that may be substituted with a halogen atom);

(ix) a halogen atom;

(x) a $C_1$ to $C_6$ alkyl group that may be branched or form a cyclic group and that may be substituted with a halogen atom;

(xi) a $C_2$ to $C_6$ alkenyl group that may be branched or form a cyclic group and that may be substituted with a halogen atom;

(xii) a $C_2$ to $C_6$ alkynyl group that may be branched or form a cyclic group and that may be substituted with a halogen atom;

(xiii) an aralkyl group, wherein the aryl moiety of the aralkyl group may be substituted with at least one group selected from the group (Q) consisting of:

a $C_1$ to $C_4$ alkyl group that may be branched and that may be substituted with a halogen atom, a $C_1$ to $C_5$ alkoxy group that may be branched and that may be substituted with a halogen atom, an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom), a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, —$NHCOR^9$ (where $R^9$ is a $C_1$ to $C_4$ alkyl group that may be branched and that may be substituted with a halogen atom), and a halogen atom;

(xiv) a heteroaralkyl group having a heteroaryl moiety, wherein the heteroaryl moiety may be substituted with at least one group selected from the group (Q);

(xv) an aryl group, wherein the aryl group may be substituted with at least one group selected from the group (Q) or may be substituted with —O—$(CH_2)_p$—O— (where p is 1 or 2) at positions 3 and 4 that are taken together;

(xvi) a heteroaryl group, wherein the heteroaryl group may be substituted with at least one group selected from the group (Q); and (xvii) —$S(O)_n$—R (where n is 0, 1, or 2, and R is a $C_1$ to $C_4$ alkyl group that may be branched and that may be substituted with a halogen atom);

$R^7$ and $R^8$ are each independently a monovalent organic group or taken together to form a divalent organic group, and $X^-$ is a halide anion, $SCN^-$, $HSO_4^-$, $HF_2^-$, $CF_3SO_3^-$, $CH_3$-Ph-$SO_3^-$, or $CH_3SO_3^-$). The compound represented by the formula (I) may have a configuration of either (S) or (R).

The compound represented by the formula (I) functions usefully as a phase-transfer catalyst for producing, for example, an optically active α-amino acid or derivative thereof, and in particular, an α,α-dialkyl-α-amino acid or derivative thereof as described later. More specifically, when the compound represented by the formula (I) is used as a phase-transfer catalyst in order to produce an optically active α-amino acid or derivative thereof represented by the formula (VI) by alkylating a compound represented by the formula (IV) with a compound represented by the formula (V), the ammonium moiety constituting a cation of this compound:

contributes to the reactivity in the alkylation, and the biphenyl moiety:

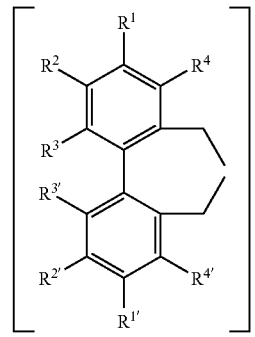

contributes to the stereoselectivity of the alkylation reaction. Therefore, in one embodiment, $R^7$ and $R^8$ in the compound represented by the formula (I) are groups that can retain the catalytic activity and selectivity arising from the ammonium moiety and the biphenyl moiety of the cation, respectively (or inhibit neither catalytic activity nor selectivity). For example, they can be monovalent organic groups or divalent organic groups that are inactive compared to the ammonium moiety and the biphenyl moiety. In other words, it is not necessary for $R^7$ and $R^8$ to be groups which themselves (or itself) have excellent reactivity, and rather, it is sufficient for them not to adversely affect the reactions in the production of the amino acids or derivatives thereof as described later. Alternatively, if the compound represented by the formula (I) is used as a phase-transfer catalyst for producing an optically active α-amino acid or a derivative thereof as described later, $R^7$ and $R^8$ in the formula (I) are each independently a monovalent group or a monovalent organic group selected from the group consisting of:

(i) a $C_1$ to $C_{30}$ alkyl group that may be branched or form a cyclic group and that may be substituted with a halogen atom;

(ii) a $C_2$ to $C_{12}$ alkenyl group that may be branched or form a cyclic group and that may be substituted with a halogen atom;

(iii) a $C_2$ to $C_{12}$ alkynyl group that may be branched or form a cyclic group and that may be substituted with a halogen atom;

(iv) an aryl group, wherein the aryl group may be substituted with at least one group selected from the group (Q);

(v) a heteroaryl group, wherein the heteroaryl group may be substituted with at least one group selected from the group (Q);

(vi) —$(CH_2)OCONR^{10}R^{11}$ (where $R^{10}$ and $R^{11}$ are groups independently selected from the group consisting of:

(1) a hydrogen atom;

(2) a $C_1$ to $C_4$ alkyl group that may be branched and that may be substituted with a halogen atom;

(3) a $C_2$ to $C_6$ alkenyl group that may be branched or form a cyclic group and that may be substituted with a halogen atom;

(4) a $C_2$ to $C_6$ alkynyl group that may be branched or form a cyclic group and that may be substituted with a halogen atom;

(5) an aralkyl group, wherein the aryl moiety of the aralkyl group may be substituted with at least one group selected from the group (Q);

(6) a heteroaralkyl group having a heteroaryl moiety, wherein the heteroaryl moiety may be substituted with at least one group selected from the group (Q);

(7) an aryl group, wherein the aryl group may be substituted with at least one group selected from the group (Q); and
(8) a heteroaryl group, wherein the heteroaryl group may be substituted with at least one group selected from the group (Q), and n is an integer from 1 to 12);
(vii) —$(CH_2)_n CONR^{12}R^{13}$ (where $R^{12}$ and $R^{13}$ are groups independently selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);
(viii) —$(CH_2)_n NR^{12}COR^{13}$ (where $R^{12}$ and $R^{13}$ are groups independently selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);
(ix) —$(CH_2)_n NR^{12}R^{13}$ (where $R^{12}$ and $R^{13}$ are groups independently selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);
(x) —$(CH_2)_n Y$—$OR^{12}$ (where Y is a $C_1$ to $C_4$ divalent saturated hydrocarbon group that may be branched and that may be substituted with a halogen atom, and $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);
(xi) —$(CH_2)_n$—$OR^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);

(xii) —$(CH_2)_n$—S—$R^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);
(xiii) —$(CH_2)$—SO—$R^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12); and
(xiv) —$(CH_2)_n$—$SO_2$—$R^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12); or
$R^7$ and $R^8$ are taken together to form a (divalent organic) group selected from the group consisting of:
—$(CH_2)_m$— (where m is an integer from 2 to 8);

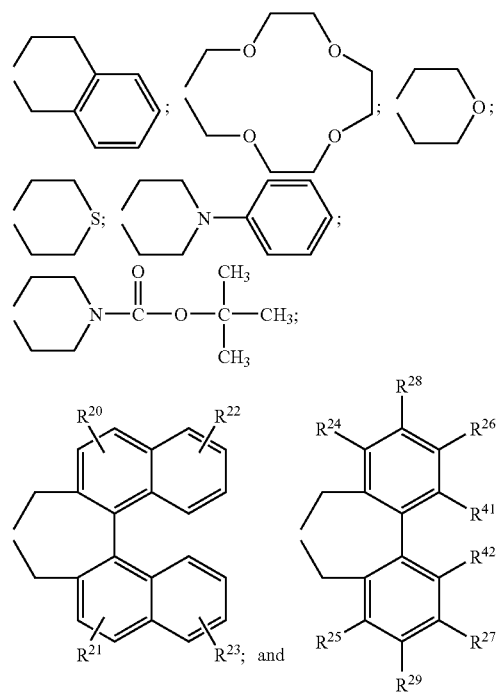

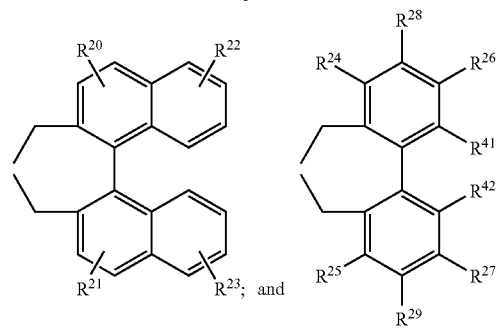

(where $R^{20}$, $R^{21}$, $R^{22}$, $R^{23}$, $R^{24}$, $R^{25}$, $R^{26}$, $R^{27}$, $R^{28}$, $R^{29}$, $R^{41}$, and $R^{42}$ are groups independently selected from the group consisting of:

a hydrogen atom;

a $C_1$ to $C_8$ alkyl group that may be branched or form a cyclic group, and/or that may be substituted with a halogen atom;

a $C_2$ to $C_8$ alkenyl group that may be branched or form a cyclic group, and/or that may be substituted with a halogen atom;

a $C_2$ to $C_8$ alkynyl group that may be branched or form a cyclic group, and/or that may be substituted with a halogen atom;

an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaryl group, which may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetroaralkyl group, which has a hetroaryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —$NR^{30}R^{31}$ (where $R^{30}$ and $R^{31}$ are each independently a hydrogen atom or a $C_1$ to $C_4$ alkyl group that may be substituted with a halogen atom), or a cyclic amino group that is formed by a $C_2$ to $C_8$ alkylene group;

a ($C_1$ to $C_3$ alkoxy) carbonyl group;

a carbamoyl group;

an N—($C_1$ to $C_4$ alkyl)carbamoyl group; and an N,N-di($C_1$ to $C_4$ alkyl)carbamoyl group (where the $C_1$ to $C_4$ alkyl groups may be the same or different)).

In the present invention, all of $R^1$, $R^{1'}$, $R^2$, $R^{2'}$, $R^3$, and $R^3$ of the compound represented by the formula (I) are preferably $C_1$ to $C_5$ alkoxy groups that may be branched or form a cyclic group, and that may be substituted with a halogen atom. In consideration of the availability of the below-mentioned starting material, it is preferable that all of $R^1$, $R^{1'}$, $R^2$, $R^{2'}$, $R^3$, and $R^{3'}$ of the compound represented by the formula (I) are a methoxy group, an ethoxy group, or a benzyloxy group.

Alternatively, in the present invention, it is also preferable that $R^4$ and $R^{4'}$ of the compound represented by the formula (I) are each independently selected from the group consisting of:

a hydrogen atom, and an aryl group, wherein the aryl group may be substituted with at least one group selected from the group (Q). In particular, it is preferable that $R^4$ and $R^{4'}$ of the compound represented by the formula (I) are a 3,4,5-trifluorophenyl group or a 3,5-bis(trifluoromethyl)phenyl group. This is because if the compound represented by the formula (I) having such a substituent group is used as a phase-transfer catalyst for producing an optically active α-amino acid and derivatives thereof, and in particular α,α-dialkyl-α-amino acids or derivates thereof, then the amino acid or derivatives thereof can be produced with excellent yield and optical purity.

Alternatively, in the present invention, $R^7$ and $R^8$ of the compound represented by the formula (I) are preferably each independently a $C_1$ to $C_{30}$ alkyl group that may be branched or form a cyclic group and that may be substituted with a halogen atom. In this specification, $R^7$ and $R^8$ are preferably, each independently, a $C_1$ to $C_{12}$ alkyl group that may be branched or form a cyclic group and that may be substituted with a halogen atom, or a $C_{13}$ to $C_{30}$ alkyl group that may be branched or form a cyclic group and that may be substituted with a halogen atom (more preferably a $C_{13}$ to $C_{22}$ alkyl group that may be branched or form a cyclic group and that may be substituted with a halogen atom). In this specification, $R^7$ and $R^8$ are preferably, each independently, an alkyl group that may be branched or form a cyclic group and that may be substituted with a halogen atom, and more preferably the number of carbons in the alkyl group can be selected from a range in which the lower limit is at least 1, at least 3, at least 13, at least 15, at least 17, or at least 18, and the upper limit is not more than 30, not more than 22, not more than 21, not more than 20, not more than 12, not more than 8, or not more than 4. In particular, in the formula (I), it is preferable that $R^7$ and $R^8$ of the compound are both n-butyl groups. This is because if the compound represented by the formula (I) having such a substituent group is used as a phase-transfer catalyst for producing an optically active α-amino acid and derivatives thereof, and in particular α,α-dialkyl-α-amino acids or derivates thereof, then the amino acid or derivatives thereof can be produced with excellent yield and optical purity.

Alternatively, in the present invention, it is preferable that $R^1$ and $R^{1'}$ of the compound represented by the formula (I) are the same.

Alternatively, in the present invention, it is preferable that $R^2$ and $R^{2'}$ of the compound represented by the formula (I) are the same.

Alternatively, in the present invention, it is preferable that $R^3$ and $R^{3'}$ of the compound represented by the formula (I) are the same.

Alternatively, in the present invention, it is preferable that $R^4$ and $R^{4'}$ of the compound represented by the formula (I) are the same.

Alternatively, in the present invention, it is preferable that $R^7$ and $R^8$ of the compound represented by the formula (I) are the same.

<Method of Producing the Quaternary Ammonium Salt>

The quaternary ammonium salt represented by the formula (I) can be produced by reacting a compound represented by the following formula (II):

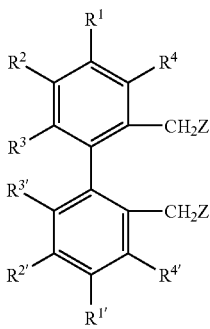
(II)

with a secondary amine represented by the following formula (III):

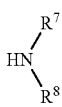
(III)

in an organic solvent in the presence of an acid-scavenging agent.

Here, in the formula (II), $R^1$, $R^{1'}$, $R^2$, and $R^{2'}$ are each independently:
a hydrogen atom;
a halogen atom;
a $C_1$ to $C_5$ alkyl group that may be substituted with a halogen atom and/or an aryl group, and/or that may be branched or form a cyclic group; or
a $C_1$ to $C_5$ alkoxy group that may be substituted with a halogen atom and/or an aryl group, and/or that may be branched or form a cyclic group;

$R^3$ and $R^{3'}$ are each independently:
a halogen atom;
a $C_1$ to $C_5$ alkyl group that may be substituted with a halogen atom and/or an aryl group, and/or that may be branched or form a cyclic group; or
a $C_1$ to $C_5$ alkoxy group that may be substituted with a halogen atom and/or an aryl group, and/or that may be branched or form a cyclic group;

$R^4$ and $R^{4'}$ are groups independently selected from the group consisting of:
  (i) a hydrogen atom;
  (ii) —$NR^{30}R^{31}$ (where $R^{30}$ and $R^{31}$ are each independently a hydrogen atom or a $C_1$ to $C_4$ alkyl group than may be substituted with a halogen atom);
  (iii) a cyano group;
  (iv) a nitro group;
  (v) a carbamoyl group;
  (vi) an N—($C_1$ to $C_4$ alkyl)carbamoyl group;
  (vii) an N,N-di($C_1$ to $C_4$ alkyl)carbamoyl group;
  (viii) —$NHCOR^9$ (where $R^9$ is a $C_1$ to $C_4$ alkyl group that may be branched and that may be substituted with a halogen atom);
  (ix) a halogen atom;
  (x) a $C_1$ to $C_6$ alkyl group that may be branched or form a cyclic group and that may be substituted with a halogen atom;
  (xi) a $C_2$ to $C_6$ alkenyl group that may be branched or form a cyclic group and that may be substituted with a halogen atom;
  (xii) a $C_2$ to $C_6$ alkynyl group that may be branched or form a cyclic group and that may be substituted with a halogen atom;
  (xiii) an aralkyl group, wherein the aryl moiety of the aralkyl group may be substituted with at least one group selected from the group (Q);
  (xiv) a heteroaralkyl group having a heteroaryl moiety, wherein the heteroaryl moiety may be substituted with at least one group selected from the group (Q);
  (xv) an aryl group, wherein the aryl group may be substituted with at least one group selected from the group (Q) or may be substituted with —O—$(CH_2)_p$—O— (where p is 1 or 2) at positions 3 and 4 that are taken together; and
  (xvi) a heteroaryl group, wherein the heteroaryl group may be substituted with at least one group selected from the group (Q); and
  (xvii) —$S(O)_n$—R (where n is 0, 1, or 2, and R is a $C_1$ to $C_4$ alkyl group that may be branched and that may be substituted with a halogen atom); and Z is a halogen atom.

On the other hand, in the formula (III),
$R^7$ and $R^8$ are groups independently selected from the group consisting of:
  (i) a $C_1$ to $C_{30}$ alkyl group that may be branched or form a cyclic group and that may be substituted with a halogen atom;
  (ii) a $C_2$ to $C_{12}$ alkenyl group that may be branched or form a cyclic group and that may be substituted with a halogen atom;
  (iii) a $C_2$ to $C_{12}$ alkynyl group that may be branched or form a cyclic group and that may be substituted with a halogen atom;
  (iv) an aryl group, wherein the aryl group may be substituted with at least one group selected from the group (Q);
  (v) a heteroaryl group, wherein the heteroaryl group may be substituted with at least one group selected from the group (Q);
  (vi) —$(CH_2)_n OCONR^{10}R^{11}$ (where $R^{10}$ and $R^{11}$ are groups independently selected from the group consisting of:
    (1) a hydrogen atom;
    (2) a $C_1$ to $C_4$ alkyl group that may be branched and that may be substituted with a halogen atom;
    (3) a $C_2$ to $C_6$ alkenyl group that may be branched or form a cyclic group and that may be substituted with a halogen atom;
    (4) a $C_2$ to $C_6$ alkynyl group that may be branched or form a cyclic group and that may be substituted with a halogen atom;
    (5) an aralkyl group, wherein the aryl moiety of the aralkyl group may be substituted with at least one group selected from the group (Q);
    (6) a heteroaralkyl group having a heteroaryl moiety, wherein the heteroaryl moiety may be substituted with at least one group selected from the group (Q);
    (7) an aryl group, wherein the aryl group may be substituted with at least one group selected from the group (Q); and
    (8) a heteroaryl group, wherein the heteroaryl group may be substituted with at least one group selected from the group (Q), and n is an integer from 1 to 12);
  (vii) —$(CH_2) CONR^{12}R^{13}$ (where $R^{12}$ and $R^{13}$ are groups independently selected from the group consisting of:
    (1) a hydrogen atom;
    (2) a $C_1$ to $C_4$ alkyl group that may be branched and that may be substituted with a halogen atom;
    (3) an aryl group, wherein the aryl group may be substituted with at least one group selected from the group (Q); and (4) a heteroaryl group, wherein the heteroaryl group may be substituted with at least one group selected from the group (Q), and n is an integer from 1 to 12);

(viii) —$(CH_2)_n NR^{12}COR^{13}$ (where $R^{12}$ and $R^{13}$ are groups independently selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);

(ix) —$(CH_2)_n NR^{12}R^{13}$ (where $R^{12}$ and $R^{13}$ are groups independently selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);

(x) —$(CH_2)_n Y$—$OR^{12}$ (where Y is a $C_1$ to $C_4$ divalent saturated hydrocarbon group that may be branched and that may be substituted with a halogen atom, and $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);

(xi) —$(CH_2)_n$—$OR^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);

(xii) —$(CH_2)_n$—S—$R^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12);

(xiii) —$(CH_2)_n$—SO—$R^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12); and (xiv) —$(CH_2)_n$—$SO_2$—$R^{12}$ (where $R^{12}$ is a group selected from the group consisting of:
(1) a hydrogen atom;
(2) a $C_1$ to $C_4$ alkyl group that may be branched and that may be substituted with a halogen atom;
(3) an aryl group, wherein the aryl group may be substituted with at least one group selected from the group (Q); and
(4) a heteroaryl group, wherein the heteroaryl group may be substituted with at least one group selected from the group (Q), and n is an integer from 1 to 12); or $R^7$ and $R^8$ are taken together to form a (divalent organic) group selected from the group consisting of:

—$(CH_2)_m$ (where m is an integer from 2 to 8);

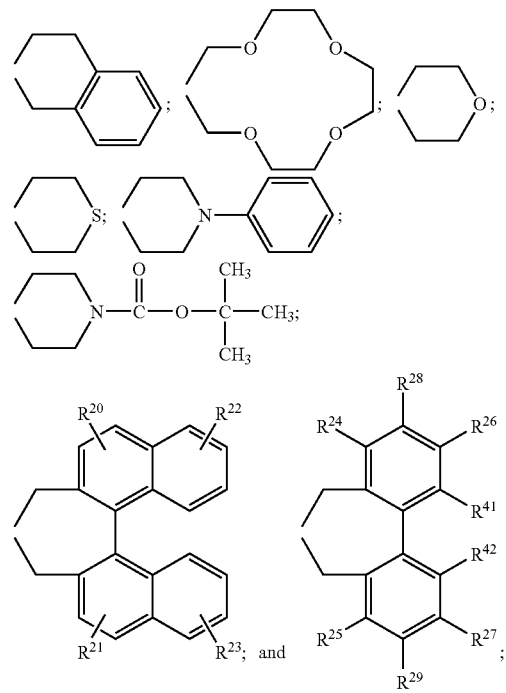

(wherein $R^{20}$, $R^{21}$, $R^{22}$, $R^{23}$, $R^{24}$, $R^{25}$, $R^{26}$, $R^{27}$, $R^{28}$, $R^{29}$, $R^{41}$, and $R^{42}$ are groups independently selected from the group consisting of:

a hydrogen atom;

a $C_1$ to $C_8$ alkyl group that may be branched or form a cyclic group, and/or that may be substituted with a halogen atom;

a $C_2$ to $C_8$ alkenyl group that may be branched or form a cyclic group, and/or that may be substituted with a halogen atom;

a $C_2$ to $C_8$ alkynyl group that may be branched or form a cyclic group, and/or that may be substituted with a halogen atom;

an aryl group, which may be substituted with a $C_1$ to $C_4$ alkyl group that may be substituted with a halogen atom, a $C_1$ to $C_3$ alkoxy group that may be substituted with a halogen atom, an aryl group that may be substituted with a $C_1$ to $C_4$ alkyl group that may be substituted with a halogen atom, a cyano group, a halogen atom, a nitro group, —NR$^{30}$R$^{31}$ (where R$^{30}$ and R$^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetoaryl group, which may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —NR$^{30}$R$^{31}$ (where R$^{30}$ and R$^{31}$ are each independently a hydrogen atom or a $C_1$ to $C_4$ alkyl group that may be substituted with a halogen atom), or a cyclic amino group that is formed by a $C_2$ to $C_8$ alkylene group;

an aralkyl group, which has an aryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —NR$^{30}$R$^{31}$ (where R$^{30}$ and R$^{31}$ are each independently a hydrogen atom or a $C_1$ to $C_4$ alkyl group that may be substituted with a halogen atom), or a cyclic amino group that is formed by a $C_2$ to $C_8$ alkylene group;

a hetoaralkyl group, which has a hetoaryl moiety that may be substituted with a $C_1$ to $C_4$ alkyl group that may be substituted with a halogen atom, a $C_1$ to $C_3$ alkoxy group that may be substituted with a halogen atom, a cyano group, a halogen atom, a nitro group, —NR$^{30}$R$^{31}$ (where R$^{30}$ and R$^{31}$ are each independently a hydrogen atom or a $C_1$ to $C_4$ alkyl group that may be substituted with a halogen atom), or a cyclic amino group that is formed by a $C_2$ to $C_8$ alkylene group;

a ($C_1$ to $C_3$ alkoxy)carbonyl group;

a carbamoyl group;

an N—($C_1$ to $C_4$ alkyl)carbamoyl group; and an N,N-di($C_1$ to $C_4$ alkyl)carbamoyl group (where the $C_1$ to $C_4$ alkyl groups may be the same or different)).

In the present invention, all of R$^1$, R$^{1'}$, R$^2$, R$^{2'}$ R$^3$, and R$^{3'}$ of the compound represented by the formula (II) are preferably $C_1$ to $C_5$ alkoxy groups that may be branched or form a cyclic group and that may be substituted with a halogen atom. In consideration of the availability and ease of preparation, it is preferable that all of R$^1$, R$^{1'}$, R$^2$, R$^{2'}$, R$^3$, and R$^{3'}$ of the compound represented by the formula (II) are a methoxy group, a ethoxy group, or a benzyloxy group.

Alternatively, in the present invention, it is also preferable that R$^4$ and R$^{4'}$ of the compound represented by the formula (II) are each independently selected from the group consisting of:

a hydrogen atom, and an aryl group, wherein the aryl group may be substituted with at least one group selected from the group (Q). In particular, it is preferable that R$^4$ and R$^{4'}$ of the compound represented by the formula (II) are a 3,4,5-trifluorophenyl group or a 3,5-bis(trifluoromethyl)phenyl group.

Alternatively, in the present invention, R$^7$ and R$^8$ of the compound represented by the formula (II) are preferably each independently a $C_1$ to $C_{12}$ alkyl group that may be branched or form a cyclic group and that may be substituted with a halogen atom. In particular, it is preferable that R$^7$ and R$^8$ of the compound represented by the formula (II) are both n-butyl groups.

Alternatively, in the present invention, it is preferable that R$^1$ and R$^{1'}$ of the compound represented by the formula (II) are the same.

Alternatively, in the present invention, it is preferable that R$^2$ and R$^{2'}$ of the compound represented by the formula (II) are the same.

Alternatively, in the present invention, it is preferable that R$^3$ and R$^{3'}$ of the compound represented by the formula (II) are the same.

Alternatively, in the present invention, it is preferable that R$^4$ and R$^{4'}$ of the compound represented by the formula (II) are the same.

Alternatively, in the present invention, it is preferable that R$^7$ and R$^8$ of the compound represented by the formula (II) are the same.

The compound of the formula (II) that is used in the present invention can be synthesized using, for example, a first method, a second method, or a third method described below.

As a first method, the compound represented by the formula (VII) below:

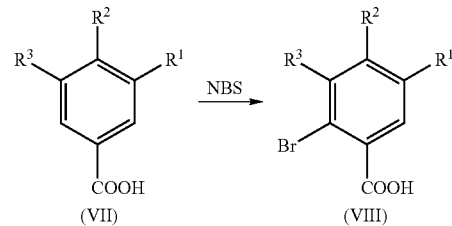

(where R$^1$, R$^2$, and R$^3$ are each independently the same group as defined above) is first dissolved in an organic solvent (such as acetonitrile or chloroform), and then N-bromosuccinimide (NBS) or bromine, for example, is added to this solution and heated under reflux. Thus, the compound of the formula (VIII) that has been bromated at position 2 can be obtained. It should be noted that a specific example of the compound of the formula (VII) is 3,4,5-trimethoxy benzoic acid. This is commercially available from Aldrich, for example.

The compound of the formula (VIII) obtained above is next converted to an acid chloride by reacting it with (i) SOCl$_2$, for example, and then reacted with (ii) (S)— or (R)-1,1'-bi-2-naphthol in a solvent such as THF to give the compound of the formula (IX). It should be noted that in this reaction, by using either (S)-1,1'-bi-2-naphthol or (R)-1,1'-bi-2-naphthol, it is possible to easily establish the absolute configuration (S-form or R-form) of the compound of the formula (II) according to the procedures discussed later.

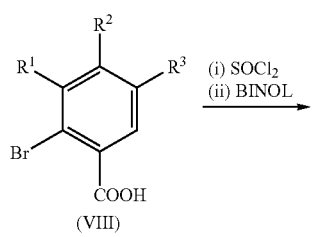

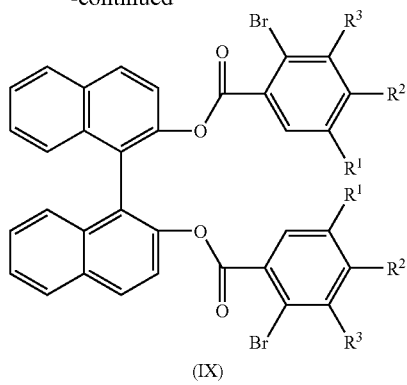

(IX)

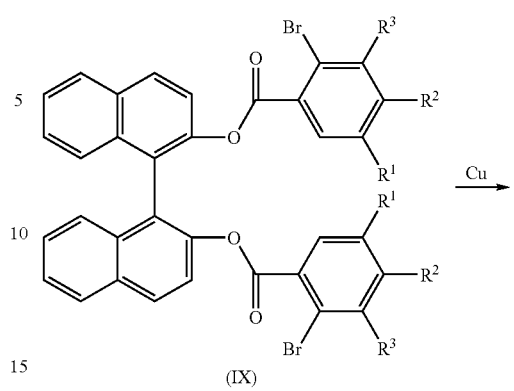

(IX)

While an example was described above in which one compound represented by the formula (VIII) was used, but it should be noted that the present invention is not limited thereto. By using a compound of the formula (VIII) and a different compound also represented by the formula (VIII) (that is, a compound that is represented by the formula (VIII) and that has $R^{1'}$ ($\neq R^1$) instead of $R^1$, $R^{2'}$ ($\neq R^2$) instead of $R^2$ and/or $R^{3'}$ ($\neq R^3$) instead of $R^3$), the compound represented by the following formula (IX)':

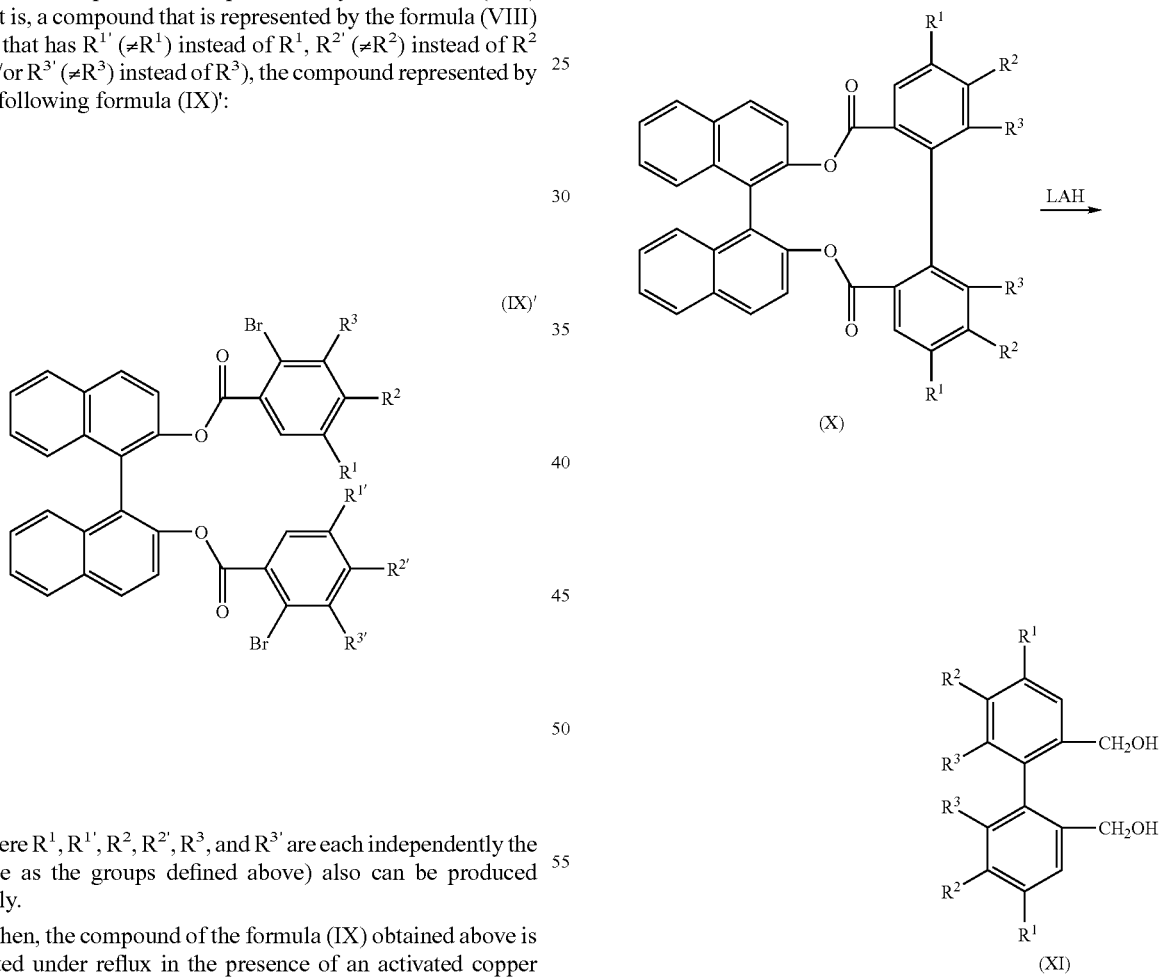

(where $R^1$, $R^{1'}$, $R^2$, $R^{2'}$, $R^3$, and $R^{3'}$ are each independently the same as the groups defined above) also can be produced easily.

Then, the compound of the formula (IX) obtained above is heated under reflux in the presence of an activated copper powder suspended in an organic solvent (such as DMF), so that it can be converted to the compound represented by the formula (X), an intermolecularly coupled product. The compound represented by the formula (X) is added to a THF suspension containing lithium aluminum hydride, and the mixture was stirred for a given time to obtain the biphenyldimethanol compound represented by the formula (XI) below.

By reacting the biphenyldimethanol compound represented by the formula (XI) with a halogenating agent, such as phosphorus tribromide (PBr$_3$), it is possible to obtain the compound represented by the formula (XII) (that is, a compound within the scope of the formula (II), in which both $R^4$ and $R^{4'}$ are hydrogen atoms).

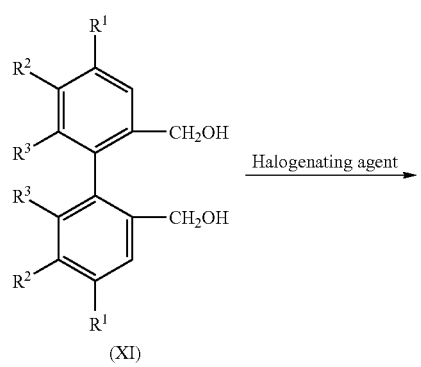

(XI)

Halogenating agent →

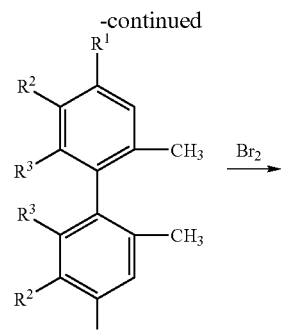

(XIII)

Br₂ →

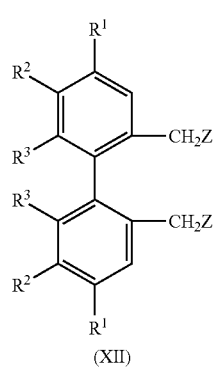

(XII)

(where Z is a halogen atom)

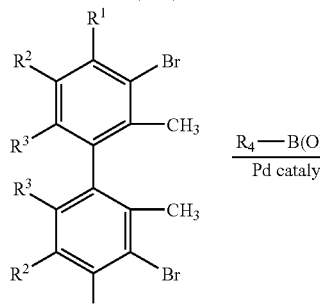

(XIV)

R₄—B(OH)₂
Pd catalyst →

In the present invention, if it is desirable to obtain a compound represented by the formula (II) in which both $R^4$ and $R^{4'}$ are hydrogen atoms, then the compound of the formula (XII) can be used as is. On the other hand, if it is desirable to obtain a compound represented by the formula (II) in which $R^4$ and $R^{4'}$ are groups other than a hydrogen atom, then it is possible to produce such a compound of the formula (II) according to the Reaction Scheme 1 shown below. It should be noted that for the sake of simplicity, a case in which $R^4$ and $R^{4'}$ are the same is described.

<Reactuib Scheme 1>

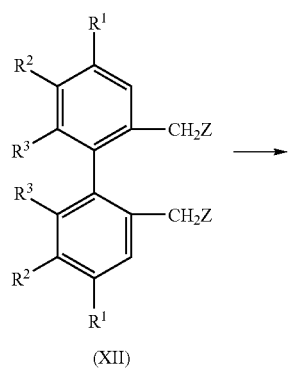

(XII)

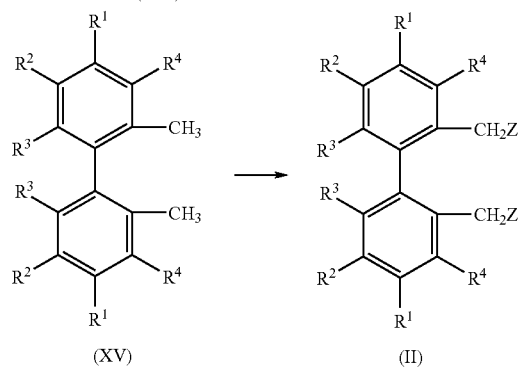

(XV)　　(II)

Referring to the above Reaction Scheme 1, the obtained compound represented by the formula (XII) is dehalogenated by means used ordinarily in the art to give the compound of the formula (XIII). Then, the compound represented by the formula (XIII) is dissolved in an organic solvent, such as pyridine, and then bromine is added thereto to access to the compound represented by the formula (XIV) that is brominated at positions 3 and 3'.

The compound of the formula (XIV) is then subjected to the Suzuki-Miyaura coupling reaction with at least one type of boronic acid derivative represented by $R^4$—B(OH)₂ or $R^{4'}$—B(OH)₂ (where $R^4$ and $R^{4'}$ are each independently the same group as defined above) in an organic solvent, such as THF, and in the presence of a palladium catalyst. A specific example of the boronic acid derivative is 3,4,5-trifluorophenylboronic acid. Thus, the compound of the formula (XV), in which the bromine atoms at positions 3 and 3' are substituted with an $R^4$ group or an $R^{4'}$ group, is produced.

The compound of the formula (XV) thus obtained is finally halogenated by means used ordinarily in the art, so that it is possible to produce the compound represented by the formula (II), in which $R^4$ (and/or $R^{4'}$) is a group other than a hydrogen atom.

Next, a second method for synthesizing the compound of the formula (II) used in the present invention is described.

The second method uses commercially available ellagic acid as a starting material. It is also possible to obtain an optically active form of the dicarboxylic acid compound represented by the following formula (XVI):

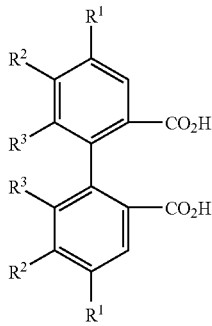

(XVI)

(where $R^1$, $R^2$ and $R^3$ are the same groups as defined above) by the method of O. T. Schmidt et al. (O. T. Schmidt. K. Demmler, Justus Liebigs (1952). *Ann. Chem.* 576:85) using the starting material. Alternatively, it is also possible to obtain the compound represented by the formula (XVI) by treating the compound represented by the formula (X) with a basic aqueous solution. According to these procedures, it is possible to produce selectively either S or R form of the compound represented by the formula (XVI). The compound of the formula (II) is then produced according to the Reaction Scheme 2 as shown below. It should be noted that for the sake of simplicity, a case in which $R^4$ and $R^{4'}$ are the same is described.

<Reaction Scheme 2>

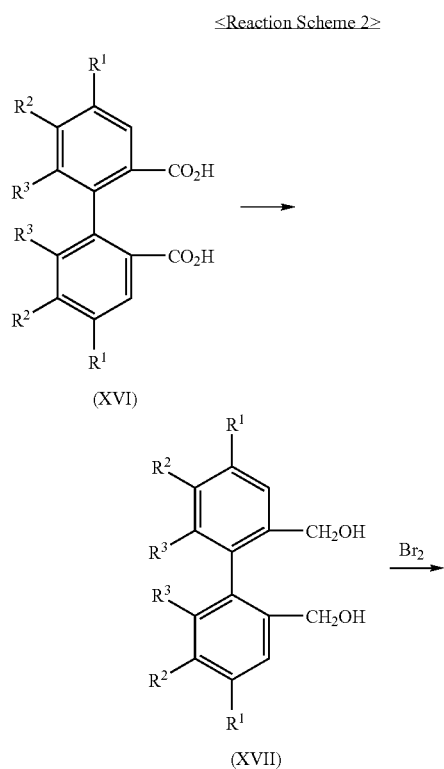

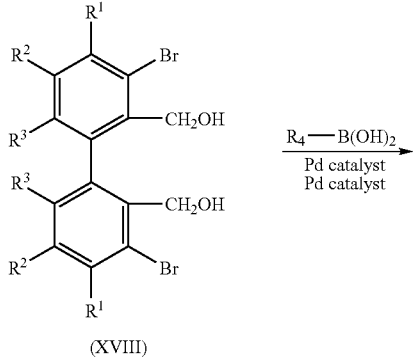

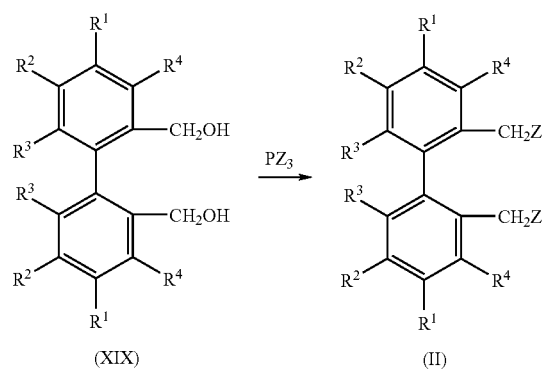

Referring to the above Reaction Scheme 2, the dicarboxylic acid moiety of the obtained compound of the formula (XVI) is converted to dimethanol (the compound represented by the formula (XVII)) using $BH_3 \cdot Me_2S$ in an organic solvent such as THF. Next, the compound of the formula (XVII) is reacted with bromine in an organic solvent, such as pyridine, to produce the compound of the formula (XVIII) that is brominated at positions 3 and 3'.

The compound of the formula (XVIII) is then subjected to the Suzuki-Miyaura coupling reaction with at least one type of boronic acid derivative represented by $R^4$—$B(OH)_2$ or $R^{4'}$—$B(OH)_2$ (where $R^4$ and $R^{4'}$ are each independently the same group as defined above) in an organic solvent, such as THF, and in the presence of a palladium catalyst. A specific example of this boronic acid derivative is 3,4,5-trifluorophenylboronic acid. Thus, the compound of the formula (XIX) in which the bromine atoms at positions 3 and 3' are substituted with the $R^4$ group or the $R^{4'}$ group is produced.

The compound of the formula (XIX) thus obtained is finally reacted with a halogenating agent such as phosphorus tribromide ($PBr_3$), so that it is possible to convert this compound to the compound represented by the formula (II), in which $R^4$ (and/or $R^{4'}$) is a group other than a hydrogen atom.

Next, a third method for synthesizing the compound of the formula (II) used in the present invention is described.

The third method, like the second method, uses the optically active form of the dicarboxylic acid compound represented by the following formula:

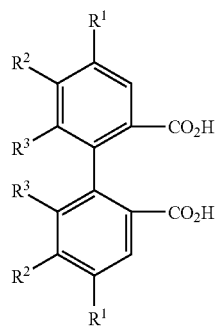

(XVI)

(where $R^1$, $R^2$ and $R^3$ are the same groups as defined above) as a starting material. The compound of the formula (II) is produced according to the Reaction Scheme 3 as shown below. It should be noted that for the sake of simplicity, a case in which $R^4$ and $R^{4'}$ are the same is described.

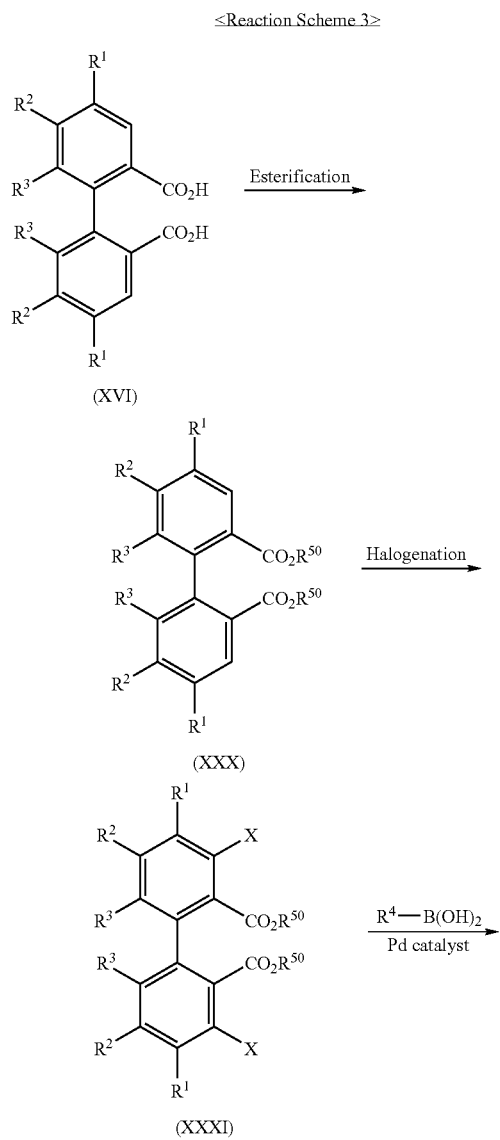

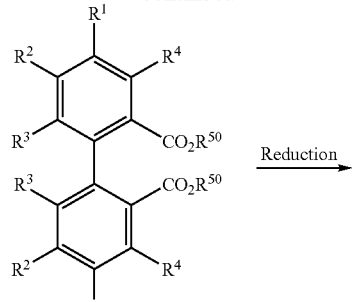

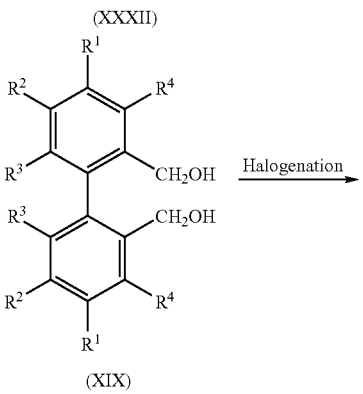

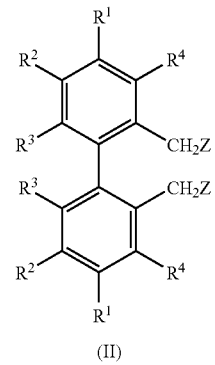

Referring to the above Reaction Scheme 3, the dicarboxylic acid moiety of the compound of the formula (XVI) thus obtained is converted to an ester (the compound represented by the formula (XXX)) by the reaction with an alkyl halide in an organic solvent, such as acetone, and in the presence of an inorganic base. It is also possible to convert the dicarboxylic acid moiety of the obtained compound of the formula (XVI) to an acid chloride by treating with thionyl chloride, which is then converted to an ester (the compound represented by the formula (XXX)) by treating with alcohol in the presence of an organic base, such as pyridine.

Next, the compound of the formula (XXX) is reacted with bromine in an organic solvent, such as acetonitrile, to produce the compound of the formula (XXXI) that is brominated at positions 3 and 3'.

The compound of the formula (XXXI) is then subjected to the Suzuki-Miyaura coupling reaction with at least one type of boronic acid derivative represented by $R^4$—$B(OH)_2$ or $R^{4'}$—$B(OH)_2$ (where $R^4$ and $R^{4'}$ are each independently the same groups as defined above) in an organic solvent such as DME and in the presence of a palladium catalyst. A specific example of this boronic acid derivative is 3,4,5-trifluorophenylboronic acid. Thus, the compound of the formula (XXXII), in which the bromine atoms at positions 3 and 3' have been substituted with an R⁴ group or an R⁴' group, is produced.

The ester moieties of the compound of the formula (XXXII) thus obtained are converted to dimethanols (the compound represented by the formula (XIX)) by reduction with lithium aluminum hydride (LAH) in an organic solvent, such as cyclopentyl methyl ether (CPME).

The compound of the formula (XIX) thus obtained is finally reacted with a halogenating agent, such as phosphorus tribromide (PBr₃), so that it is possible to obtain the compound represented by the formula (II), in which R⁴ (and/or R⁴') is a group other than a hydrogen atom.

Thus, the compound of the formula (II) used in the present invention can be efficiently produced using the first method, the second method, or the third method.

On the other hand, in the method for producing the compounds represented by the formula (I) of the present invention, a large number of the secondary amines of the formula (III) are commercially available and can be obtained easily, which allows facile selection of the appropriate ones.

Examples of the organic solvents used in the reaction process for producing the compound of the formula (I) of the present invention include nitrile solvents (e.g., acetonitrile, propionitrile), ether solvents (e.g., dioxane, tetrahydrofuran, isopropyl ether, diethyl ether, dimethoxyethane, 2-methoxyethyl ether), alcohol solvents (methanol, ethanol, n-propanol, isopropanol, n-butanol, tert-butanol), ester solvents (ethyl acetate, isopropyl acetate), and amide solvents (N,N-dimethylformamide, N,N-dimethylacetamide). In the present invention, acetonitrile is particularly preferable. Examples of acid-scavenging agents include inorganic bases, such as potassium carbonate, sodium carbonate, potassium hydrogencarbonate, and sodium hydrogencarbonate.

In the reaction, the secondary amine of the formula (III) is used preferably in 0.5 to 10 equivalents, and more preferably in 0.8 to 3 equivalents, with respect to the compound of the formula (II). The acid-scavenging agent is preferably used in 0.5 to 10 equivalents, and more preferably in 0.8 to 5 equivalents, with respect to the compound of the formula (II). The reaction between the compound of the formula (II) and the secondary amine of the formula (III) is carried out in an appropriate organic solvent in the presence of the acid-scavenging agent with stirring. The reaction temperature is preferably from room temperature to the boiling point of the organic solvent used, and more preferably the reaction is performed while heating under reflux. The reaction time is preferably 15 minutes to 24 hours, and more preferably 30 minutes to 12 hours. In this case, the organic solvent is preferably used 5 to 50 times, and more preferably 5 to 30 times the amount of the compound of the formula (II) at a volume (mL)/weight (g) ratio with respect to the compound of the formula (II). After the reaction is complete, the reaction mixture is extracted with dichloromethane, dichloroethane, chloroform, or ethyl acetate, and isolation and purification by silica gel column chromatography afforded the compound of the formula (I) can be obtained. Alternatively, the spent reaction mixture may be recycled as it is as a phase-transfer catalyst in the method for producing an α-amino acid derivative, which will be described in detail later.

The compound of the formula (I) thus obtained in which X⁻ is a halide anion is in a pure form with respect to axial asymmetry, and can be used as a phase-transfer catalyst. Here, "pure with respect to axial asymmetry" means that of the stereoisomers based on the axial asymmetry, one specific isomer is more abundant than the other. Preferably, the abundance ratio of the one specific isomer is 90% or more, more preferably 95% or more, and even more preferably 98% or more.

Furthermore, the compound of the formula (I) in which X⁻ is a halide anion can be converted to a compound in which the halide anion is replaced by SCN⁻, HSO₄⁻, HF₂⁻, CF₃SO₃⁻, CH₃-Ph-SO₃⁻, or CH₃SO₃⁻, for example, according to the following processes.

First, a method for producing the compound of the formula (I) in which X⁻ is SCN⁻ or HSO₄⁻ will be described.

The compound of the formula (I) obtained above in which X⁻ is a halide anion is dissolved in, for example, a suitable second organic solvent according to the method described in Japanese Laid-Open Patent Publication No. 2002-173492 and the solution is mixed with a saturated aqueous solution of an alkali metal salt of thiocyanic acid so that the halide anion of X⁻ is converted to SCN⁻.

Examples of the second organic solvent that can be used in this conversion include dichloromethane, chloroform, dichloroethane, tetrahydrofuran, methyl t-butyl ether, diisopropyl ether, and ethyl acetate. Examples of alkali metal salts of thiocyanic acid include potassium thiocyanate and sodium thiocyanate.

For example, by allowing the compound of the formula (I) in which X⁻ is a halide anion to come into contact with an alkali metal salt of thiocyanic acid in a solution under relatively mild conditions such as at room temperature through mixing, the reaction can proceed easily, and the reaction product (that is, the compound of the formula (I) in which X⁻ is SCN⁻) can be obtained in a quantitative yield.

Furthermore, by reacting the compound of the formula (I) in which X⁻ is SCN⁻ with a concentrated sulfuric acid solution, X⁻ can be easily converted from SCN⁻ to HSO₄⁻.

The compound of the formula (I) thus obtained, in which X⁻ is HSO₄⁻, can then be further reacted with an alkali metal fluoride (e.g., potassium fluoride, sodium fluoride or lithium fluoride) to obtain a compound represented by formula (Ia):

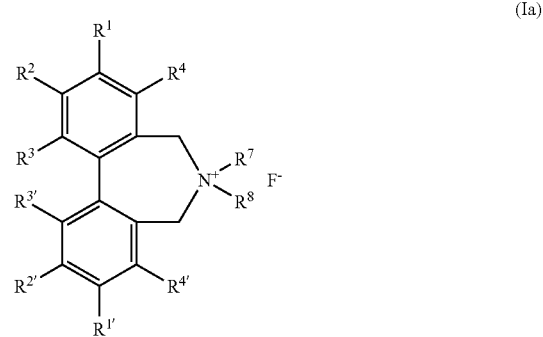

(Ia)

(where R¹, R¹', R², R²', R³, R³', R⁴, R⁴', R⁷, and R⁸ are each independently the same as defined in the formula (I)), which can be used as a catalyst, for example, in a reaction of a silyl enol ether with a carbonyl compound (aldol reaction).

An example of the silyl enol ethers used in the aldol reaction is a trialkylsilyl enol ether. Trialkylsilyl enol ethers can be prepared in advance by reacting a chlorosilane, such as trimethylsilyl chloride and triethylsilyl chloride, with carbonyl compounds (such as ketonic carbonyl derivatives such as 2-butanone, 4-penten-2-one, diethyl ketone, acetophenone, propiophenone, butyronaphtone, cyclohexanone, 1-oxoindan, 1-tetralone or 2-tetralone) in the presence of a base.

In addition to the above-mentioned carbonyl compounds (the above-described ketonic carbonyl derivatives), which serve as precursors of the silyl enol ethers, examples of the carbonyl compounds that can be used to prepare silyl enol ethers for the aldol reaction include aldehyde compounds such as acetylaldehyde, propionaldehyde, butylaldehyde, isobutylaldehyde, isovaleraldehyde, capronaldehyde, dodecylaldehyde, palmitinaldehyde, stearinaldehyde, acrolein, crotonaldehyde, cyclohexanecarbaldehyde, benzaldehyde, anisaldehyde, nicotinaldehyde, cinnamaldehyde, α-naphthaldehyde, and β-naphthaldehyde.

With respect to such a silyl enol ether and such a carbonyl compound, the compound represented by formula (Ia) is used as a catalyst in the aldol reaction to control the stereoselectivity of the reaction.

Next, a method for producing the compound of the formula (I) in which $X^-$ is $HF_2^-$, $CF_3SO_3^-$, $CH_3$-Ph-$SO_3^-$, or $CH_3SO_3^-$ will be described.

The compound of the formula (I) obtained in the above-described manner in which $X^-$ is a halide anion is brought in contact with an ion-exchange resin to produce a first intermediate.

The ion-exchange resin can be freely selected by those skilled in the art. Specific examples of the ion-exchange resin that can be used include Amberlyst A26 (OH) (manufactured by ORGANO CORPORATION).

The compound of the formula (I) in which $X^-$ is a halide anion and the ion-exchange resin can be brought in contact by dissolving the compound of the formula (I) in which $X^-$ is a halide anion in a suitable third solvent and passing this solution through a column filled with the ion-exchange resin. An alcohol solvent is preferable as the third solvent that can be used for such a contact. Specific examples of alcohol solvents include methyl alcohol, ethyl alcohol, isopropyl alcohol, and normal propyl alcohol, although not limited thereto.

There are no particular limitations regarding the amount of the compound of the formula (I) in which $X^-$ is a halide anion and the amount of the third solvent used for such contact, and they can be appropriately set by those skilled in the art.

Thus, the first intermediate is produced.

Next, the first intermediate thus obtained is treated with an acid solution (such as a hydrogen fluoride aqueous solution, a methanesulfonic acid solution, a toluenesulfonic acid solution, or a trifluoromethanesulfonic acid solution) preferably without removing the solvent.

There are no particular limitations regarding the amount of the acid solution used in the present invention. In view of increasing the productivity, it is preferable that the amount is chosen so that an equal or greater amount of hydrogen fluoride or sulfonic acid is reacted with the compound of the formula (I) used above in which $X^-$ is a halide anion. Thus, a compound represented by any of the formulae (Ib) through (Ie):

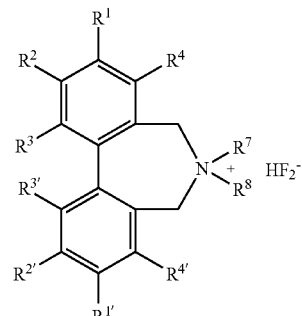
(Ib)

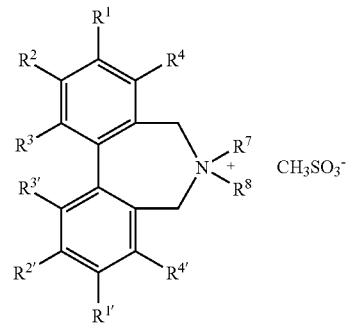
(Ic)

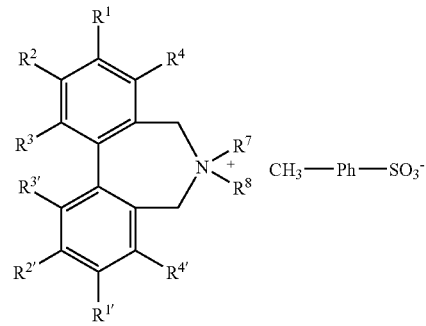
(Id)

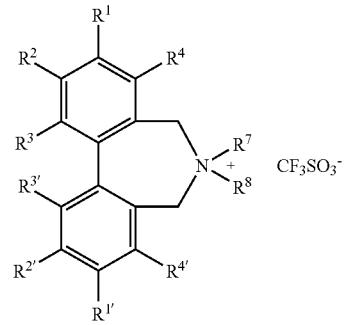
(Ie)

in which the quaternary ammonium moiety is liberated from the first intermediate, and $X^-$ is further converted from a halide anion to $HF_2^-$, $CF_3SO_3^-$, $CH_3$-Ph-$SO_3^-$, or $CH_3SO_3^-$ can be precipitated from the solution.

The compounds of these formulae (Ib) through (Ie) can be easily isolated by removing the solvent using means employed ordinarily by those skilled in the art.

The obtained compounds of the formulae (Ib) through (Ie), and particularly the compound of the formula (Ib), can also be utilized as a catalyst for producing a nitroalcohol diastereo- and enantioselectively.

<Method for Producing α-Amino Acid Derivatives>

Next, a method for producing α-amino acid derivatives using the quaternary ammonium compound of the present invention represented by the formula (I) as a phase-transfer catalyst will be described.

An α-amino acid derivative represented by the formula (VI):

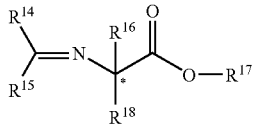

(VI)

(where $R^{14}$ and $R^{15}$ are each independently
(i) a hydrogen atom; or
(ii) an aryl group, wherein the aryl group may be substituted with at least one group selected from the group consisting of:
a $C_1$ to $C_4$ alkyl group that may be branched and that may be substituted with a halogen atom;
a $C_1$ to $C_5$ alkoxy group that may be branched and that may be substituted with a halogen atom;
an aryl group, which may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom);
a cyano group;
—$NR^{30}R^{31}$ (where $R^{30}$ and $R^{31}$ are each independently a hydrogen atom or a $C_1$ to $C_4$ alkyl group that may be substituted with a halogen atom);
a nitro group;
a carbamoyl group;
an N—($C_1$ to $C_4$ alkyl)carbamoyl group;
an N,N-di($C_1$ to $C_4$ alkyl)carbamoyl group;
—$NHCOR^9$ (where $R^9$ is a $C_1$ to $C_4$ alkyl group that may be branched and that may be substituted with a halogen atom); and
a halogen atom; with the proviso that the case where both $R^{14}$ and $R^{15}$ are hydrogen atoms is excluded,
$R^{16}$ is a group selected from the group consisting of:
(i) a hydrogen atom;
(ii) a $C_1$ to $C_{10}$ alkyl group that may be branched or form a cyclic group and that may be substituted with a halogen atom, wherein the alkyl group may be substituted with at least one group selected from the group consisting of:
a $C_1$ to $C_5$ alkoxy group that may be branched and that may be substituted with a halogen atom,
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom),
a halogen atom,
—$COR^9$ (where $R^9$ is a $C_1$ to $C_4$ alkyl group that may be branched and that may be substituted with a halogen atom), and
—$CO_2R^9$ (where $R^9$ is a $C_1$ to $C_4$ alkyl group that may be branched and that may be substituted with a halogen atom);
(iii) a $C_2$ to $C_6$ alkenyl group that may be branched or form a cyclic group and that may be substituted with a halogen atom;
(iv) a $C_2$ to $C_6$ alkynyl group that may be branched or form a cyclic group and that may be substituted with a halogen atom;
(v) an aralkyl group, wherein the aryl moiety of the aralkyl group may be substituted with at least one group selected from the group (Q) consisting of:
a $C_1$ to $C_4$ alkyl group that may be branched and that may be substituted with a halogen atom,
a $C_1$ to $C_5$ alkoxy group that may be branched and that may be substituted with a halogen atom,
an aryl group that may be substituted with a halogen atom, a $C_1$ to $C_4$ alkyl group that may be branched and that may be substituted with a halogen atom, a cyano group, —$NR^{30}R^{31}$ (where $R^{30}$ and $R^{31}$ are each independently a hydrogen atom or a $C_1$ to $C_4$ alkyl group that may be substituted with a halogen atom), an amino group, a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched and that may be substituted with a halogen atom),
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group,
an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom), and
a halogen atom;
(vi) a heteroaralkyl group having a heteroaryl moiety, wherein the heteroaryl moiety may be substituted with at least one group selected from the group (Q);
(vii) an aryl group, wherein the aryl group may be substituted with at least one group selected from the group (Q); and
(viii) a heteroaryl group, wherein the heteroaryl group may be substituted with at least one group selected from the group (Q);
$R^{17}$ is a $C_1$ to $C_8$ alkyl group that may be branched or form a cyclic group, and that may be substituted with a halogen atom;
$R^{18}$ is a group selected from the group consisting of:
(i) a $C_1$ to $C_{10}$ alkyl group that may be branched or form a cyclic group and that may be substituted with a halogen atom, wherein the alkyl group may be substituted with at least one group selected from the group consisting of:
a $C_1$ to $C_5$ alkoxy group that may be branched and that may be substituted with a halogen atom,
a cyano group,
—$NR^{30}R^{31}$ (where $R^{30}$ and $R^{31}$ are each independently a hydrogen atom or a $C_1$ to $C_4$ alkyl group that may be substituted with a halogen atom),
a nitro group,
a carbamoyl group, an N—($C_1$ to $C_4$ alkyl)carbamoyl group,
an N,N-di($C_1$ to $C_4$ alkyl)carbamoyl group,
—$NHCOR^9$ (where $R^9$ is a $C_1$ to $C_4$ alkyl group that may be branched and that may be substituted with a halogen atom),
a halogen atom,
—$COR^9$ (where $R^9$ is a $C_1$ to $C_4$ alkyl group that may be branched and that may be substituted with a halogen atom), and
—$CO_2R^9$ (where $R^9$ is a $C_1$ to $C_4$ alkyl group that may be branched and that may be substituted with a halogen atom);

(ii) a $C_3$ to $C_9$ alkyl group or substituted allyl group that may be branched or form a cyclic group and that may be substituted with a halogen atom;

(iii) a $C_2$ to $C_6$ alkenyl group that may be branched or form a cyclic group and that may be substituted with a halogen atom;

(iv) a $C_2$ to $C_6$ alkynyl group that may be branched or form a cyclic group and that may be substituted with a halogen atom;

(v) an aralkyl group, wherein the aryl moiety of the aralkyl group may be substituted with at least one group selected from the group (Q);

(vi) a heteroaralkyl group having a heteroaryl moiety, wherein the heteroaryl moiety may be substituted with at least one group selected from the group (Q); and (vii) a $C_3$ to $C_8$ propargyl group or substituted propargyl group that may be branched and that may be substituted with a halogen atom; and

* shows a newly created asymmetric center) can be built stereoselectively through the process of alkylating a compound represented by the formula (IV):

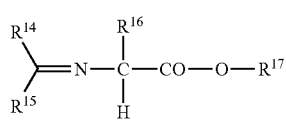

(IV)

(where $R^{14}$, $R^{15}$, $R^{16}$ and $R^{17}$ are the same as those defined in the formula (VI)); with a compound of the formula (V):

(V)

(where $R^{18}$ is the same as defined in the formula (VI), and W is a functional group having a leaving ability)
using the compound represented by the formula (I) as a phase-transfer catalyst in a medium in the presence of an inorganic base.

Examples of the medium used in the alkylation process include benzene, toluene, xylene, diethyl ether, diisopropyl ether, tetrahydrofuran, dioxane, mesitylene, ethyl acetate, isopropyl acetate, cyclopentyl methyl ether, and methyl t-butyl ether. Alternatively, the medium may also be a biphasic one containing water and a medium immiscible with water. The medium can be used in amounts at a ratio of volume (mL)/weight (g) of the compound of the formula (IV), and the ratio is preferably 0.6 to 30, and more preferably 1 to 25.

Examples of the inorganic base used in the alkylation process include lithium hydroxide, sodium hydroxide, potassium hydroxide, calcium hydroxide, rubidium hydroxide, and cesium hydroxide. The inorganic base can be used preferably in 0.5 to 100 equivalents, and more preferably in 0.8 to 40 equivalents, with respect to the compound of the formula (IV).

In the alkylation process, an inorganic base may be used in the form of an aqueous inorganic-base solution. In a case where an inorganic base is used in the form of an aqueous inorganic-base solution, the upper limit of the inorganic base that can be contained in the aqueous inorganic-base solution is preferably 280 equivalents or less, more preferably 150 equivalents or less, and even more preferably 56 equivalents or less, with respect to the compound of the formula (IV). The lower limit of the inorganic base that can be contained in the aqueous inorganic-base solution is preferably 0.5 equivalents or more, more preferably 0.8 equivalents or more, and even more preferably 0.9 equivalents or more, with respect to the compound of the formula (IV). The aqueous inorganic-base solution may be used preferably in 5 w/w % to 70 w/w %, and more preferably in 10 w/w % to 60 w/w %.

The volume ratio between the medium and the aqueous inorganic-base solution is preferably a medium volume (mL)/ inorganic base aqueous medium (mL) ratio of 7/1 to 1/5, more preferably 5/1 to 1/3, and even more preferably 4/1 to 1/1.

In the alkylation process, the compound of the formula (V) is used preferably in 0.5 to 10 equivalents, more preferably in 0.7 to 6 equivalents, and even more preferably in 0.9 to 5 equivalents, with respect to the compound of the formula (IV). The compound of the formula (I) is used as a phase-transfer catalyst preferably in amounts at a lower limit not less than 0.0001 mol % and more preferably not less than 0.0005 mol %, and at an upper limit of preferably not more than 10 mol %, more preferably not more than 2 mol %, even more preferably not more than 1 mol %, and yet even more preferably not more than 0.5 mol %, relative to 1 mol of the compound of the formula (IV). Thus, the phase-transfer catalyst used in the present invention has extremely high activity, and therefore by using the catalyst only in a small amount relative to 1 mol of the compound of the formula (IV), desired optically active α-amino acids and derivatives thereof can be obtained.

In the present invention, in addition to the asymmetrical phase-transfer catalyst represented by the formula (I), an achiral quaternary ammonium salt, such as tetrabutyl ammonium bromide (TBAB), can be also used simultaneously. For example, TBAB functions as a cocatalyst in the reaction system of the present invention to improve the yield of α-amino acids and derivatives thereof, and also allows the amount of the asymmetrical phase-transfer catalyst represented by the formula (I) that is used in the present invention to be further reduced. The amount of TBAB that can be used in the present invention is preferably 0.005 mol % to 1 mol %, and more preferably 0.01 mol % to 0.8 mol % relative to 1 mol of the compound of the formula (IV).

The alkylation process is performed at suitable temperatures between −70° C. and room temperature, preferably between −20° C. and 20° C., in air, under a nitrogen atmosphere, or under an argon atmosphere. This process can be performed with stirring for a suitable period until the alkylation reaction has sufficiently proceeded. The reaction time is preferably 30 min to 48 hours, and more preferably 1 hour to 24 hours.

When the aqueous inorganic-base solution is used in the alkylation process, it is, for example, possible to split the process into multiple operations, as described below.

In other words, at first, the compound of the formula (IV), the phase-transfer catalyst of the formula (I), and the compound of the formula (V) are each added to the medium to prepare a mixture. At this time, it is preferable to sufficiently stir the mixture with cooling using, for example, on ice or ice-salt. To the cooled mixture is then added the aqueous inorganic-base solution to alkylate the compound of the formula (IV). The temperatures set to cool the mixture are preferably between −20° C. and 20° C., more preferably between −15° C. and 15° C., and even more preferably between −10° C. and 10° C.

According to the method of the present invention using the compound of the formula (I) of the present invention as described above, the optically active compound of the formula (VI) can be obtained in a high yield and high optical purity. Here, high optical purity refers to preferably at least 80% ee, more preferably at least 85% ee, yet more preferably at least 90% ee, and even more preferably at least 95% ee.

<Method for Producing α-Amino Acid>

In another aspect of the present invention, a method for producing optically active α-amino acids is provided.

In the present invention, an optically active α-amino acid can be produced by performing, for example, either one of the following procedures, using the optically active compounds of the formula (VI) (optically active α-amino acid derivatives) that are obtained by the method described above.

In the first method, first, the imino group ($R^{14}R^{15}C=N-$) moiety of the optically active compound of the formula (VI) (optically active α-amino acid derivative) that is obtained by the above-described method is first hydrolyzed under acidic conditions (imine acidic-hydrolysis process). Examples of the acid used in the imine acidic-hydrolysis process include inorganic acids (such as hydrochloric acid or phosphoric acid) and organic acids including tribasic acids (such as acetic acid, citric acid, or p-toluenesulfonic acid). More specifically, the imine acidic-hydrolysis process proceeds by treating the compound of the formula (VI) in a suitable medium (e.g., tetrahydrofuran or toluene) at a suitable temperature (e.g., room temperature) using an aqueous solution of the acid. As a result, an ester derivative of amino acid in which the terminal amino group is liberated can be obtained as an imine acidic-hydrolysis product.

Next, if necessary, the ester derivative of amino acid (acidic-hydrolysis product) obtained above is subjected to hydrolysis reaction more acidic than the imine acidic-hydrolysis or that under basic conditions. Thus, a desired amino acid in which the terminal of the acid-hydrolysis product (i.e., the ester group ($-CO_2R^{17}$) in the imine acidic-hydrolysis product) has become a carboxylic acid can be obtained.

Alternatively, in the second method, a process of the opposite order relative to that of the method described above is adopted. That is to say, the ester group ($-CO_2R^{17}$) in the optically active compound of the formula (VI) (optically active α-amino acid derivative) obtained by the alkylation reaction described above is first hydrolyzed under basic conditions (ester basic-hydrolysis process). An aqueous alkali solution, such as aqueous sodium hydroxide solution, can be used in this ester basic-hydrolysis. By such hydrolysis, an ester basic-hydrolysis product in which the terminal of the compound of the formula (VI) (that is, the ester group ($-CO_2R^{17}$) in the compound of the formula (VI)) becomes a carboxylic acid can be obtained.

Next, the imino group ($R^{14}R^{15}C=N-$) moiety of the above-obtained basic-hydrolysis product is hydrolyzed under acidic conditions (imine acidic-hydrolysis process). Examples of the acid used in the imine acidic-hydrolysis process include inorganic acids (e.g., hydrochloric acid, phosphoric acid, sulfuric acid) and organic acids including tribasic acids (e.g., acetic acid, citric acid). More specifically, the imine acidic-hydrolysis process proceeds by treating the ester basic-hydrolysis product in a suitable medium (e.g., tetrahydrofuran or toluene) at a suitable temperature (e.g., room temperature) using an aqueous solution of the acid described above. As a result, a desired amino acid in which the terminal amino group is liberated can be obtained.

In the present invention, in the case where an amino acid is produced from the compound of the formula (VI), either by the first method or the second method may be used, either method can be selected arbitrarily by those skilled in the art according to the specific structure of the amino acid to be actually produced and other relevant production conditions.

Thus, it is possible to produce a desired optically active α-amino acid, efficiently and optionally, without limitations on its structure.

EXAMPLES

Hereinafter, the present invention will be specifically described by way of examples, but is not limited thereto.

In the following examples, unless described otherwise, the measurement was carried out under the following conditions: The $^1$H NMR spectrum was recorded on a JEOL JNM-FX400 (400 MHz) spectrometer and a JMTC-400/54/SS (400 MHz) spectrometer. The optical purity of a reaction product was measured by high-performance liquid chromatography (HPLC) with a Shimadzu 10 instrument or a Waters 2690 instrument using 4.6 mm×25 cm Daicel Chiralcel OD, OD-H, AD or AD-H. The progress of the reaction was monitored using a Merck precoated TLC plate (silica gel 60 GF254, 0.25 mm) for thin layer chromatography (TLC).

Reference Example 1

Synthesis of Starting Material (Compound 2a) for Synthesizing Quaternary Ammonium Salt

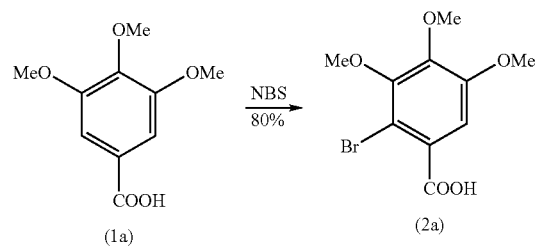

N-Bromosuccinimide (NBS) (21.36 g, 120 mmol) was added to a solution of 3,4,5-trimethoxy benzoic acid (compound 1a) (21.22 g, 100 mmol) in CHCl$_3$ (200 mL). This solution was heated under reflux for 8 hours. Then, the CHCl$_3$ was removed under reduced pressure, and the residue was dissolved in a 1 N NaOH solution (150 mL). After washing with CHCl$_3$ (15 mL) three times, this alkaline solution was acidified with concentrated hydrochloric acid. The resulting precipitates were filtered off, washed with 1 N HCl, and dried to give the title compound 2a (2-bromo-3,4,5-trimethoxybenzoic acid) (23.3 g, 80 mmol/yield: 80%). The NMR spectrum of the obtained compound 2a is shown in Table 1.

TABLE 1

| NMR spectrum of compound 2a |
|---|
| 400 MHz $^1$H NMR (CDCl$_3$) δ 7.40 (1H, s, Ar—H), 3.97 (3H, s, OCH$_3$), 3.91 (3H, s, OCH$_3$), 3.90 (3H, s, OCH$_3$). |

Reference Example 2

Synthesis of Starting Material (Compound 3a) for Synthesizing Quaternary Ammonium Salt

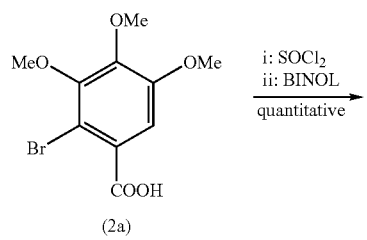

(2a)

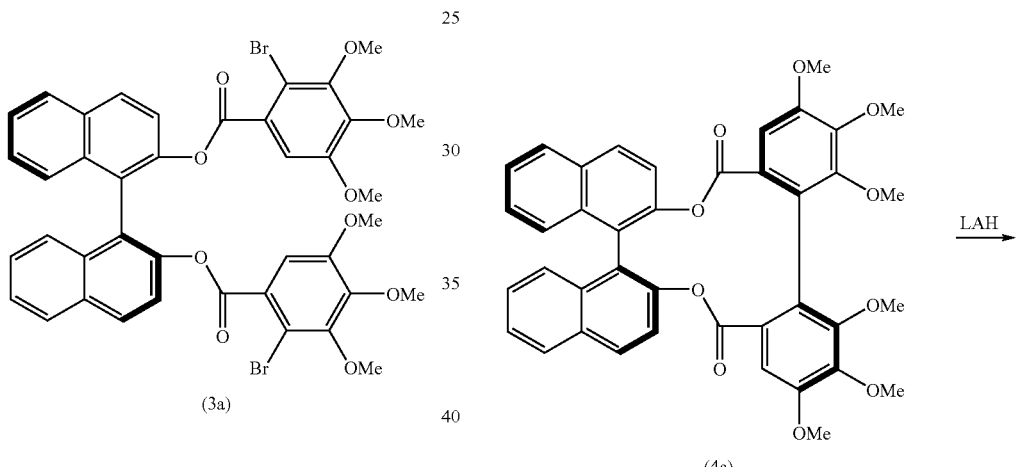

(3a)

Under an argon atmosphere, the compound 2a obtained in Reference Example 1 (2.33 g, 8.0 mmol) and thionyl chloride SOCl₂ (6 mL) were placed in a two-necked flask. This reaction mixture was then heated under reflux for 4 hours. Then, the excess thionyl chloride was evaporated under reduced pressure. THF (15 mL), pyridine (1.5 mL), and (S)-1,1'-bi-2-naphthol (1.14 g, 4.0 mmol) were added to the residue. After reflux for 3 hours, 1 N NaOH followed by 1 N HCl were added to the reaction mixture and extracted with ether. The separated organic layer was dried over Na$_2$SO$_4$ and concentrated. The residue was purified by silica gel chromatography (ether/hexane=1/1 as eluent) to give the title compound 3a ((S)-2,2'-bis(2-bromo-3,4,5-trimethoxybenzoyl)-1,1'-binaphthalene) (3.33 g, 4.0 mmol) in a quantitative yield. The NMR spectrum of the obtained compound 3a is shown in Table 2.

TABLE 2

NMR spectrum of compound 3a

400 MHz $^1$H NMR (CDCl$_3$) δ 8.04 (2H, d, J = 8.8 Hz, Nap-H), 7.94 (2H, d, J = 8.4 Hz, Nap-H), 7.63 (2H, d, J = 8.8 Hz, Nap-H), 7.48 (2H, m, Nap-H), 7.37 (4H, m, Nap-H), 6.31 (2H, s, Ar—H), 3.83 (6H, s, OCH$_3$), 3.73 (6H, s, OCH$_3$), 3.35 (6H, s, OCH$_3$).

Reference Example 3

Synthesis of Starting Material (Compound 5a) for Synthesizing Quaternary Ammonium Salt

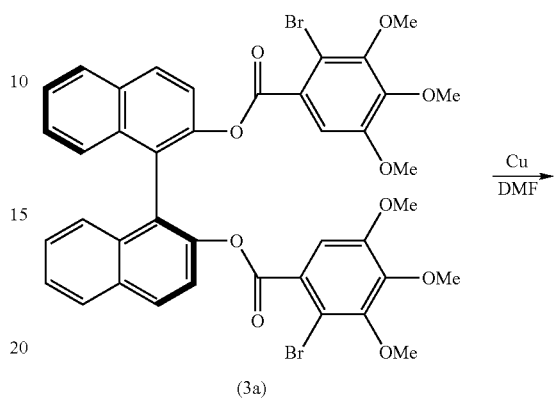

(3a)

(4a)

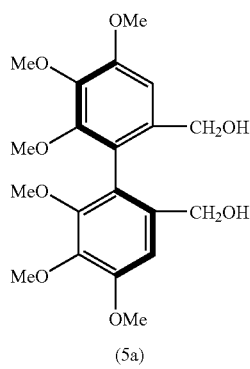

(5a)

50% (with respect to conpound 3a)

A suspension of activated Cu powder (11.8 g, 184 mmol) in DMF (60 mL) was heated to a gentle reflux with vigorously stirring. Then, a solution of the compound 3a (3.33 g, 4.0 mol)

obtained in Reference Example 2 in DMF (50 mL) was added to this mixture over seven hours under an argon atmosphere. After heating at reflux for 12 hours, the reaction mixture was filtered and DMF was removed under reduced pressure. The residue was partially purified by silica gel column chromatography (hexane/ethyl acetate: 2/1 as eluent) to give a mixture of an intramolecular coupling product (compound 4a) and a debrominated byproduct. This was used as is in the following reduction process without further purification.

The compound 4a obtained above (partially purified product) was added dropwise to a suspension of LiAlH$_4$ (0.760 g, 16 mmol) in THF (15 mL) at 0° C. The reaction mixture was stirred at room temperature for 4 hours, carefully treated with 1 N cold HCl, and ethyl acetate was added thereto. The ethyl acetate solution was separated and the solvent was evaporated under reduced pressure. The residue was purified by silica gel column chromatography (ethyl acetate as eluent) to give the title compound 5a ((S)-4,5,6,4',5',6'-hexamethoxybiphenyl-2,2'-dimethanol) (0.790 g, 2.0 mmol/yield: 50%). The NMR spectrum of the obtained compound 5a is shown in Table 3.

TABLE 3

NMR spectrum of compound 5a

400 MHz $^1$H NMR (CDCl$_3$) δ 6.89 (2H, s, Ar—H), 4.19 (4H, s, ArCH$_2$O), 3.94 (6H, s, OCH$_3$), 3.89 (6H, s, OCH$_3$), 3.68 (6H, s, OCH$_3$), 2.91 (2H, s, OH).

The enantiomeric excess was measured by HPLC analysis (Daicel Chiralcel OD, hexane/2-propanol=8:1, flow rate 0.5 mL/min; retention time: (R)-form=23.1 min, (S)-form=35.2 min). The absolute configuration was determined by comparison of the retention times with that of the sample synthesized independently by the known method (*J. Org. Chem.* (2003) 68:9533).

Reference Example 4

Synthesis of Starting Material (Compound 7a) for Synthesizing a Quaternary Ammonium Salt

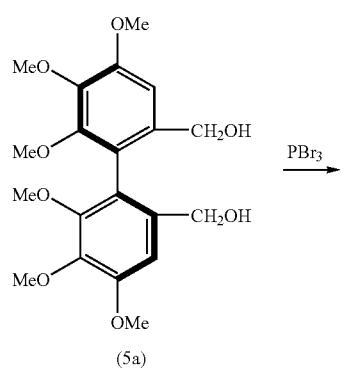

(5a)

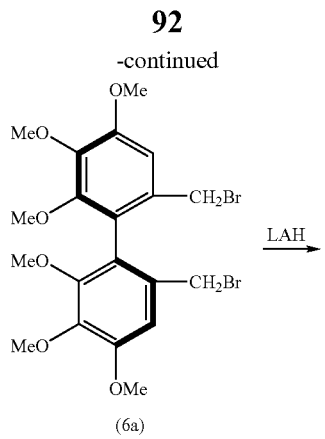

(6a)

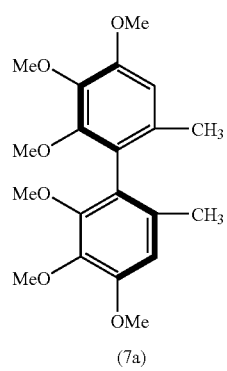

(7a)

(94% with respect to compound 5a)

Phosphorus tribromide (0.380 mL, 4.0 mmol) was added to a solution of compound 5a obtained in Reference Example 3 (0.790 g, 2.0 mmol) in CH$_2$Cl$_2$ (5 mL) at 0° C. The reaction mixture was stirred at room temperature for one hour. Then, water was added thereto, and extracted with ether. The organic layer was washed with saline, dried over Na$_2$SO$_4$, and concentrated to give a compound 6a ((S)-4,5,6,4',5',6'-hexamethoxybiphenyl-2,2'-dimethyl bromide). This was then used in the following reduction process without further purification.

The compound 6a obtained above was added to a suspension of LiAlH$_4$ (0.190 g, 4.0 mmol) in THF (15 mL) at 0° C. The reaction mixture was stirred at room temperature for 4 hours. After 1 N cold HCl was added carefully, the mixture was extracted with ethyl acetate. The solvent was evaporated under reduced pressure, and the residue was purified by silica gel column chromatography (hexane/ethyl acetate=3/1 as eluent) to give the title compound 7a ((S)-4,5,6,4',5',6'-hexamethoxybiphenyl-2,2'-dimethane) (0.690 g, 1.9 mmol/yield: 94%). The NMR spectrum of the obtained compound 7a is shown in Table 4.

TABLE 4

NMR spectrum of compound 7a

400 MHz $^1$H NMR (CDCl$_3$) δ 6.60 (2H, s, Ar—H), 3.88 (6H, s, OCH$_3$), 3.87 (6H, s, OCH$_3$), 3.68 (6H, s, OCH$_3$), 1.95 (6H, s, ArCH$_3$).

Reference Example 5

Synthesis of Starting Material (Compound 8a) for Synthesizing Quaternary Ammonium Salt

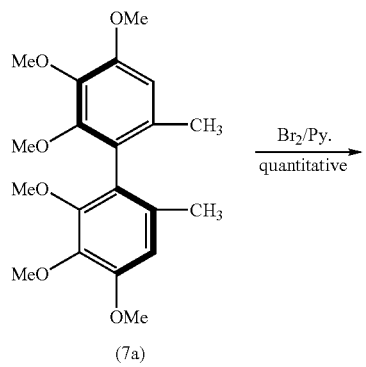

(7a)

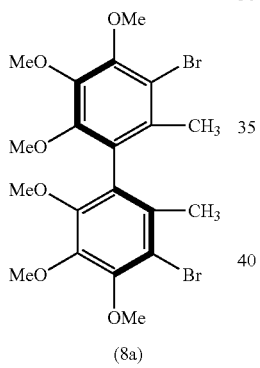

(8a)

To a solution of the compound 7a obtained in Reference Example 4 (0.690 g, 1.88 mmol) and pyridine (0.760 mL, 9.4 mmol) in CHCl$_3$ (5 mL), bromine (0.480 mL, 9.4 mmol) was added dropwise at 0° C. The reaction mixture was stirred for 30 minutes and then poured into a saturated aqueous Na$_2$SO$_3$ solution and extracted with ether. The combined organic layer was washed with 1 N HCl and then concentrated. The residue was purified by silica gel column chromatography a (hexane/ethyl acetate=3/1 as eluent) to give the title compound 8a ((S)-3,3'-dibromo-4,5,6,4',5',6'-hexamethoxybiphenyl-2,2'-dimethane) (0.980 g, 1.88 mmol) in a quantitative yield. The NMR spectrum of the obtained compound 8a is shown in Table 5.

TABLE 5

NMR spectrum of compound 8a

400 MHz $^1$H NMR (CDCl$_3$) δ 3.96 (6H, s, OCH$_3$), 3.91 (6H, s, OCH$_3$), 3.65 (6H, s, OCH$_3$), 2.02 (6H, s, ArCH$_3$).

Reference Example 6

Synthesis of Starting Material (Compound 9a) for Synthesizing Quaternary Ammonium Salt

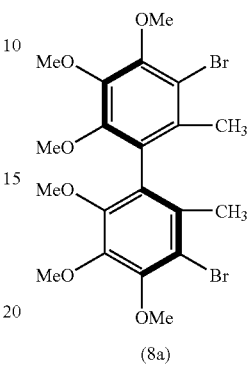

(8a)

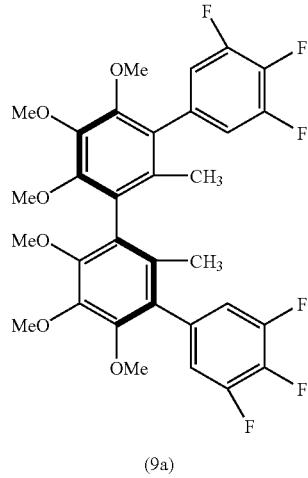

(9a)

A mixture of the compound 8a obtained in Reference Example 5 (0.521 g, 1.0 mmol), 3,4,5-trifluorophenylboronic acid (0.704 g, 4.0 mmol), palladium acetate (0.0449 g, 0.20 mmol), tri-o-tolylphosphine (0.244 g, 0.80 mmol), potassium phosphate n-hydrate (1.69 g, 8.0 mmol), and THF (10 mL) was heated to 75° C. and stirred under an argon atmosphere. The disappearance of the starting material was confirmed by TLC, and then the suspension was filtered and the filtrate was concentrated under reduced pressure. The residue was purified by silica gel column chromatography (hexane/ethyl acetate=5/1 as eluent) to give the title compound 9a ((S)-3,3'-bis(3,4,5-trifluorophenyl)-4,5,6,4',5',6'-hexamethoxybiphenyl-2,2'-dimethane) (0.560 g, 0.90 mmol/yield: 90%). The NMR spectrum of the obtained compound 9a is shown in Table 6.

TABLE 6

NMR spectrum of compound 9a

400 MHz $^1$H NMR (CDCl$_3$): δ 6.88 (4H, m, Ar—H), 3.92 (6H, s, OCH$_3$), 3.74 (6H, s, OCH$_3$), 3.71 (6H, s, OCH$_3$), 1.67 (6H, s, ArCH$_3$).

Reference Example 7

Synthesis of Starting Material (Compound 10a) for Synthesizing Quaternary Ammonium Salt

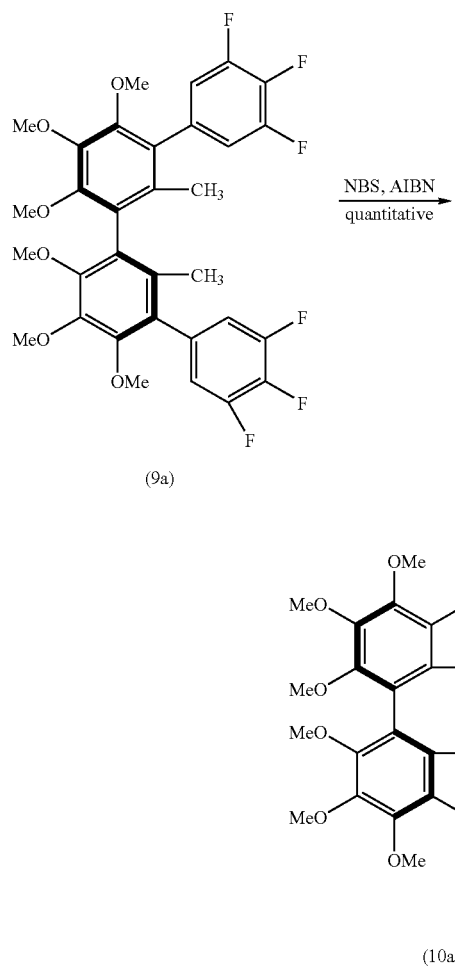

(9a)

(10a)

A solution of the compound 9a obtained in Reference Example 6 (0.560 g, 0.90 mmol), N-bromosuccinimide (0.352 g, 1.98 mmol), and 2,2'-azobisisobutyronitrile (AIBN; 0.0148 g, 0.09 mmol) in benzene (5 mL) was heated at 80° C. for four hours. A saturated aqueous $Na_2SO_3$ solution was added thereto to quench the reaction, and the mixture was extracted with ether. The organic layer was dried over $Na_2SO_4$, and concentrated under reduced pressure. The residue was purified by silica gel column chromatography (hexane/ethyl acetate=5/1 as eluent) to give the title compound 10a ((S)-3,3'-bis(3,4,5-trifluorophenyl)-4,5,6,4',5',6'-hexamethoxybiphenyl-2,2'-dimethyl bromide) (0.702 g, 0.9 mmol) in a quantitative yield. The NMR spectrum of the obtained compound 10a is show in Table 7.

TABLE 7

NMR spectrum of compound 10a

400 MHz $^1$H NMR (CDCl$_3$) δ 7.08 (2H, s, Ar—H), 7.00 (2H, s, Ar—H), 3.95 (10H, m, OCH$_3$, ArCH$_2$), 3.87 (6H, s, OCH$_3$), 3.73 (6H, s, OCH$_3$).

Example 1

Synthesis of Quaternary Ammonium Salt ((S)-11)

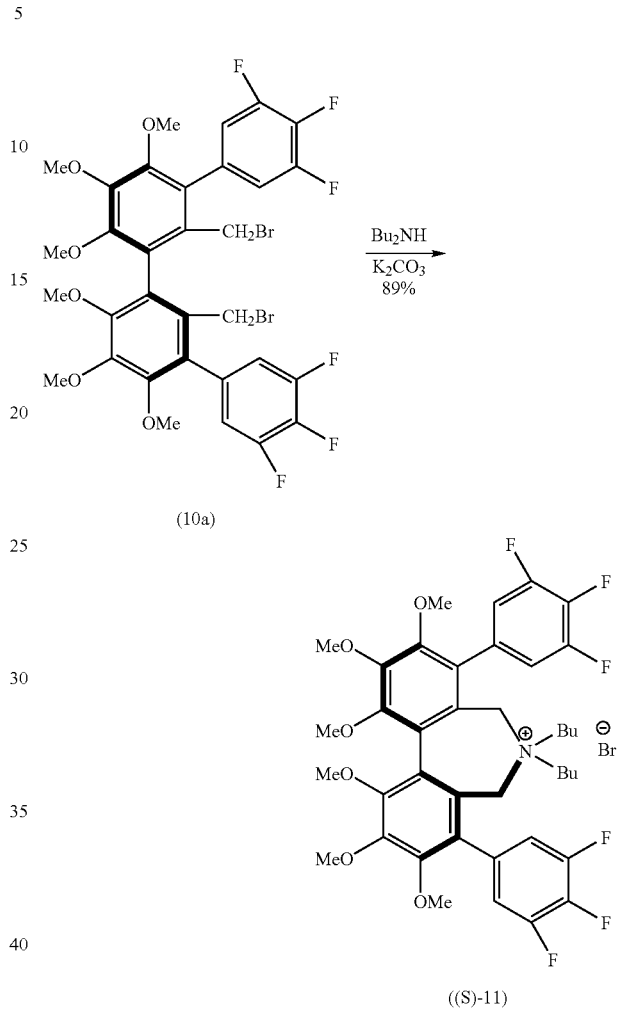

(10a)

((S)-11)

To a suspension of the compound 10a (0.156 g, 0.20 mmol) obtained in Reference Example 7 and potassium carbonate (0.0553 g, 0.40 mmol) in acetonitrile (5 mL), dibutylamine (0.067 mL, 0.40 mmol) was added under an argon atmosphere. This reaction mixture was heated at 80° C. for 10 hours. Then, this was poured into a 1 N HBr aqueous solution and extracted with $CH_2Cl_2$. The organic layer was dried over $Na_2SO_4$ and concentrated under reduced pressure. The residue was purified by silica gel column chromatography (methanol/$CH_2Cl_2$=1/10 as eluent) to give the title optically active quaternary ammonium bromide (compound (S)-11) (in an optically active (S)-form) (0.148 g, 0.178 mmol/yield: 89%). The R-form can also be synthesized using the same procedure as described above. The NMR spectrum of the compound (S)-11 that was obtained in this example is shown in Table 8.

TABLE 8

NMR spectrum of compound (S)-11 obtained in Example 1

400 MHz $^1$H NMR (CDCl$_3$) δ 7.27 (2H, s, Ar—H), 7.08 (2H, s, Ar—H), 4.33 (2H, d, J = 12.8 Hz, ArCH$_2$), 4.04 (6H, s, OCH$_3$), 3.90 (8H, m,

TABLE 8-continued

NMR spectrum of compound (S)-11 obtained in Example 1

OCH$_3$, ArCH$_2$), 3.75 (6H, s, OCH$_3$), 2.97 (2H, m, NCH$_2$), 2.78 (2H, m, NCH$_2$), 1.86 (4H, m, CH$_2$), 1.09 (2H, m, CH$_2$), 0.77 (6H, dd, J = 7.2, 7.2 Hz, CH$_3$), 0.23 (2H, m, CH$_2$).

Reference Example 8

Synthesis of Starting Material (Compound 4b) for Synthesizing Quaternary Ammonium Salt

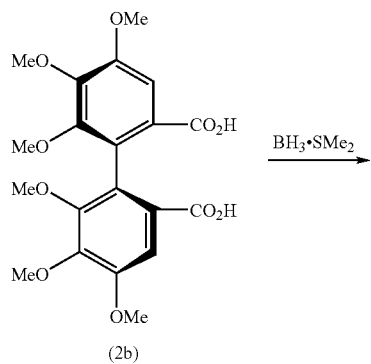

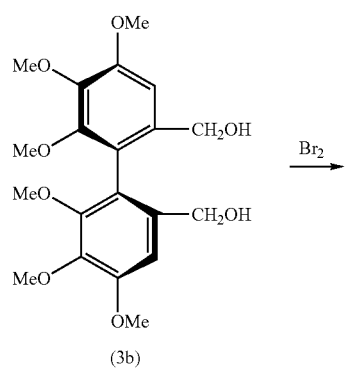

To a THF solution (4 mL) of B(OMe)$_3$ (2 mL) and the (S)-4,5,6,4',5',6'-hexamethoxybiphenyl-2,2'-dicarboxylic acid (2b) (0.422 g, 1.0 mmol) obtained using the method of O. T. Schmidt et al. (O. T. Schmidt, K. Demmler, Justus Liebigs (1952). Ann. Chem. 576:85), a THF solution of BH$_3$.Me$_2$S (4.0 mL, 1.0 M, 4.0 mmol) was added dropwise under an argon atmosphere at 0° C. Then, the reaction temperature was raised to room temperature where the stirring was continued for five hours. Methanol (1 mL) was added thereto slowly to quench the reaction. After removing the solvent by evaporation under reduced pressure, 1 N HCl was added to the residue, and extracted with ethyl acetate. The organic layer was dried over Na$_2$SO$_4$, and concentrated under reduced pressure. The residue was transferred to a solution of pyridine (0.57 mL, 7.0 mmol) in THF (5 mL). This mixture was cooled to −20° C. and then bromine (0.36 mL, 7.0 mmol) was added thereto. Thereafter, the reaction temperature was raised to 0° C. where the stirring was continued for one hour. The reaction mixture was poured into a saturated aqueous Na$_2$SO$_3$ solution, and then extracted with ethyl acetate. The organic layer was dried over Na$_2$SO$_4$, and concentrated under reduced pressure. The residue was purified by silica gel column chromatography (hexane/ethyl acetate=1/1 as eluent) to give the title compound 4b ((S)-3,3'-dibromo-4,5,6,4',5',6'-hexamethoxybiphenyl-2,2'-dimethanol) (524 mg, 0.95 mmol/yield: 95%). The physical property data of the obtained compound 4b is shown in Table 9.

TABLE 9

Physical property data of compound 4b $^1$H NMR (400 MHz, CDCl$_3$) δ 4.56 (2H, d, J = 12.0 Hz, ArCH$_2$), 4.18 (2H, d, J = 12.0 Hz, ArCH$_2$), 3.98 (6H, s, OCH$_3$), 3.94 (6H, s, OCH$_3$), 3.66 (6H, s, OCH$_3$), 3.34 (2H, s, OH);
$^{13}$C NMR (100 MHz, CDCl$_3$) δ 151.15, 150.32, 146.54, 134.10, 126.85, 115.65, 62.08, 60.99, 60.97, 60.62.
IR (neat) 3292, 2939, 1458, 1388, 1313, 1088, 1005 cm$^{-1}$.
HRMS (ESI-TOF) Calculated for C$_{20}$H$_{24}$Br$_2$O$_8$ (Na$^+$): 572.9730, Found: 572.9723.
[α]$_D^{25}$ −7.17° (c 1.00, CHCl$_3$).

Reference Example 9

Synthesis of Starting Material (Compound 5b) for Synthesizing Quaternary Ammonium Salt

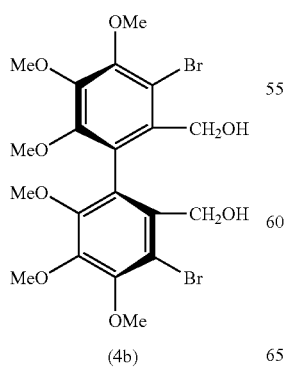

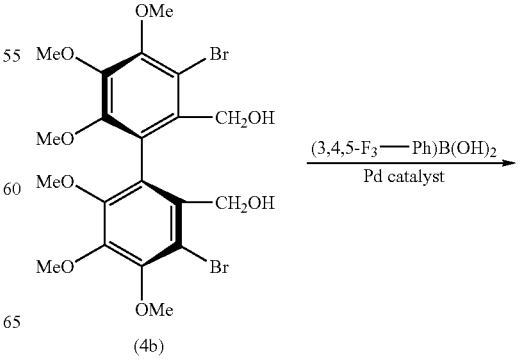

Example 2

Synthesis of Quaternary Ammonium Salt ((S)-11)

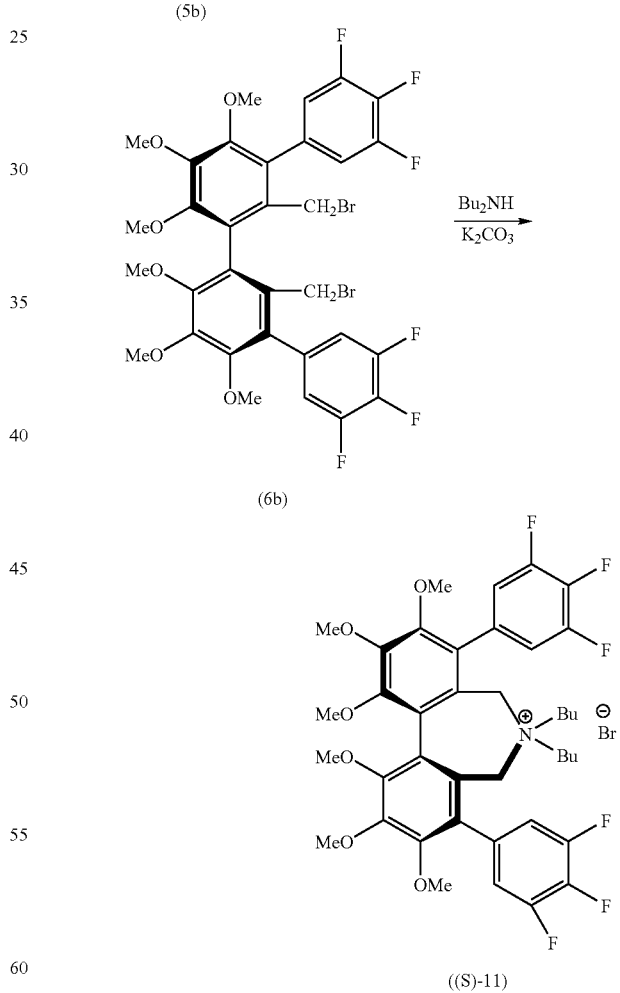

A mixture of the compound 4b obtained in Reference Example 8 (0.276 g, 0.5 mmol), 3,4,5-trifluorophenylboronic acid (0.440 g, 2.5 mmol), palladium acetate (0.0225 g, 0.10 mmol), tri-o-tolylphosphine (0.122 g, 0.40 mmol), potassium phosphate n-hydrate (1.056 g, 5.0 mmol), and THF (5 mL) was heated at 88° C. under an argon atmosphere. The disappearance of the starting material was confirmed by TLC, and then the suspension was filtered. The filtrate was concentrated under reduced pressure. The residue was purified by silica gel column chromatography (hexane/ethyl acetate=2/1 as eluent) to give the title compound 5b ((S)-3,3'-bis(3,4,5-trifluorophenyl)-4,5,6,4',5',6'-hexamethoxybiphenyl-2,2'-dimethanol) (0.255 g, 0.39 mmol/yield: 78%). The physical property data of the obtained compound 5b is shown in Table 10.

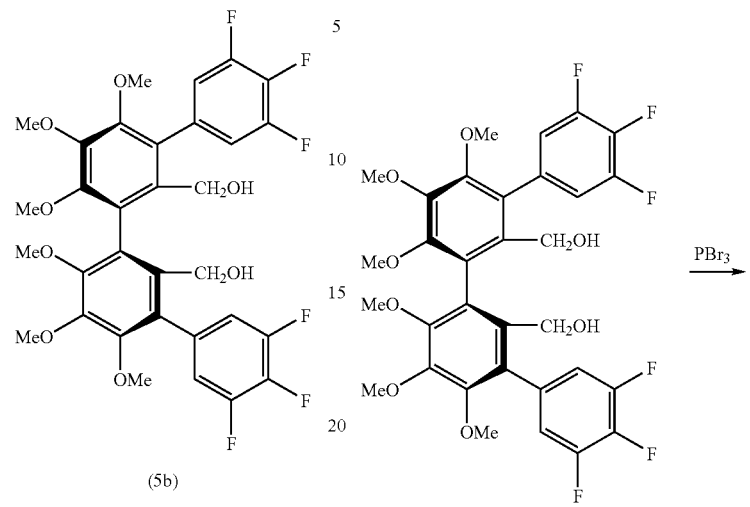

TABLE 10

Physical property data of compound 5b $^1$H NMR (400 MHz, CDCl$_3$) δ 7.09 (4H, m, Ar—H), 3.92-4.02 (10H, m, OCH$_3$, ArCH$_2$), 3.76 (6H, s, OCH$_3$), 3.71 (6H, s, OCH$_3$), 3.19 (2H, s, OH). $^{13}$C NMR (100 MHz, CDCl$_3$) δ 151.11, 150.74, 150.27 (ddd, J$_{C-F}$ = 250.6, 9.9, 4.1 Hz), 138.91 (dt, J$_{C-F}$ = 252.2, 15.7 Hz), 133.11, 131.88 (dt, J$_{C-F}$ = 5.8, 8.2 Hz), 130.26, 126.23, 114.71 (m), 61.03, 60.77, 60.72, 59.60. IR (neat) 3219, 2943, 1530, 1458, 1404, 1308, 1041 cm$^{-1}$. HRMS (ESI-TOF) Calculated for C$_{32}$H$_{28}$F$_6$O$_8$ (Na$^+$): 677.1581, Found: 677.1583.
[α]$_D^{24}$ +43.79° (c 1.00, CHCl$_3$).

Phosphorus tribromide (0.038 mL, 0.4 mmol) was added to a solution of compound 5b obtained in Reference Example 9 (0.131 g, 0.2 mmol) in CH$_2$Cl$_2$ (5 mL) at 0° C. The reaction mixture was stirred at room temperature for one hour. Then, the reaction was quenched with water and extracted with ether. The organic layer was washed with saline, dried over $Na_2SO_4$, and concentrated under reduced pressure to give a crude compound 6b.

Then, the crude compound 6b was transferred to a suspension of potassium carbonate (0.0553 g, 0.40 mmol) and dibutylamine (0.067 mL, 0.40 mmol) in acetonitrile (5 mL) under an argon atmosphere. Then, this mixture was heated at 80° C. for 10 hours. The reaction mixture was then poured into 1 N HBr to quench the reaction, and extracted with $CH_2Cl_2$. The organic layer was dried over $Na_2SO_4$ and concentrated under reduced pressure. The residue was purified by silica gel column chromatography (methanol/$CH_2Cl_2$=1/10 as eluent) to give the title quaternary ammonium bromide of the (compound (S)-11) in an optically active S-form (0.153 g, 0.184 mmol/yield: 92%). The R-form can be synthesized using the same procedure as described above. The physical property data of the compound (S)-11 obtained in this example is shown in Table 11.

TABLE 11

Physical property data of compound (S)-11 obtained in Example 2

$^1$H NMR (400 MHz, $CDCl_3$) δ 7.27 (2H, m, Ar—H), 7.08 (2H, m, Ar—H), 4.33 (2H, d, J = 12.8 Hz, $ArCH_2$), 4.04 (6H, s, $OCH_3$), 3.90 (8H, m, $OCH_3$, $ArCH_2$), 3.75 (6H, s, $OCH_3$), 2.97 (2H, m, $NCH_2$), 2.78 (2H, m, $NCH_2$), 1.86 (4H, m, $CH_2$), 1.09 (2H, m, $CH_2$), 0.77 (6H, dd, J = 7.2, 7.2 Hz, $CH_3$), 0.23 (2H, m, $CH_2$).
$^{13}$C NMR (100 MHz, $CDCl_3$) δ 152.12, 151.75, 150.68 (ddd, $J_{C-F}$ = 253.0, 10.7, 4.1 Hz), 139.28 (dt, $J_{C-F}$ = 255.5, 14.9 Hz), 130.21 (dt, $J_{C-F}$ = 4.9, 7.4 Hz), 129.80, 126.54, 119.98, 115.48 (m), 61.58, 61.14, 60.95, 57.69, 57.15, 24.30, 19.37, 13.28.
IR (neat) 2962, 2943, 1530, 1460, 1400, 1041 (cm$^{-1}$).
HRMS (ESI-TOF) Calculated for $[C_{40}H_{44}F_6NO_6]^+$: 748.3067, Found: 748.3088.
$[α]_D^{24}$ −121.78° (c 1.00, $CHCl_3$).

Example 3

Confirmation of α-Benzylation of Glycine (1)

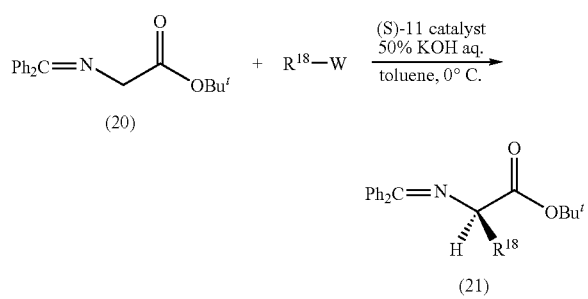

A mixture of the compound (S)-11 obtained in Example 2 (1 mol %; phase-transfer catalyst) and benzyl bromide (1.2 equivalents, 43 μL, 0.36 mmol) as the compound represented by $R^{18}$—W in the above formula was added to a mixture of 50% KOH aqueous solution (1 mL) and a toluene solution (1.5 mL) of N-(biphenylmethylene)glycine tert-butyl ester (compound 20) (88.6 mg, 0.3 mmol), and this was stirred vigorously at 0° C. under an argon atmosphere. Completion of the reaction was confirmed by TLC, and then the reaction mixture was poured into water and extracted with ether. The organic extract was washed with saline and dried over $Na_2SO_4$. The solvent was evaporated under reduced pressure, and then the residual oil was purified by silica gel column chromatography (with ether/hexane=1/10 as the eluent) to give the corresponding compound 21 ((R)-tert-butyl N-(diphenylmethylene) phenylalanine) (110 mg, 0.285 mmol/yield: 95%). The optical purity of the compound 21 obtained in this example was analyzed by HPLC [Daicel Chiralcel OD; eluent: hexane/2-propanol=100:1, flow rate 0.5 mL/min; retention time: (R)-form=14.8 min, (S)-form=28.2 min]. The optical purity of the compound 21 obtained in this example is shown in Table 12 below.

Example 4

Confirmation of α-Benzylation of Glycine (2)

The corresponding compound 21 was obtained in the same manner as in Example 3, except that the reaction temperature was set to 25° C. instead of 0° C., and the reaction time was set to 4.5 hours instead of 6 hours. The optical purity of the compound 21 obtained in this example was also analyzed in the same manner as in Example 3. The optical purity of the compound 21 obtained in this example is shown in Table 12 below.

Example 5

Confirmation of α-Benzylation of Glycine (3)

The corresponding compound 21 was obtained in the same manner as in Example 3, except that the phase-transfer catalyst ((S)-11) was used in 0.1 mol % instead of 1 mol %, the reaction temperature was set to 25° C. instead of 0° C., and the reaction time was set to 11 hours instead of 6 hours. The optical purity of the compound 21 obtained in this example was also analyzed in the same manner as in Example 3. The optical purity of the compound 21 obtained in this example is shown in Table 12 below.

Example 6

Confirmation of α-Benzylation of Glycine (4)

The corresponding compound 21 was obtained in the same manner as in Example 3, except that the phase-transfer catalyst ((S)-11) was used in 0.05 mol % instead of 1 mol %, the reaction temperature was set to 25° C. instead of 0° C., and the reaction time was set to 20 hours instead of 6 hours. The optical purity of the compound 21 obtained in this example also was analyzed in the same manner as in Example 3. The optical purity of the compound 21 obtained in this example is shown in Table 12 below.

Example 7

Confirmation of α-Benzylation of Glycine (5)

The corresponding compound 21 was obtained in the same manner as in Example 3, except that the phase-transfer catalyst ((S)-11) was used in 0.01 mol % instead of 1 mol %, the reaction temperature was set to 25° C. instead of 0° C., and the reaction time was set to 24 hours instead of 6 hours. The optical purity of the compound 21 obtained in this example also was analyzed in the same manner as in Example 3. The optical purity of the compound 21 obtained in this example is shown in Table 12 below.

Example 8

Confirmation of α-Benzylation of Glycine (6)

The corresponding compound 21 was obtained in the same manner as in Example 3, except that the phase-transfer catalyst ((S)-11) was used in 0.5 mol % instead of 1 mol %, allyl bromide was used instead of benzyl bromide as the compound represented by $R^{18}$—W in the above formula in 1.2 equivalents with respect to compound 20, and the reaction time was set to 5 hours instead of 6 hours. The optical purity of the compound 21 obtained in this example also was analyzed in the same manner as in Example 3. The optical purity of the compound 21 obtained in this example is shown in Table 12 below.

Example 9

Confirmation of α-Benzylation of Glycine (7)

The corresponding compound 21 was obtained in the same manner as in Example 3, except that the phase-transfer catalyst ((S)-11) was used in 0.1 mol % instead of 1 mol %, ethyl iodide (8 equivalents, used as the excess quantity) was used instead of benzyl bromide as the compound represented by $R^{18}$—W in the above formula, the reaction temperature was set to 25° C. instead of 0° C., and the reaction time was set to 36 hours instead of 6 hours. The optical purity of the compound 21 obtained in this example also was analyzed in the same manner as in Example 3. The optical purity of the compound 21 obtained in this example is shown in Table 12 below.

TABLE 12

| | Amount of catalyst ((S)-11) used (mol %) | $R^{18}$—W | Reaction condition Temperature (° C.) | Time (hr) | Yield (%) | Product (Compound 21) Optical purity (% ee) | Absolute configuration |
|---|---|---|---|---|---|---|---|
| Example 3 | 1 | PhCH$_2$Br | 0 | 6 | 95 | 98 | R-form |
| Example 4 | 1 | PhCH$_2$Br | 25 | 4.5 | 97 | 97 | R-form |
| Example 5 | 0.1 | PhCH$_2$Br | 25 | 11 | 96 | 97 | R-form |
| Example 6 | 0.05 | PhCH$_2$Br | 25 | 20 | 94 | 97 | R-form |
| Example 7 | 0.01 | PhCH$_2$Br | 25 | 24 | 95 | 96 | R-form |
| Example 8 | 0.5 | CH$_2$=CHCH$_2$Br | 0 | 5 | 99 | 96 | R-form |
| Example 9 | 0.1 | CH$_3$CH$_2$I | 25 | 36 | 80 | 94 | R-form |

As shown in Table 12, it is found that it was possible to produce the corresponding compound 21 in high yield and excellent optical purity under the conditions of any one of Examples 3 through 9. Further, the results of Examples 6 and 7 show that even when the amount of catalyst used is reduced markedly, the yield and the optical purity of the corresponding compound 21 are not significantly different from those in the other examples. From this fact it is clear that use of the phase-transfer catalyst of the present invention (e.g. (S)-11) in a minute amount suffices the efficient production of α-amino acid derivatives. Moreover, with regard to the reaction temperature, as shown in Examples 4 through 7 and 9, it is not necessary to perform the reaction at relatively low temperatures as in Examples 3 and 8, and the reaction proceeds uneventfully at temperatures (such as room temperature) at which industrial production is easier without affecting the yield and the optical purity of the compound 21 so seriously. This demonstrates that the method of the present invention is also extremely beneficial in view of the industrial production.

Example 10

Confirmation of α-Benzylation of Alanine

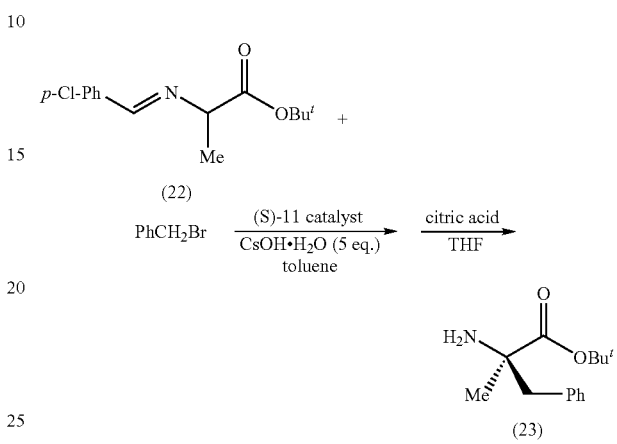

A mixture of a toluene solution (is mL) of tert-butyl ester aldimine Schiff base (22) (80.3 mg, 0.3 mmol), the compound (S)-11 obtained in Example 2 (1 mol %; phase-transfer catalyst), benzyl bromide (43 μL, 0.36 mmol) and CsOH.H$_2$O (252 mg, 1.5 mmol) was stirred vigorously at 0° C. under an argon atmosphere. The progress of the reaction was followed by TLC. After the reaction was complete, the mixture was poured into water and extracted with CH$_2$Cl$_2$. The solvent was evaporated under reduced pressure, and the residue was dissolved in THF (5 mL). A 0.5 M citric acid (5 mL) was added thereto, and the resulting mixture was stirred for one hour at room temperature. THF was evaporated under reduced pressure, and then the aqueous layer was washed with hexane. Then, the aqueous layer was basified with solid Na$_2$CO$_3$, and the mixture was extracted with CH$_2$Cl$_2$. The organic extract was dried over Na$_2$SO$_4$. The solvent was evaporated under reduced pressure, and the residue was purified by silica gel column chromatography (ethyl acetate/hexane=1/2 as eluent) to give the title alkylated compound 23 (37 mg, 0.159 mmol). Since a portion of the compound 23 obtained in this example was volatilized during purification where concentration under reduced pressure, the yield was 53%. The optical purity of the compound 23 obtained in this example was analyzed by HPLC [Daicel Chiralcel AD-H;

eluent: hexane/2-propanol=30/1, flow rate 0.5 mL/min; retention time: (R)-form=12.6 min, (S)-form=19.4 min]. The optical purity of the compound 23 obtained in this example was 99% ee.

Example 11

Alkylation of Alanine Ethyl Ester Using 48% Potassium Hydroxide Aqueous Solution

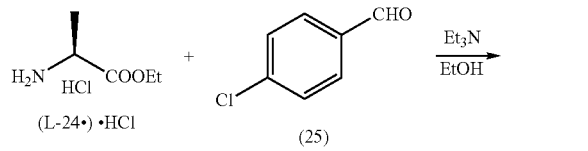

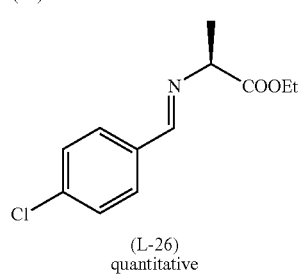

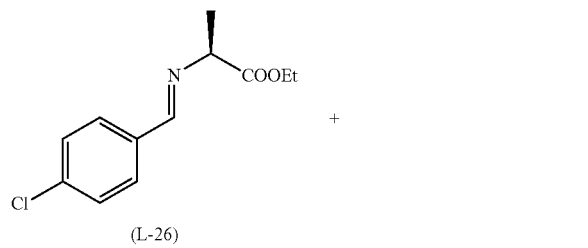

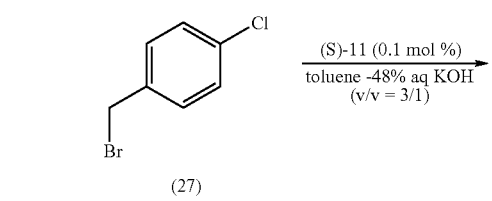

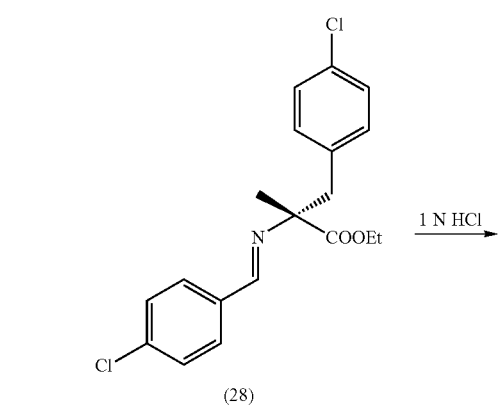

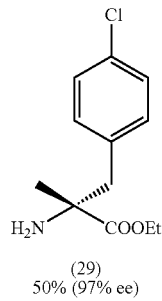

(29)
50% (97% ee)

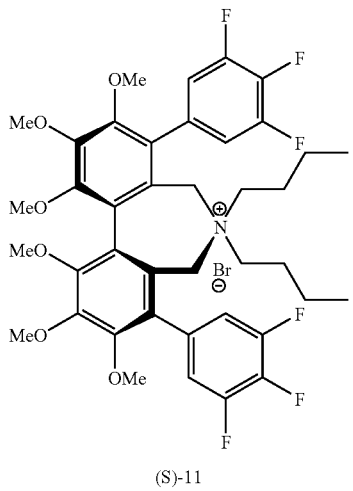

(S)-11

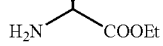

(30)

A hydrochloride salt of L-alanine ethyl ester (compound L-24) (23.0 g, 150 mmol) was added to ethanol (140 mL), and then triethylamine (15.2 g, 150 mmol) was added thereto and stirred. p-Chlorobenzaldehyde (compound 25), which was melted in a bath heated to 60° C. and allowed to cool until room temperature, was added dropwise to the ethanol solution of compound L-24. After stirring at room temperature for two hours, the ethanol was evaporated under reduced pressure. Half-saturated saline (40 mL) was then added thereto, and then extracted with ethyl acetate (160 mL×1). The ethyl acetate layer was washed with saturated saline (20 mL) and filtered through filter paper covered with sodium sulfate. The filtrate was then concentrated under reduced pressure to give L-alanine ethyl ester-p-chlorobenzyl Schiff base (compound L-26) (36.75 g) in a quantitative yield.

Then, the Schiff base obtained above (compound L-26) (1.20 mg, 5.01 mmol), 4-chlorobenzyl bromide (compound 27) (1.23 g, 5.99 mmol), and the compound (S)-11 obtained in Example 2 (0.1 mol %; phase-transfer catalyst) (4.2 mg, 5.1 µmol) were added to toluene (20 mL), and stirred vigorously (1000 rpm) with ice-salt cooling. Once the internal temperature reached −5° C., a 48% potassium hydroxide aqueous solution (8.80 g (as the aqueous solution)) was added to the reaction mixture. This was then stirred for four hours while maintaining the internal temperature between −1° C. and −5° C. The disappearance of the compound 30 due to degradation of the Schiff base (compound L-26) in the toluene layer was monitered by TLC (hexane/ethyl acetate/triethylamine=5/5/0.1, ninhydrin color, Rf value of 0.1 for compound 30), and the end of the reaction was also confirmed by TLC under the same conditions. Then, water (20 mL) was added thereto, and the toluene layer was removed by separation. The aqueous layer was extracted with toluene (20 mL×2). The combined toluene layer was dried over sodium sulfate and concentrated under reduced pressure to give the alkylated Schiff base (compound 28) as an oily residue.

To this residue, 1 N hydrochloric acid (10 mL) was added and stirred at room temperature for two hours. The aqueous layer was washed with toluene (20 mL×3), and sodium bicarbonate was added thereto carefully to avoid too vigorous bubbling until pH of the solution reached not lower than 11 (confirmed by universal pH test paper), and then the mixture was extracted with ethyl acetate (20 mL×3). The ethyl acetate solution obtained was dried over sodium sulfate and concentrated under reduced pressure to give the title compound 29 ((R)-α-methyl-4-chlorophenylalanine ethyl ester) (0.60 g, yield: 50%). The optical purity of the compound 29 obtained in this example was analyzed by HPLC [Daicel Chiralcel AD (4.6 mmϕ×25 cm); eluent: hexane/isopropyl alcohol/diethylamine=99/1/0.1; flow rate 0.5 mL/min; temperature=room temperature; detector UV 267.5 nm; retention time: (R)-form=24.7 min, (S)-form=26.3 min). The optical purity of the compound 29 obtained in this example was 97% ee.

Example 12

Hydrolysis of (R)-α-methyl-4-chlorophenylalanine ethyl ester

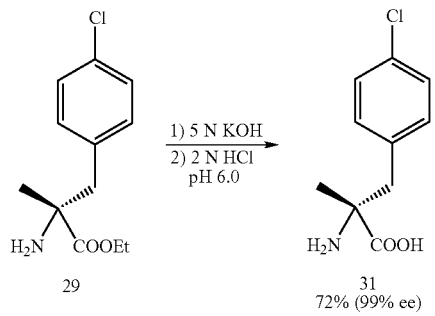 [SMILES: CCOC(=O)[C@@](C)(N)Cc1ccc(Cl)cc1 ; C[C@@](N)(Cc1ccc(Cl)cc1)C(=O)O]

To (R)-α-methyl-4-chlorophenylalanine ethyl ester (compound 29) (0.35 g, 1.4 mmol, optical purity 97% ee), 5 N aqueous potassium hydroxide solution (1 mL) was added, and stirred at room temperature for two hours until the solution became homogeneous. Then, 2 N hydrochloric acid was added thereto until pH of the mixture reached 6.0. White precipitate was observed, and the stirring was continued for 30 minutes with ice-cooling. The white precipitate was filtered off, dried at 50° C. for three hours to give compound 31 ((R)-α-methyl-4-chlorophenylalanine) (0.22 g, yield 72%). The optical purity of the compound 31 obtained in this example was analyzed by HPLC [Sumika Sumichiral OA-5000 (4.6 mmΦ×15 cm); eluent: methanol/2 mM aqueous copper sulfate solution=30/70; flow rate 1.0 mL/min; temperature=37° C.; detector UV 254 nm; retention time: (S)-form=40.4 min, (R)-form=57.2 min]. The optical purity of the compound 31 obtained in this example was 99% ee.

Example 13

Synthesis of Quaternary Ammonium Salt (Compound (S)-40)

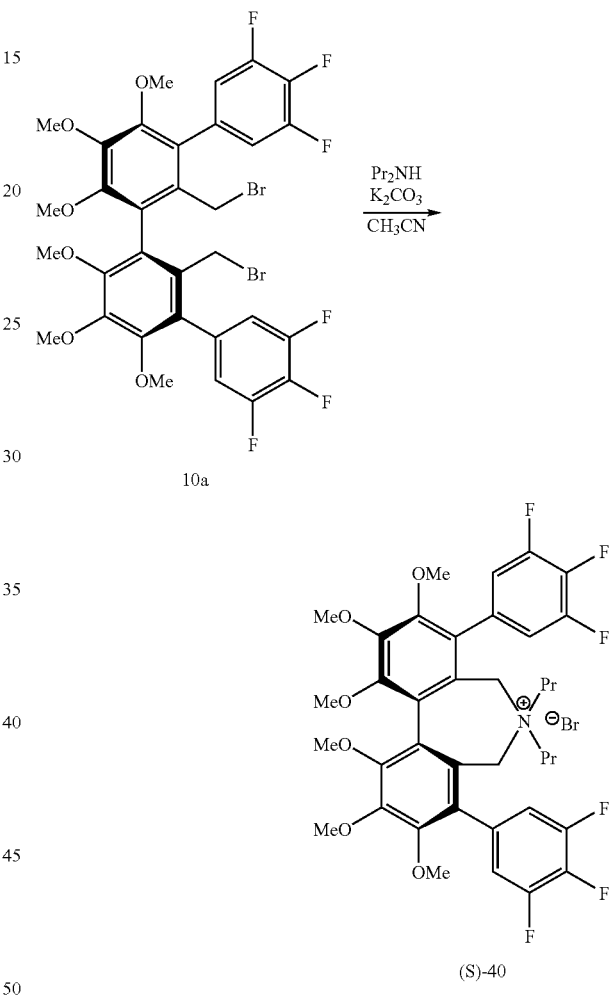

Dipropylamine (0.0137 mL, 0.1 mmol) was added to a suspension of the compound 10a obtained in Reference Example 7 (15.6 mg, 0.02 mmol) and potassium carbonate (6.9 mg, 0.05 mmol) in acetonitrile (3 mL) under an argon atmosphere. This reaction mixture was heated at 80° C. for 10 hours. Then, this was poured into a 1 N HBr aqueous solution and extracted with CH$_2$Cl$_2$. The organic layer was dried over Na$_2$SO$_4$ and concentrated under reduced pressure. The residue was purified by silica gel column chromatography (methanol/CH$_2$Cl$_2$=1/10 as eluent) to give the title optically active quaternary ammonium bromide (compound (S)-40) (S-form) (14.6 mg, 0.018 mmol/yield: 91%). The R-form can also be synthesized using the same procedure as above. The NMR spectrum of the compound (S)-40 obtained in this example is shown in Table 13.

TABLE 13

NMR spectrum of compound (S)-40 obtained in Example 13

400 MHz $^1$H NMR (CDCl$_3$) δ 7.28 (2H, s, Ar—H), 7.09 (2H, s, Ar—H), 4.31 (2H, d, J = 12.4 Hz, ArCH$_2$), 4.04 (6H, s, OCH$_3$), 3.89 (8H, m, OCH$_3$, ArCH$_2$), 3.77 (6H, s, OCH$_3$), 2.95 (2H, m, NCH$_2$), 2.75 (2H, m, NCH$_2$), 1.09 (2H, m, CH$_2$), 0.77 (6H, dd, J = 7.2, 7.2 Hz, CH$_3$), 0.25 (2H, m, CH$_2$).

Example 14

Synthesis of Quaternary Ammonium Salt (Compound (S)-41)

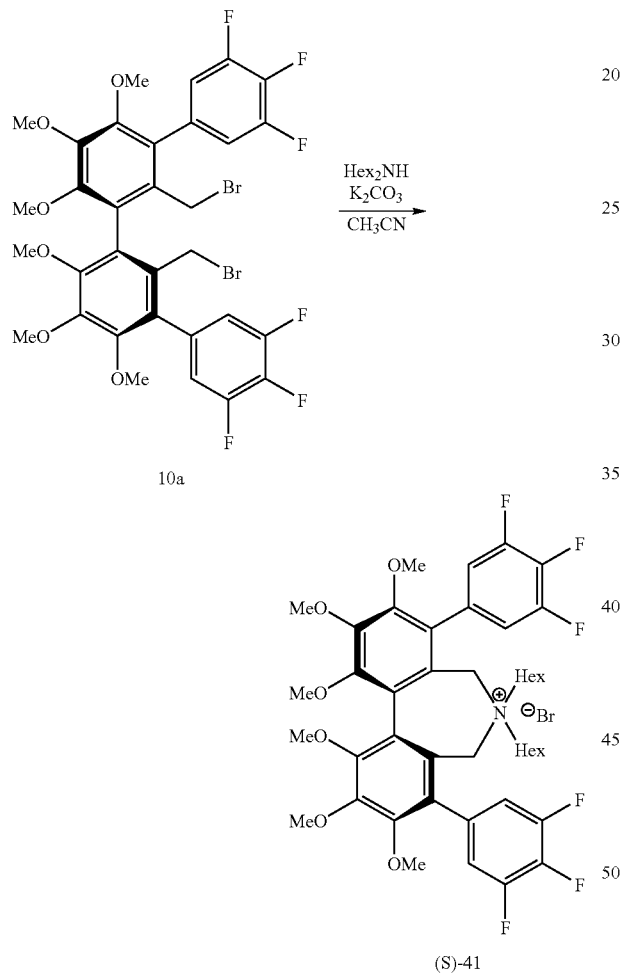

10a (S)-41

Dihexylamine (0.0233 mL, 0.1 mmol) was added to a suspension of the compound 10a obtained in Reference Example 7 (15.6 mg, 0.02 mmol) and potassium carbonate (6.9 mg, 0.05 mmol) in acetonitrile (3 mL) under an argon atmosphere. This reaction mixture was heated at 80° C. for 10 hours. Then, this was poured into a 1 N HBr aqueous solution and extracted with CH$_2$Cl$_2$. The organic layer was dried over Na$_2$SO$_4$ and concentrated under reduced pressure. The residue was purified by silica gel column chromatography (methanol/CH$_2$Cl$_2$=1/20 as eluent) to give the title quaternary ammonium bromide (compound (S)-41) in an optically active S-form (16 mg, 0.018 mmol/yield: 90%). The R-form can also be synthesized using the same procedure as above. The NMR spectrum of the compound (S)-41 obtained in this example is shown in Table 14.

TABLE 14

NMR spectrum of compound (S)-41 obtained in Example 14

400 MHz $^1$H NMR (CDCl$_3$) δ 7.26 (2H, s, Ar—H), 7.07 (2H, s, Ar—H), 4.31 (2H, d, J = 12.5 Hz, ArCH$_2$), 4.05 (6H, s, OCH$_3$), 3.92 (8H, m, OCH$_3$, ArCH$_2$), 3.75 (6H, s, OCH$_3$), 2.92 (2H, m, NCH$_2$), 2.74 (2H, m, NCH$_2$), 1.30-1.08 (14H, m, CH$_2$), 0.74 (6H, dd, J = 7.1, 7.2 Hz, CH$_3$), 0.25 (2H, m, CH$_2$).

Reference Example 10

Synthesis of Starting Material (Compound (R)-43) for Synthesizing Quaternary Ammonium Salt

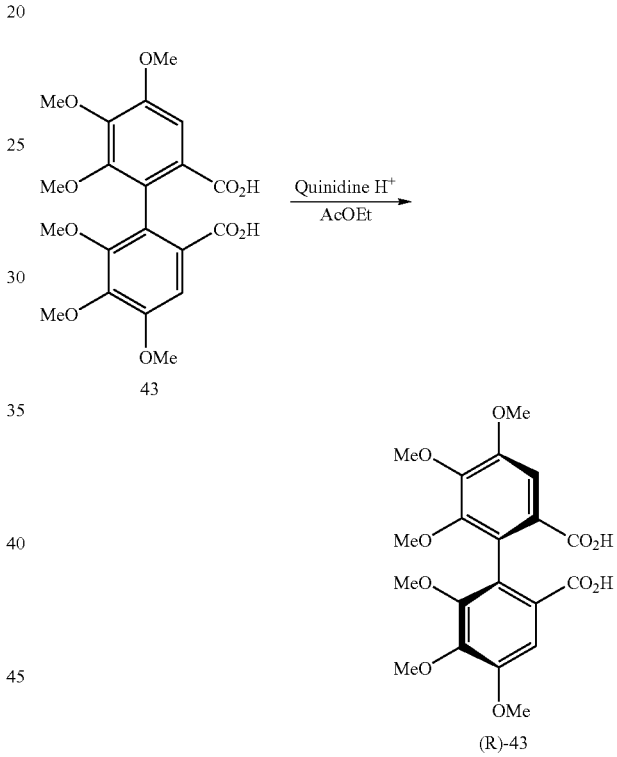

43

(R)-43

Quinidine (16.22 g, 50 mmol) was added to an ethyl acetate solution (160 mL) of the 4,5,6,4',5',6'-hexamethoxydiphenic acid (43) (21.12 g, 50 mmol) obtained using the method of J. D. Reitze et al. (J. D. Reitze, S. R. Przewloka, B. J. Shearer (2001). *Holzforschung* 55:171) at room temperature. The reaction mixture was heated at reflux for one hour and then slowly cooled to 0° C. The precipitated crystal was collected by filtration and washed with ethyl acetate and then dried to give a bisquinidine salt of 4,5,6,4',5',6'-hexamethoxydiphenic acid (15.34 g). Ethyl acetate (50 mL) and 1 N HCl aqueous solution (100 mL) were added, and stirred at room temperature for one hour. This was extracted with ethyl acetate and the extract was dried over Na$_2$SO$_4$ and concentrated to give the title compound (R)-43 ((R)-4,5,6,4',5',6'-hexamethoxydiphenic acid) (5.97 g, 14.1 mmol/yield: 28%).

The filtrate from the above process was concentrated under reduced pressure, and 85% aqueous methanol (82 mL) and 1 N aqueous potassium hydroxide solution (35 mL) were added dropwise to this residue. To this was added quinidine (4.87 g, 15 mmol) at room temperature. The reaction mixture was heated at reflux for one hour, and then cooled slowly to 0° C. The precipitated crystals were filtered off, washed with 85% aqueous methanol and dried to give the bisquinidine salt of the 4,5,6,4',5',6'-hexamethoxydiphenic acid (15.84 g). To this were added ethyl acetate (50 mL) and 1 N HCl aqueous solution (100 mL) were added to this, and stirred at room temperature for one hour. This was extracted with ethyl acetate and dried over $Na_2SO_4$ and concentrated to give the compound (S)-43 ((S)-4,5,6,4',5',6'-hexamethoxydiphenic acid) (4.92 g, 11.65 mmol/yield: 23%).

The enantiomeric excess was measured by HPLC analysis (Daicel Chiralcel AD-H, hexane/2-propanol/TFA=93:7:0.1, flow rate 0.8 mL/min, retention time: (S)-form=26.3 min, (R)-form=34.1 min). The optical purity of the compound (R)-43 was 99% ee. The optical purity of the compound (S)-43 was 99% ee. The absolute configuration was determined by comparison of the retention times with those of the samples synthesized independently by the known method (O. T. Schmidt, K. Demmler, Justus Liebigs (1952). *Ann. Chem.* 576:85).

Reference Example 11

Synthesis of Starting Material (Compound (R)-44) for Synthesizing Quaternary Ammonium Salt

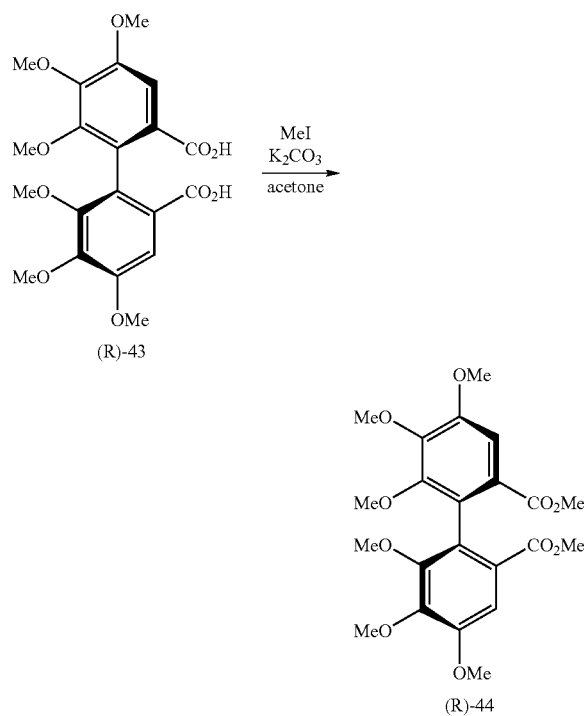

Potassium carbonate (0.55 g, 8 mmol) and methyl iodide (1.25 mL, 20 mmol) were added to a solution of the compound (R)-43 obtained in Reference Example 10 (0.84 g, 2 mmol) in acetone (10 mL). This reaction mixture was heated under reflux for five hours, then saturated $NaHCO_3$ solution was added. The mixture was extracted with ethyl acetate. The organic layer was dried over $Na_2SO_4$ and concentrated under reduced pressure. The title compound (R)-44 ((R)-4,5,6,4',5',6'-hexamethoxydiphenate dimethyl ester) (0.90 g, 2 mmol) was obtained in a quantitative yield. The NMR spectrum of the obtained compound (R)-44 is shown in Table 15.

TABLE 15

| NMR spectrum of compound (R)-44 |
| --- |
| 400 MHz $^1$H NMR (CDCl$_3$) δ 7.37 (2H, s, Ar—H), 3.97 (12H, s, OCH$_3$), 3.94 (6H, s, OCH$_3$), 3.60 (6H, s, CO$_2$CH$_3$). |

Reference Example 12

Synthesis of Starting Material (Compound (R)-45) for Synthesizing Quaternary Ammonium Salt

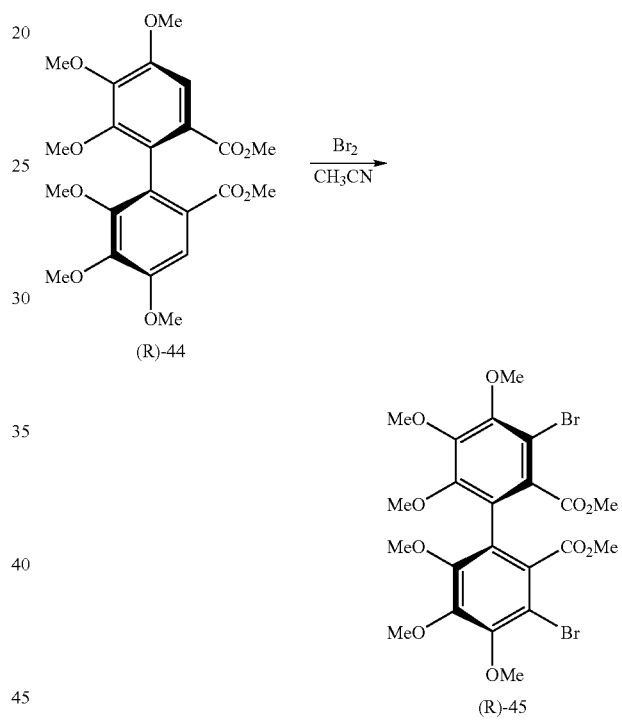

Bromine (0.51 mL, 10 mmol) was added dropwise to a solution of the compound (R)-44 obtained in Reference Example 11 (0.90 g, 2 mmol) in $CH_3CN$ (10 mL) at 0° C. The reaction mixture was stirred for three hours and then poured into a saturated aqueous $Na_2SO_3$ solution. The mixture was extracted with ethyl acetate. The combined organic layer was washed with saturated saline, and then concentrated under reduced pressure. The compound (R)-45 ((R)-3,3'-dibromo-4,5,6,4',5',6'-hexamethoxydiphenate dimethyl ester) (1.21 g, 2 mmol) was obtained in a quantitative yield. The NMR spectrum of the obtained compound (R)-45 is shown in Table 16.

TABLE 16

| NMR spectrum of compound (R)-45 |
| --- |
| 400 MHz $^1$H NMR (CDCl$_3$) δ 3.95 (12H, s, OCH$_3$), 3.79 (6H, s, OCH$_3$), 3.65 (6H, s, OCH$_3$). |

Reference Example 13

Synthesis of Starting Material (Compound (R)-46) for Synthesizing Quaternary Ammonium Salt

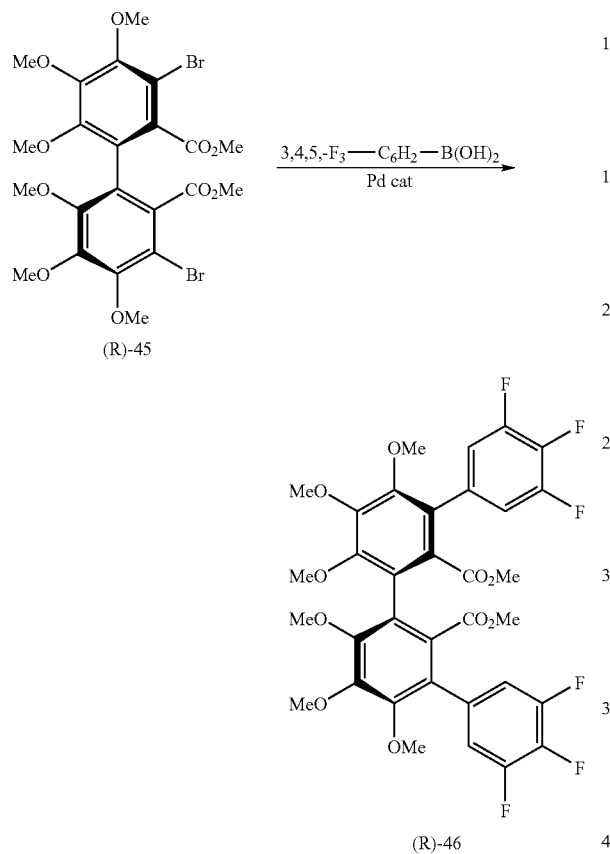

A mixture of the compound (R)-45 obtained in Reference Example 12 (1.21 g, 2 mmol), 3,4,5-trifluorophenylboronic acid (1.06 g, 6 mmol), palladium acetate (90 mg, 0.4 mmol), tri-o-tolylphosphine (0.49 g, 1.6 mmol), sodium methoxide (0.32 g, 6 mmol), and DME (10 mL) was stirred with heating at 85° C. under an argon atmosphere. The disappearance of the starting material was confirmed by TLC, and then the suspension was filtered and the filtrate was concentrated under reduced pressure. The residue was purified by silica gel column chromatography (hexane/ethyl acetate=5/1 as eluent) to give the title compound (R)-46 ((R)-3,3'-bis(3,4,5-trifluorophenyl)-4,5,6,4',5',6'-hexamethoxydiphenate dimethyl ester) (1.14 g, 1.60 mmol/yield: 80%). The NMR spectrum of the obtained compound (R)-46 is shown in Table 17.

TABLE 17

NMR spectrum of compound (R)-46

400 MHz $^1$H NMR (CDCl$_3$) δ 6.92 (4H, m, Ar—H), 3.98 (6H, s, OCH$_3$), 3.85 (6H, s, OCH$_3$), 3.71 (6H, s, OCH$_3$), 3.27 (6H, s, CO$_2$CH$_3$).

Reference Example 14

Synthesis of Starting Material (Compound (R)-47) for Synthesizing Quaternary Ammonium Salt

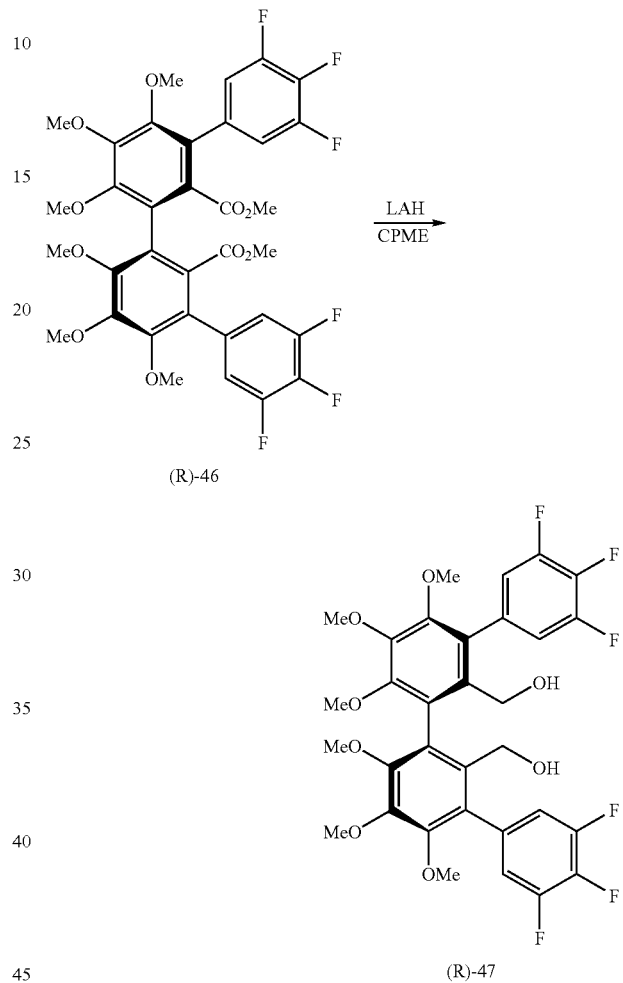

LiAlH$_4$ (0.29 g, 4.64 mmol) was added to a solution of the compound (R)-46 obtained in Reference Example 13 (1.10 g, 1.55 mmol) in cyclopentylmethylether (CPME) (11 mL) at −10° C. The reaction mixture was stirred at 0° C. for four hours. After 1 N cold HCl was added carefully, the mixture was then extracted with ethyl acetate, and concentrated under reduced pressure. The title compound (R)-47 ((R)-3,3'-bis(3, 4,5-trifluorophenyl)-4,5,6,4',5',6'-hexamethoxybiphenyl-2, 2'-dimethanol) (1.02 g, 1.55 mmol) was obtained in a quantitative yield. The NMR spectrum of the obtained compound (R)-47 is shown in Table 18.

TABLE 18

NMR spectrum of compound (R)-47

400 MHz $^1$H NMR (CDCl$_3$) δ 7.09 (4H, m, Ar—H), 3.92-4.02 (10H, m, OCH$_3$, ArCH$_2$), 3.76 (6H, s, OCH$_3$), 3.71 (6H, s, OCH$_3$), 3.19 (2H, s, OH).

Reference Example 15

Synthesis of Starting Material (Compound (R)-48) for Synthesizing Quaternary Ammonium Salt

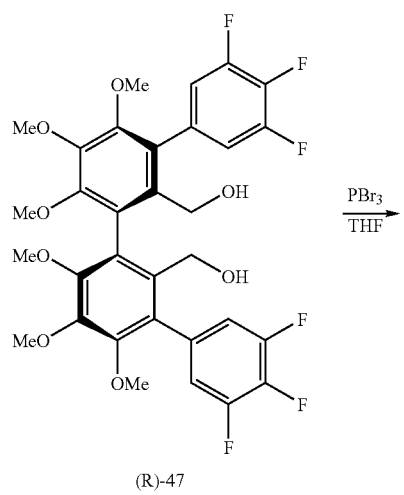

(R)-47

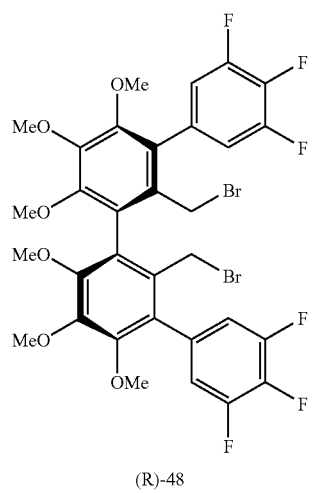

(R)-48

Phosphorus tribromide (0.44 mL, 4.65 mmol) was added to a solution of the compound (R)-47 obtained in Reference Example 14 (1.02 g, 1.55 mmol) in CPME (10 mL) at 0° C. The reaction mixture was stirred for two hours at 0° C., then a saturated aqueous NaHCO$_3$ solution was added thereto. The mixture was extracted with ethyl acetate. The organic layer was dried over Na$_2$SO$_4$ and concentrated under reduced pressure. The title compound (R)-48 ((R)-3,3'-bis(3,4,5-trifluorophenyl)-4,5,6,4',5',6'-hexamethoxybiphenyl-2,2'-dimethyl bromide) (1.21 g, 1.55 mmol) was obtained in a quantitative yield. The NMR spectrum of the obtained compound (R)-48 is shown in Table 19.

TABLE 19

NMR spectrum of compound (R)-48

400 MHz $^1$H NMR (CDCl$_3$) δ 7.08 (2H, s, Ar—H), 7.00 (2H, s, Ar—H), 3.95 (10H, m, OCH$_3$, ArCH$_2$), 3.87 (6H, s, OCH$_3$), 3.73 (6H, s, OCH$_3$).

Reference Example 16

Synthesis of Starting Material (Compound 51) for Synthesizing Quaternary Ammonium Salt

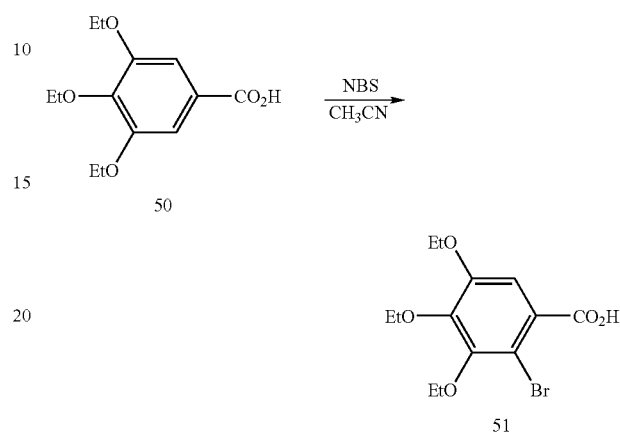

N-bromosuccinimide (NBS) (28.48 g, 160 mmol) was added to a solution of 3,4,5-triethoxy benzoic acid (compound 50) (25.43 g, 100 mmol) in CH$_3$CN (200 mL) at 0° C. This solution was stirred for three hours at 0° C. and then a saturated aqueous Na$_2$SO$_3$ solution was added thereto. After the mixture was extracted with ethyl acetate, the organic layer was washed with saturated saline, dried over Na$_2$SO$_4$, and concentrated under reduced pressure. A mixture of the title compound 51 (2-bromo-3,4,5-triethoxybenzoic acid) and the byproduct, succinimide, was obtained (47.19 g). The NMR spectrum of the compound 51 purified independently is shown in Table 20.

TABLE 20

NMR spectrum of compound 51

400 MHz $^1$H NMR (CDCl$_3$) δ 7.35 (1H, s, Ar—H), 4.17 (2H, q, J = 7.0 Hz, OCH$_2$), 4.11 (4H, q, J = 7.0 Hz, OCH$_2$), 1.46 (6H, m, CH$_3$), 1.39 (3H, t, J = 7.0 Hz, CH$_3$).

Reference Example 17

Synthesis of Starting Material (Compound 52) for Synthesizing Quaternary Ammonium Salt

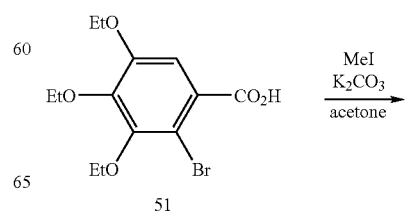

51

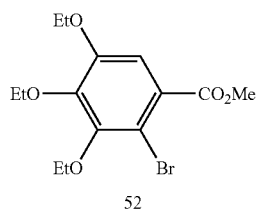

52

Potassium carbonate (20.73 g, 150 mmol) and methyl iodide (28.39 g, 200 mmol) were added to a solution of the mixture of the compound 51 and the byproduct, succinimide, obtained in Reference Example 16 (47.19 g, 100 mmol) in acetone (240 mL). This reaction mixture was heated under reflux for five hours, then a saturated aqueous $NaHCO_3$ solution was added. The reaction mixture was extracted with ethyl acetate. The organic layer was dried over $Na_2SO_4$ and concentrated under reduced pressure. The title compound 52 (2-bromo-3,4,5-triethoxybenzoate methyl ester) (34.86 g, 100 mmol) was obtained in a quantitative yield. The NMR spectrum of the obtained compound 52 is shown in Table 21.

TABLE 21

NMR spectrum of compound 52

400 MHz $^1$H NMR ($CDCl_3$) δ 7.26 (1H, s, Ar—H), 4.16-4.05 (6H, m, $OCH_2$), 3.92 (3H, s, $CO_2CH_3$), 1.44 (6H, m, $CH_3$), 1.38 (3H, t, J = 7.1 Hz, $CH_3$).

Reference Example 18

Synthesis of Starting Material (Compound 54) for Synthesizing Quaternary Ammonium Salt

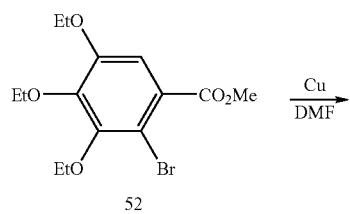

52

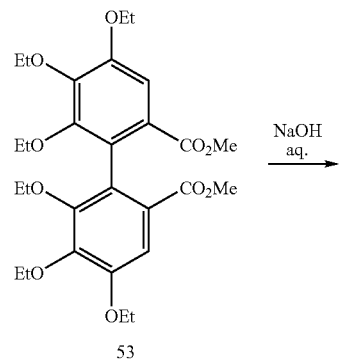

53

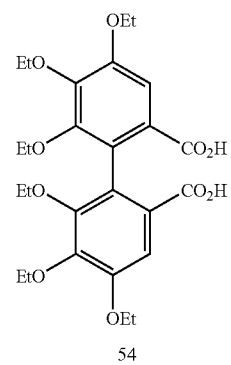

54

Under an argon atmosphere, activated Cu powder (25.42 g, 400 mmol) was added to a solution of the compound 52 obtained in Reference Example 17 (34.86 g, 100 mmol) in DMF (300 mL). After deaeration, this mixture was heated at a gentl reflux. After five hours of heated at reflux, the reaction mixture was filtered, 1 N HCl solution was added to the filtrate and the mixture was extracted with ethyl acetate. The organic layer was washed with saturated saline, dried over $Na_2SO_4$, and then concentrated under reduced pressure. A mixture of the coupling product (compound 53) and a debrominated byproduct was obtained. This was used as is in the following process without further purification.

To a solution of the compound 53 obtained above in methanol (125 mL), 8 N KOH aqueous solution (37.5 mL) was added dropwise. The reaction mixture was heated at reflux for five hours and then the methanol was removed under reduced pressure. To the residue were added methanol (20 mL) and water (100 mL) and then the mixture was acidified with concentrated hydrochloric acid. The precipitated crystals were filtered off, washed with water, and then dried. The title compound 54 (4,5,6,4',5',6'-hexaethoxydiphenic acid) was obtained (37.35 g, 37.35 mmol/yield: 75%). The NMR spectrum of the obtained compound 54 is shown in Table 22.

TABLE 22

NMR spectrum of compound 54

400 MHz $^1$H NMR ($CDCl_3$) δ 7.36 (2H, s, Ar—H), 4.20-4.07 (12H, m, $OCH_2$), 1.48-1.37 (18H, m, $CH_3$).

Reference Example 19

Synthesis of Starting Material (Optically Active Compound 54) for Synthesizing Quaternary Ammonium Salt

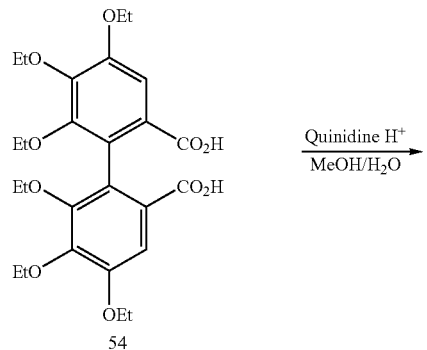

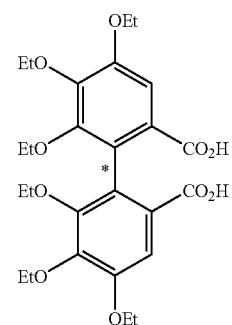

Optically active compound 54

Quinidine (18.43 g, 56.8 mmol) was added to a 60% aqueous methanol (270 mL) of the compound 54 obtained in Reference Example 18 (14.39 g, 28.4 mmol). The mixture was heated at reflux for one hour and then cooled slowly to 0° C. The precipitated crystals were collected by filtration and washed with 60% aqueous methanol, and dried to give the bisquinidine salt of 4,5,6,4',5',6'-hexaethoxydiphenic acid (9.64 g). This was recrystallized in 60% aqueous methanol (100 mL). The crystals were collected by filtration, washed with 60% hydrous methanol and dried to give the bisquinidine salt of 4,5,6,4',5',6'-hexaethoxydiphenic acid (5.20 g). Ethyl acetate (30 mL) and 1 N HCl aqueous solution (50 mL) were added thereto. The mixture was stirred at room temperature for one hour, extracted with ethyl acetate. The extract was dried over Na$_2$SO$_4$ and concentrated to give the title optically active compound 54 (optically active 4,5,6,4',5',6'-hexaethoxydiphenic acid) (2.40 g, 4.74 mmol/yield: 17%).

The enantiomeric excess was measured by HPLC analysis (Daicel Chiralcel AD-H, hexane/2-propanol/TFA=97:3:0.1, flow rate 0.4 mL/min, retention time: 53.7 min (major), 57.3 ml (minor)). The optical purity of the optically active compound 54 was 99% ee.

Reference Example 20

Synthesis of Starting Material (Optically Active Compound 53) for Synthesizing Quaternary Ammonium Salt

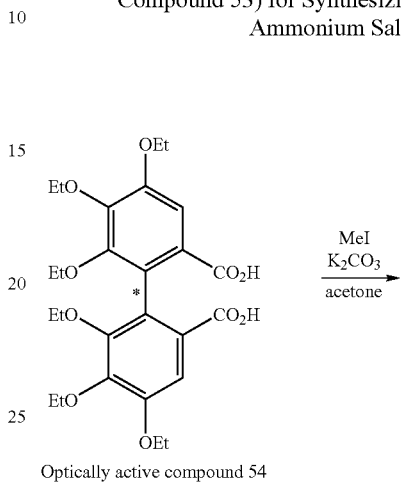

Optically active compound 54

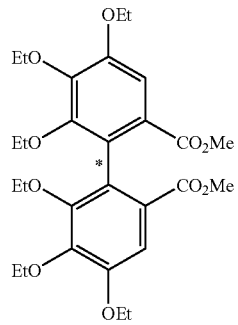

Optically active compound 53

Potassium carbonate (2.62 g, 19 mmol) and methyl iodide (4.04 g, 28.4 mmol) were added to a solution of the optically active compound 54 obtained in Reference Example 19 (2.40 g, 4.74 mmol) in acetone (24 mL). This reaction mixture was heated under reflux for five hours, and then a saturated aqueous NaHCO$_3$ solution was added to the reaction mixture and extraction was performed with ethyl acetate. The organic layer was dried over Na$_2$SO$_4$ and concentrated under reduced pressure. The title optically active compound 53 (optically active 4,5,6,4',5',6'-hexaethoxydiphenate dimethyl ester) (1.55 g, 2.90 mmol/yield:61%) was obtained. The NMR spectrum of the obtained optically active compound 53 is shown in Table 23.

TABLE 23

NMR spectrum of optically active compound 53

400 MHz $^1$H NMR (CDCl$_3$) δ 7.32 (2H, s, Ar—H), 4.17-4.11 (12H, m, OCH$_2$), 3.56 (6H, s, CO$_2$CH$_3$), 1.48 (6H, t, J = 7.0 Hz, CH$_3$), 1.37 (6H, t, J = 7.1 Hz, CH$_3$), 0.97 (6H, t, J = 7.0 Hz, CH$_3$).

Reference Example 21

Synthesis of Starting Material (Optically Active Compound 55) for Synthesizing Quaternary Ammonium Salt

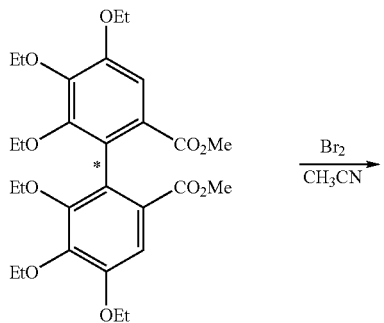

Optically active compound 53

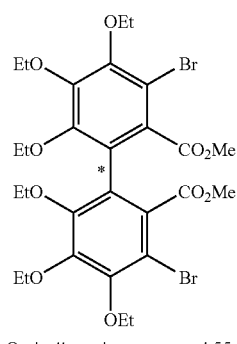

Optically active compound 55

Bromine (0.71 mL, 14 mmol) was added dropwise to a solution of the optically active compound 53 obtained in Reference Example 20 (1.55 g, 2.90 mmol) in $CH_3CN$ (16 mL) at 0° C. The reaction mixture was stirred for three hours and then poured into a saturated aqueous $Na_2SO_3$ solution. The mixture was extracted with ethyl acetate. The combined organic layer was washed with saturated saline and concentrated under reduced pressure. The title compound 55 (optically active 3,3'-dibromo-4,5,6,4',5',6'-hexaethoxydiphenate dimethyl ester) (2.05 g, 2.90 mmol) was obtained in a quantitative yield. The NMR spectrum of the obtained optically active compound 55 is shown in Table 24.

TABLE 24

NMR spectrum of optically active compound 55

400 MHz $^1$H NMR (CDCl$_3$) δ 4.204-4.05 (12H, m, OCH$_2$), 3.63 (6H, s, CO$_2$CH$_3$), 1.45 (6H, t, J = 7.1 Hz, CH$_3$), 1.38 (6H, t, J = 7.1 Hz, CH$_3$), 1.05 (6H, t, J = 7.0 Hz, CH$_3$).

Reference Example 22

Synthesis of Starting Material (Optically Active Compound 56) for Synthesizing Quaternary Ammonium Salt

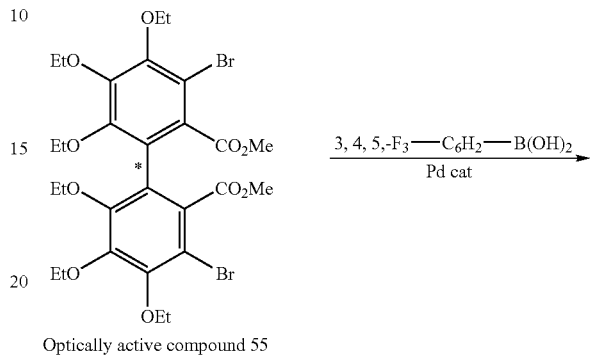

Optically active compound 55

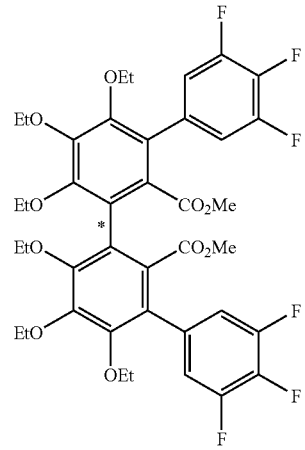

Optically active compound 56

A mixture of the optically active compound 55 obtained in Reference Example 21 (2.05 g, 2.90 mmol), 3,4,5-trifluorophenylboronic acid (1.53 g, 8.7 mmol), palladium acetate (0.13 g, 0.58 mmol), tri-o-tolylphosphine (0.71 g, 2.32 mmol), sodium methoxide (0.47 g, 8.7 mmol), and DME (17 mL) was stirred with heating at 85° C. under an argon atmosphere. The disappearance of the starting material was confirmed by TLC, and then the suspension was filtered and the filtrate was concentrated under reduced pressure. The residue was purified by silica gel column chromatography (with hexane/ethyl acetate=5/1 as the eluent) to give the title optically active compound 56 (opticall active 3,3'-bis(3,4,5-trifluorophenyl)-4,5,6,4',5',6'-hexaethoxydiphenate dimethyl ester) (1.83 g, 2.26 mmol/yield: 78%). The NMR spectrum of the obtained optically active compound 56 is shown in Table 25.

TABLE 25

NMR spectrum of optically active compound 56

400 MHz $^1$H NMR (CDCl$_3$): δ 6.89 (4H, m, Ar—H), 4.27-3.89 (12H, m, OCH$_2$), 3.25 (6H, s, CO$_2$CH$_3$), 1.41 (6H, t, J = 7.1 Hz, CH$_3$), 1.11 (12H, m, CH$_3$).

123
Reference Example 23

Synthesis of Starting Material (Optically Active Compound 57) for Synthesizing Quaternary Ammonium Salt

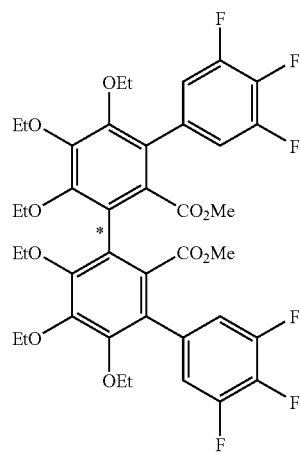

Optically active compound 56

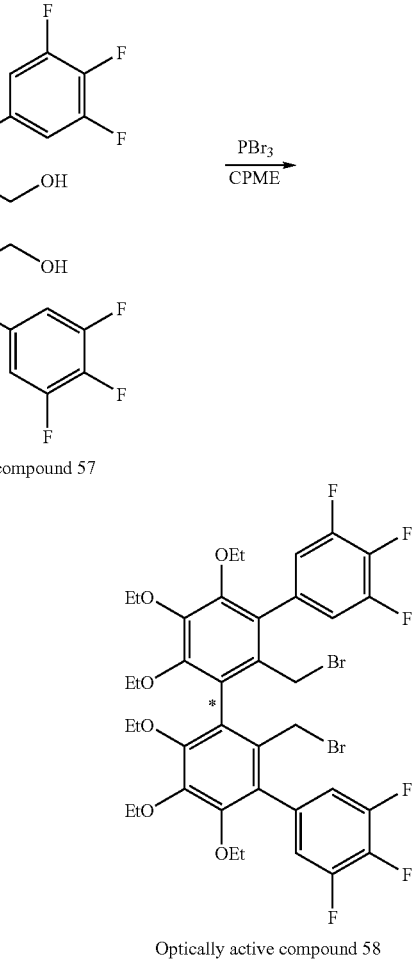

Optically active compound 57

LiAlH₄ (0.43 g, 11.3 mmol) was added to a solution of the optically active compound 56 obtained in Reference Example 22 (1.83 g, 2.26 mmol) in CPME (18 mL) at −10° C. The reaction mixture was stirred at 0° C. for four hours, and then 1 N cold HCl was added carefully. Ethyl acetate was added to the reaction mixture. After separation, and then the organic layer was dried over Na₂SO₄ and concentrated under reduced pressure. The title optically actively compound 57 (optically active 3,3'-bis(3,4,5-trifluorophenyl)-4,5,6,4',5',6'-hexaethoxybiphenyl-2,2'-dimethanol) (1.72 g, 2.26 mmol) was obtained in a quantitative yield. The NMR spectrum of the obtained optically active compound 57 is shown in Table 26.

TABLE 26

NMR spectrum of optically active compound 57

400 MHz ¹H NMR (CDCl₃) δ 7.12 (4H, m, Ar—H), 4.17-3.73 (16H, m, OCH₂, ArCH₂), 3.28 (2H, s, OH), 1.40 (6H, t, J = 7.1 Hz, CH₃), 1.10 (12H, m, CH₃).

124
Reference Example 24

Synthesis of Starting Material (Optically Active Compound 58) for Synthesizing Quaternary Ammonium Salt

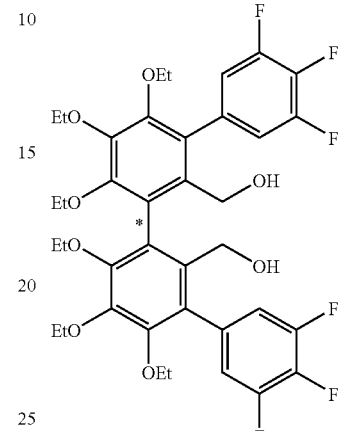

Optically active compound 57

Optically active compound 58

Phosphorus tribromide (0.64 mL, 7.8 mmol) was added to a solution of the optically active compound 57 obtained in Reference Example 23 (1.72 g, 2.26 mmol) in CPME (18 mL) at 0° C. The reaction mixture was stirred at 0° C. for two hours, then a saturated NaHCO₃ solution was added. The mixture was extracted with ethyl acetate. The organic layer was dried over Na₂SO₄ and concentrated under reduced pressure. The title optically active compound 58 (optically active 3,3'-bis(3,4,5-trifluorophenyl)-4,5,6,4',5',6'-hexaethoxybiphenyl-2,2'-dimethyl bromide) (1.95 g, 2.26 mmol) was obtained in a quantitative yield. The NMR spectrum of the obtained optically active compound 58 is shown in Table 27.

TABLE 27

NMR spectrum of optically active compound 58

400 MHz ¹H NMR (CDCl₃) δ 7.02 (4H, m, Ar—H), 4.18-3.91 (16H, m, OCH₂, ArCH₂Br), 1.40 (6H, t, J = 7.1 Hz, CH₃), 1.10 (12H, m, CH₃).

Example 15

Synthesis of Quaternary Ammonium Salt (Optically Active Compound 59)

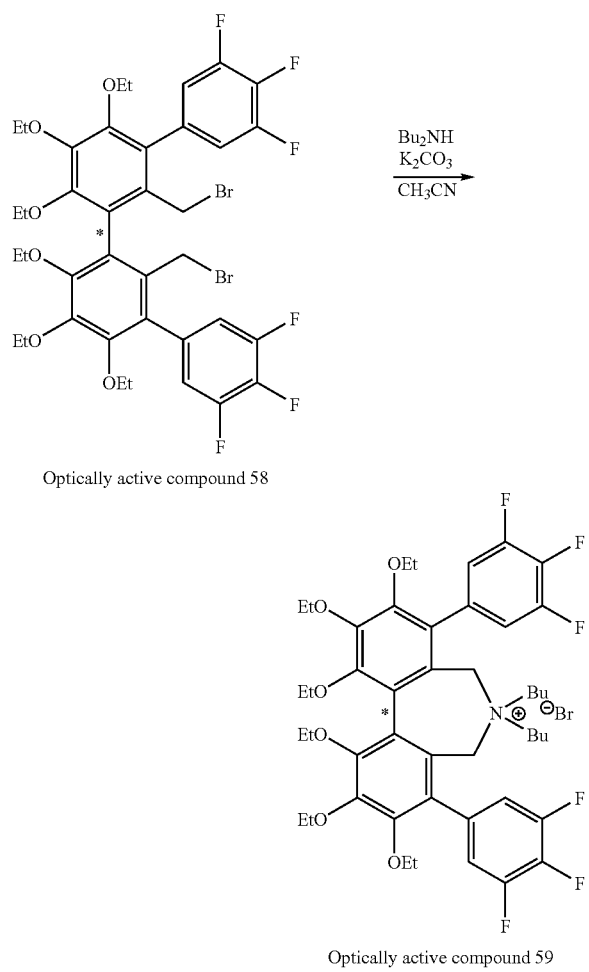

Optically active compound 58

Optically active compound 59

To a suspension of potassium carbonate (0.375 g, 2.71 mmol) and the optically active compound 58 obtained in Reference Example 24 (1.95 g, 2.26 mmol) in acetonitrile (15 mL), dibutylamine (0.424 mL, 2.49 mmol) was added under a nitrogen atmosphere. This reaction mixture was heated at 80° C. for three hours, and then poured into water. The mixture was extracted with ethyl acetate. The organic layer was dried over $Na_2SO_4$ and concentrated under reduced pressure. The residue was purified by silica gel column chromatography (with methanol/toluene=1/5 as the eluent) to give the title optically active quaternary ammonium bromide (optically active compound 59) (1.32 g, 1.45 mmol/yield: 64%). The NMR spectrum of the obtained optically active compound 59 is shown in Table 28.

TABLE 28

| NMR spectrum of optically active compound 59 obtained in Example 15 |
|---|
| 400 MHz $^1$H NMR (CDCl$_3$) δ 7.26 (2H, m, Ar—H), 7.00 (2H, m, Ar—H), 4.36 (4H, m, OCH$_2$), 4.16-4.04 (8H, m, OCH$_2$), 3.95 (2H, d, J = 12.8 Hz, ArCH$_2$N), 3.76 (2H, d, J = 12.8 Hz, ArCH$_2$N), |

TABLE 28-continued

| NMR spectrum of optically active compound 59 obtained in Example 15 |
|---|
| 3.04 (2H, m, NCH$_2$), 2.77 (2H, m, NCH$_2$), 1.45 (6H, t, J = 7.0 Hz, CH$_3$), 1.18-1.07 (18H, m, CH$_2$, CH$_3$), 0.76 (6H, m, CH$_3$), 0.23 (2H, m, CH$_2$). |

Reference Example 25

Synthesis of Starting Material (Compound 61) for Synthesizing Quaternary Ammonium Salt

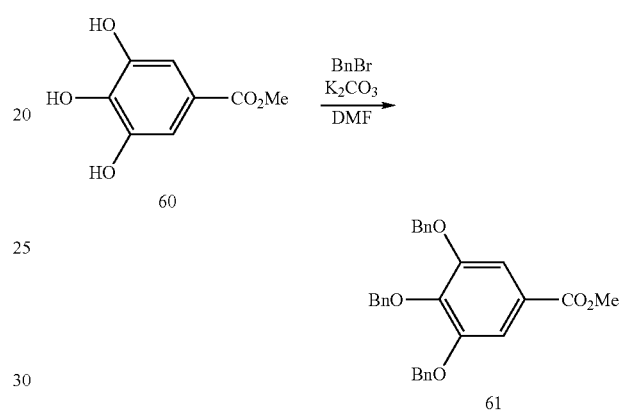

Potassium carbonate (63.31 g, 400 mmol) and benzyl bromide (59.47 mL, 500 mmol) were added to a solution of 3,4,5-trihydroxybenzoate methyl ester (compound 60) (18.41 g, 100 mmol) in DMF (70 mL). This reaction mixture was stirred at 120° C. for seven hours, and then poured into water. The mixture was extracted with ethyl acetate. The organic layer was dried over $Na_2SO_4$ and concentrated under reduced pressure. The title compound 61 (3,4,5-tribenzyloxybenzoate methyl ester) (47.19 g) was obtained in a quantitative yield. The NMR spectrum of compound 61 is shown in Table 29.

TABLE 29

| NMR spectrum of compound 61 |
|---|
| 400 MHz $^1$H NMR (CDCl$_3$) δ 7.45-7.24 (17H, m, Ar—H), 5.14 (4H, s, ArCH$_2$O), 5.11 (2H, s, ArCH$_2$O), 3.89 (3H, s, CO$_2$CH$_3$). |

Reference Example 26

Synthesis of Starting Material (Compound 62) for Synthesizing Quaternary Ammonium Salt

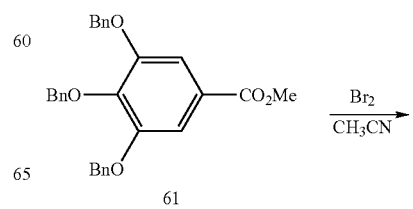

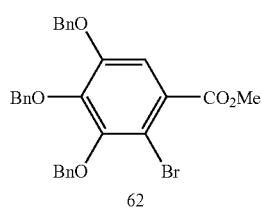

62

Bromine (20.5 mL, 400 mmol) was added dropwise to a solution of the compound 61 that was obtained in Reference Example 25 (47.19 g, 100 mmol) in CH$_3$CN (300 mL) at −10° C. This solution was stirred at 0° C. for five hours and then a saturated aqueous Na$_2$SO$_3$ solution was added thereto. After extraction with ethyl acetate, the organic layer was washed with saturated saline, dried over Na$_2$SO$_4$, and concentrated under reduced pressure. The title compound 62 (2-bromo-3,4,5-tribenzyloxybenzoate methyl ester) (53.5 g, 100 mmol) was obtained in a quantitative yield. The NMR spectrum of compound 62 is shown in Table 30.

TABLE 30

NMR spectrum of compound 62

400 MHz $^1$H NMR (CDCl$_3$) δ 7.45-7.24 (16H, m, Ar—H), 5.05 (6H, m, ArCH$_2$O), 3.99 (3H, s, CO$_2$CH$_3$).

Reference Example 27

Synthesis of Starting Material (Compound 64) for Synthesizing Quaternary Ammonium Salt

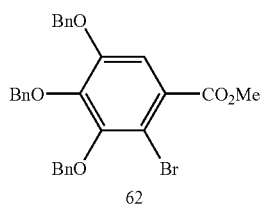 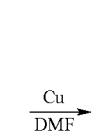

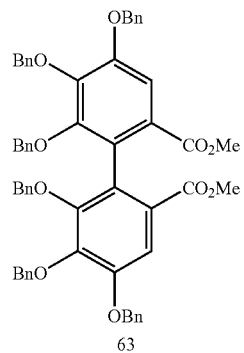 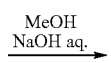

63

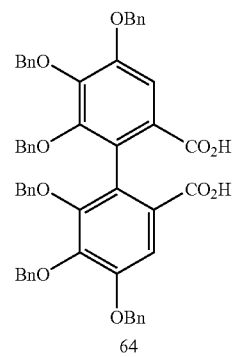

64

Under an argon atmosphere, activated Cu powder (12.71 g, 200 mmol) was added to a solution of the compound 62 obtained in Reference Example 26 (53.5 g, 100 mmol) in DMF (300 mL). After deaeration, this mixture was heated at a gentl reflux. After six hours of heating under reflux, the reaction mixture was filtered, 1 N HCl solution was added to the filtrate. The mixture was extracted with ethyl acetate. The organic layer was washed with saturated saline, dried over Na$_2$SO$_4$, and then concentrated under reduced pressure. A mixture of the coupling product (compound 63) and a debrominated byproduct was obtained. This was used as is in the following process without further purification.

To a solution of the compound 63 obtained above in methanol (300 mL) was added 8 N KOH solution (90 mL) dropwise. The reaction mixture was refluxed for five hours and then the methanol was removed under reduced pressure. To the residue were added methanol (100 mL) and water (200 mL). The mixture was then acidified with concentrated hydrochloric acid. The precipitated crystals were filtered off, washed with water, and dried. The title compound 64 (4,5,6,4',5',6'-hexabenzyloxydiphenic acid) was obtained (17.63 g, 20.05 mmol/yield: 40%). The NMR spectrum of the obtained compound 64 is shown in Table 31.

TABLE 31

NMR spectrum of compound 64

400 MHz $^1$H NMR (CDCl$_3$) δ 7.63 (2H, s, Ar—H), 7.49 (4H, d, J = 6.9 Hz, Ar—H), 7.41-7.22 (18H, m, Ar—H), 7.05 (6H, m, Ar—H), 6.81 (2H, d, J = 6.4 Hz, Ar—H), 5.25 (2H, d, J = 11.4 Hz, ArCH$_2$O), 5.15 (2H, d, J = 11.3 Hz, ArCH$_2$O), 4.98-4.93 (6H, m, ArCH$_2$O), 4.74 (2H, d, J = 11.2 Hz, ArCH$_2$O).

Reference Example 28

Synthesis of Starting Material (Optically Active Compound 64) for Synthesizing Quaternary Ammonium Salt

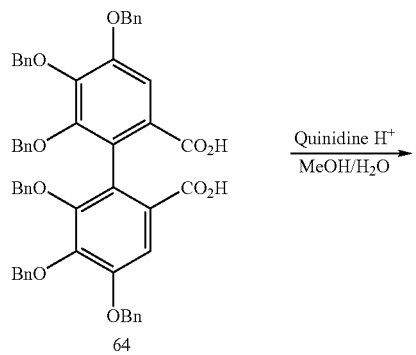 → 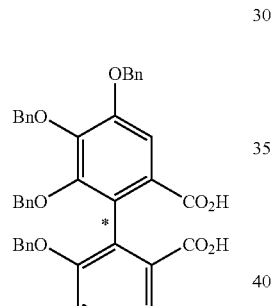

64

Optically active compound 64

Quinidine (12.55 g, 38.7 mmol) was added to a solution of the compound 64 obtained in Reference Example 27 (17.0 g, 19.3 mmol) in 92% aqueous methanol (370 mL). The reaction mixture was refluxed for one hour and then cooled slowly to 0° C. The precipitated crystals were collected by filtration and washed with the 92% aqueous methanol and then dried to give a bisquinidine salt of 4,5,6,4',5',6'-hexabenzyloxydiphenic acid (7.3 g). This was recrystallized from methanol (100 mL). The crystals were collected by filtration, washed with methanol, and dried to give the bisquinidine salt of 4,5,6,4',5',6'-hexabenzyloxydiphenic acid (3.29 g). Ethyl acetate (30 mL) and 1 N HCl aqueous solution (50 mL) were added thereto, and the mixture was stirred at room temperature for one hour. The mixture was extracted with ethyl acetate and dried over $Na_2SO_4$ and concentrated under reduced pressure to give the title optically active compound 64 (optically active 4,5,6,4',5',6'-hexabenzyloxydiphenic acid) (2.00 g, 2.27 mmol/yield: 11%).

The enantiomeric excess was analyzed by HPLC (Daicel Chiralcel AD-H, hexane/2-propanol/TFA=93:7:0.1, flow rate 0.6 mL/min, retention time: 35.1 min (major), 54.4 min (minor)). The optical purity of the optically active compound 64 was 99% ee.

Reference Example 29

Synthesis of Starting Material (Optically Active Compound 63) for Synthesizing Quaternary Ammonium Salt

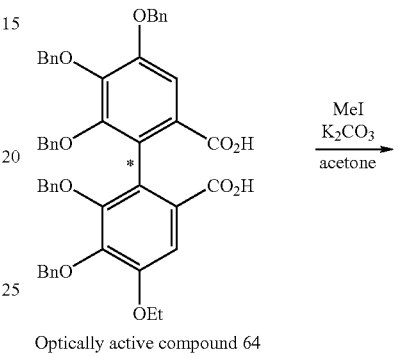

Optically active compound 64

→ 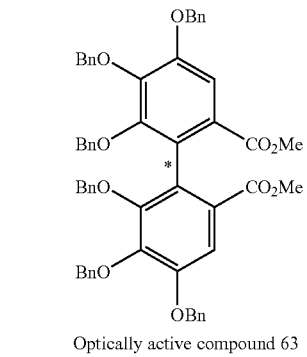

Optically active compound 63

Potassium carbonate (2.62 g, 19 mmol) and methyl iodide (4.04 g, 28.4 mmol) were added to a solution of the optically active compound 64 obtained in Reference Example 28 (2.40 g, 4.74 mmol) in acetone (24 mL). This reaction mixture was heated under reflux for five hours, and then a saturated $NaHCO_3$ solution was added to the reaction mixture. The mixture was extracted with ethyl acetate. The organic layer was dried over $Na_2SO_4$ and concentrated under reduced pressure. The title optically active compound 63 (optically active 4,5,6,4',5',6'-hexabenzyloxydiphenate dimethyl ester) (1.55 g, 2.90 mmol/yield: 61%) was obtained. The NMR spectrum of the obtained optically active compound 63 is shown in Table 32.

TABLE 32

NMR spectrum of optically active compound 63

400 MHz $^1$H NMR (CDCl$_3$) δ 7.54 (2H, s, Ar—H), 7.50 (4H, d, J = 6.7 Hz, Ar—H), 7.41-7.11 (22H, m, Ar—H), 6.86 (4H, d, J = 6.2 Hz, Ar—H), 5.20 (4H, d, J = 4.9 Hz, ArCH$_2$O), 5.15 (4H, d, J = 4.1 Hz, ArCH$_2$O), 4.89 (2H, d, J = 11.2 Hz, ArCH$_2$O), 4.76 (2H, d, J = 11.1 Hz, ArCH$_2$O), 3.58 (6H, s, CO$_2$CH$_3$).

131
Reference Example 30

Synthesis of Starting Material (Optically Active Compound 65) for Synthesizing Quaternary Ammonium Salt

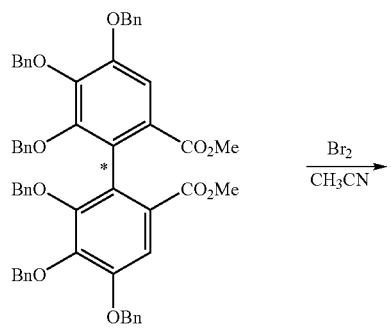
Optically active compound 63

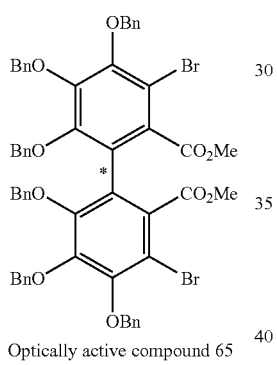
Optically active compound 65

Bromine (1.40 mL, 27.2 mmol) was added dropwise to a solution of the optically active compound 63 obtained in Reference Example 29 (2.06 g, 2.27 mmol) in CH₃CN (50 mL) at −10° C. The reaction mixture was stirred at 0° C. for three hours and then poured into a saturated aqueous $Na_2SO_3$ solution. The mixture was extracted with ethyl acetate. The combined organic layer was washed with saturated saline and concentrated under reduced pressure. The residue was purified by silica gel column chromatography (with hexane/ethyl acetate=5/1 as the eluent) to give the title optically active compound 65 (optically active 3,3'-dibromo-4,5,6,4',5',6'-hexabenzyloxydiphenate dimethyl ester) (0.19 g, 0.178 mmol/yield: 7.9%). The NMR spectrum of the obtained optically active compound 65 is shown in Table 33.

TABLE 33

NMR spectrum of optically active compound 65

400 MHz ¹H NMR (CDCl₃) δ 7.52 (4H, d, J = 2.1 Hz, Ar—H), 7.50-7.15 (22H, m, Ar—H), 6.94 (4H, m, Ar—H), 5.12-4.85 (12H, m, Ar—H), 3.68 (6H, s, CO₂CH₃).

132
Reference Example 31

Synthesis of Starting Material (Optically Active Compound 66) for Synthesizing Quaternary Ammonium Salt

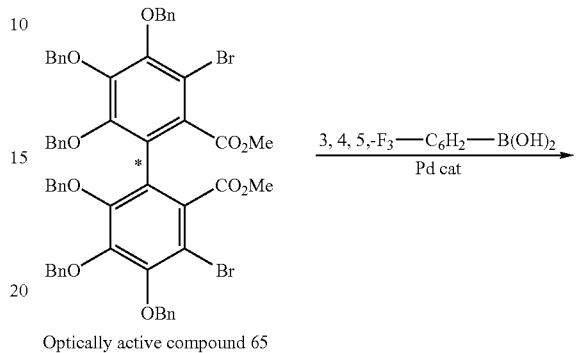
Optically active compound 65

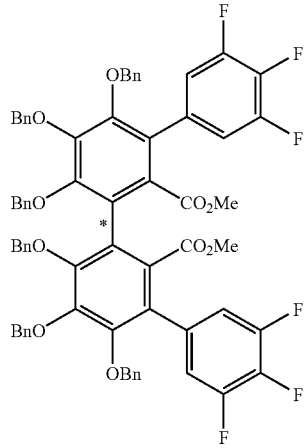
Optically active compound 66

A mixture of the optically active compound 65 obtained in Reference Example 30 (0.19 g, 0.178 mmol), 3,4,5-trifluorophenylboronic acid (94 mg, 0.53 mmol), palladium acetate (8.0 mg, 0.036 mmol), tri-o-tolylphosphine (43 mg, 0.142 mmol), sodium methoxide (29 mg, 0.53 mmol), and DME (5 mL) was stirred with heating at 85° C. under an argon atmosphere. The disappearance of the starting material was confirmed by TLC. The suspension was filtered and the filtrate was concentrated under reduced pressure. The residue was purified by silica gel column chromatography (hexane/ethyl acetate=5/1 as eluent) to give the title optically active compound 66 (optically active 3,3'-bis(3,4,5-trifluorophenyl)-4,5,6,4',5',6'-hexabenzyloxydiphenate dimethyl ester) (0.15 g, 0.129 mmol/yield: 72%). The NMR spectrum of the obtained optically active compound 66 is shown in Table 34.

TABLE 34

NMR spectrum of optically active compound 66

400 MHz ¹H NMR (CDCl₃): δ 7.36-7.21 (22H, m, Ar—H), 7.05-6.96 (8H, m, Ar—H), 6.65 (4H, m, Ar—H), 5.21 (2H, d, J = 11.2 Hz, ArCH₂O), 5.10 (4H, dd, J = 10.8 Hz, J = 3.4 Hz, ArCH₂O), 4.96 (4H, dd, J = 10.7 Hz, J = 2.5 Hz, ArCH₂O), 4.84 (2H, d, J = 10.8 Hz, ArCH₂O), 3.27 (6H, s, CO₂CH₃).

Reference Example 32

Synthesis of Starting Material (Optically Active Compound 67) for Synthesizing Quaternary Ammonium Salt

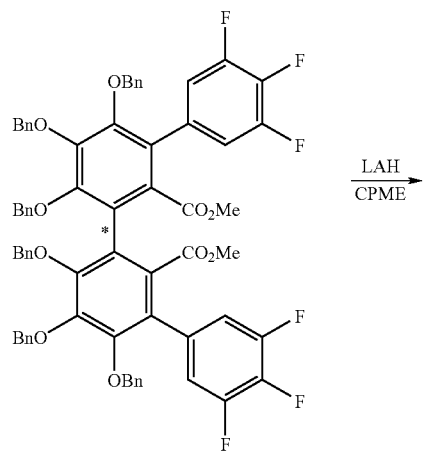

Optically active compound 66

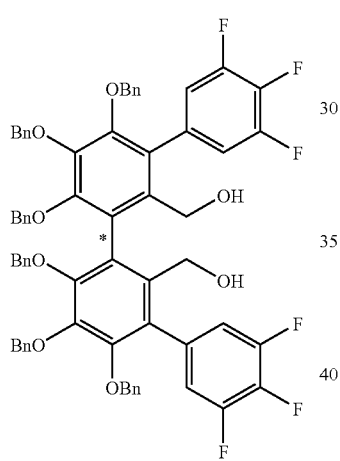

Optically active compound 67

LiAlH₄ (36 mg, 0.9 mmol) was added to a solution of the optically active compound 66 obtained in Reference Example 31 (150 mg, 0.129 mmol) in CPME (5 mL) at −10° C. The reaction mixture was stirred at 0° C. for three hours, and then 1 N cold HCl was added carefully. The mixture was extracted with ethyl acetate. The organic layer was dried over Na₂SO₄ and concentrated under reduced pressure. The title optically active compound 67 (optically active 3,3'-bis(3,4,5-trifluorophenyl)-4,5,6,4',5',6'-hexabenzyloxybiphenyl-2,2'-dimethanol) (149 mg, 0.129 mmol) was obtained in a quantitative yield. The NMR spectrum of the obtained optically active compound 67 is show in Table 35.

TABLE 35

| NMR spectrum of optically active compound 67 |
| --- |
| 400 MHz $^1$H NMR (CDCl₃): δ 7.37-7.24 (22H, m, Ar—H), 7.04-6.87 (10H, m, Ar—H), 6.77 (2H, m, Ar—H), 5.12-5.01 (8H, m, ArCH₂O), 4.86-4.81 (4H, dd, J = 11.0 Hz, J = 7.0 Hz, ArCH₂O), 4.07 (2H, d, J = 11.4 Hz, ArCH₂O), 3.97 (2H, d, J = 11.4 Hz, ArCH₂O). |

Reference Example 33

Synthesis of Starting Material (Optically Active Compound 68) for Synthesizing Quaternary Ammonium Salt

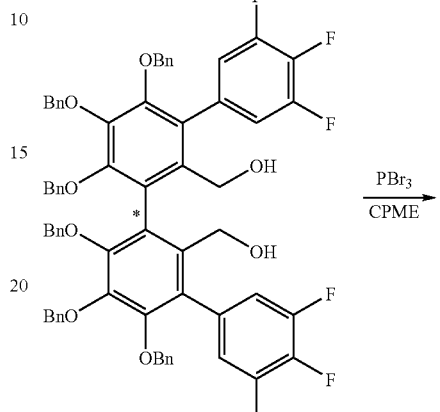

Optically active compound 67

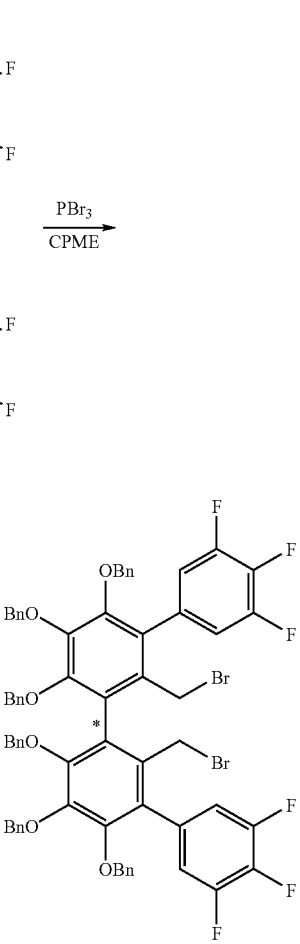

Optically active compound 68

Phosphorus tribromide (0.034 mL, 0.54 mmol) was added to a solution of the optically active compound 67 obtained in Reference Example 32 (100 mg, 0.09 mmol) in CPME (3 mL) at 0° C. The reaction mixture was stirred at 0° C. for four hours. A saturated aqueous NaHCO₃ solution was then added, and the mixture was extracted with ethyl acetate. The organic layer was dried over Na₂SO₄ and concentrated under reduced pressure. The title optically active compound 68 (optically active 3,3'-bis(3,4,5-trifluorophenyl)-4,5,6,4',5',6'-hexabenzyloxybiphenyl-2,2'-dimethyl bromide) (69 mg, 0.056 mmol/ yield: 62%) was obtained. The NMR spectrum of the obtained optically active compound 68 is shown in Table 36.

TABLE 36

| NMR spectrum of optically active compound 68 |
| --- |
| 400 MHz $^1$H NMR (CDCl₃): δ 7.34-7.23 (22H, m, Ar—H), 6.98 (8H, d, J = 6.5 Hz, Ar—H), 6.82-6.71 (4H, m, Ar—H), 5.18 (2H, d, J = 11.9 Hz, ArCH₂), 5.07-5.00 (6H, m, ArCH₂), 4.93-4.86 (4H, m, ArCH₂), 3.96 (4H, m, ArCH₂). |

Example 16

Synthesis of Quaternary Ammonium Salt (Optically Active Compound 69)

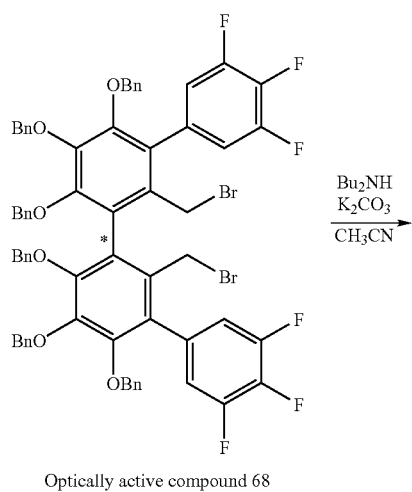

Optically active compound 68

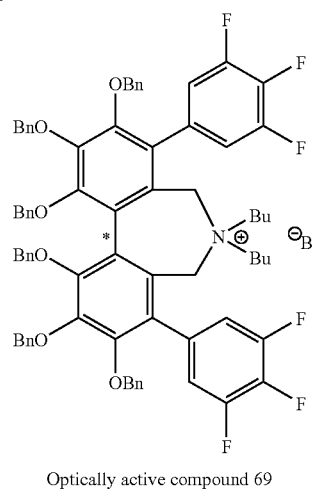

Optically active compound 69

Dibutylamine (0.011 mL, 0.062 mmol) was added to a suspension of potassium carbonate (12 mg, 0.084 mmol) and the optically active compound 68 obtained in Reference Example 33 (69 mg, 0.056 mmol) in acetonitrile (3 mL) under a nitrogen atmosphere. This reaction mixture was heated at 80° C. for three hours, and then poured into water. The mixture was extracted with ethyl acetate. The organic layer was dried over $Na_2SO_4$ and concentrated under reduced pressure. The residue was purified by silica gel column chromatography (methanol/toluene=1/5 as eluent) to give the title optically active quaternary ammonium bromide (optically active compound 69) (71 mg, 0.055 mmol/yield: 98%). The NMR spectrum of the optically active compound 69 obtained in this example is shown in Table 37.

TABLE 37

NMR spectrum of optically active compound 69 obtained in Example 16

400 MHz $^1$H NMR ($CDCl_3$) δ 7.45-7.13 (28H, m, Ar—H), 6.96 (4H, m, Ar—H), 6.61 (2H, m, Ar—H), 5.34 (2H, d, J = 11.1 Hz, ArCH$_2$O), 5.18 (4H, s, ArCH$_2$O), 5.11 (2H, d, J = 11.2 Hz, ArCH$_2$O),

TABLE 37-continued

NMR spectrum of optically active compound 69 obtained in Example 16

4.98 (4H, dd, J = 4.2, 6.9 Hz, ArCH$_2$O), 3.98 (2H, d, J = 13.5 Hz, ArCH$_2$N), 3.60 (2H, d, J = 13.5 Hz, ArCH$_2$N), 2.87 (2H, m, NCH$_2$), 2.61 (2H, m, NCH$_2$), 1.15-1.00 (6H, m, CH$_2$), 0.75 (6H, t, J = 7.0 Hz, CH$_3$), 0.21 (2H, m, CH$_2$).

Reference Example 34

Synthesis of Starting Material (Compound 71) for Synthesizing Quaternary Ammonium Salt

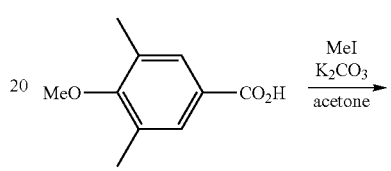

70

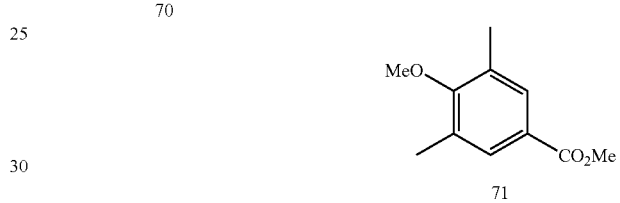

71

Potassium carbonate (4.15 g, 30 mmol) and methyl iodide (5.60 ml, 90 mmol) were added to a solution of 3,5-dimethyl-4-methoxybenzoic acid (compound 70) (2.70 g, 15 mmol) in acetone (27 mL). This reaction mixture was refluxed for five hours, and then poured into water. The mixture was extracted with ethyl acetate. The organic layer was dried over $Na_2SO_4$ and concentrated under reduced pressure. The title compound 71 (3,5-dimethyl-4-methoxybenzoate methyl ester) (2.91 g) was obtained in a quantitative yield. The NMR spectrum of the compound 71 is shown in Table 38.

TABLE 38

NMR spectrum of compound 61

400 MHz $^1$H NMR ($CDCl_3$) δ 7.71 (2H, s, Ar—H), 3.88 (3H, s, OCH$_3$), 3.75 (6H, s, OCH$_3$), 2.31 (6H, s, CH$_3$).

Reference Example 35

Synthesis of Starting Material (Compound 72) for Synthesizing Quaternary Ammonium Salt

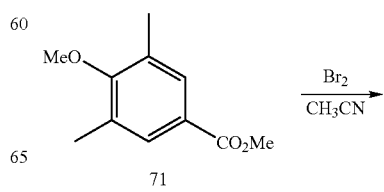

71

-continued

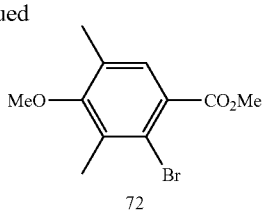

Bromine (6.15 mL, 120 mmol) was added dropwise to a solution of the compound 71 obtained in Reference Example 34 (2.91 g, 15 mmol) in CH₃CN (30 mL) at −10° C. This solution was stirred at room temperature for five hours and then a saturated aqueous Na₂SO₃ solution was added thereto. After extraction with ethyl acetate, the organic layer was dried over Na₂SO₄ and concentrated under reduced pressure. The title compound 72 (2-bromo-3,5-dimethyl-4-methoxybenzoate methyl ester) (4.10 g, 15 mmol) was obtained in a quantitative yield The NMR spectrum of compound 72 is shown in Table 39.

TABLE 39

NMR spectrum of compound 72

400 MHz ¹H NMR (CDCl₃) δ 7.41 (1H, s, Ar—H), 3.91 (3H, s, OCH₃), 3.71 (3H, s, OCH₃), 2.40 (3H, s, CH₃), 2.26 (3H, s, CH₃).

Reference Example 36

Synthesis of Starting Material (Compound 73) for Synthesizing Quaternary Ammonium Salt

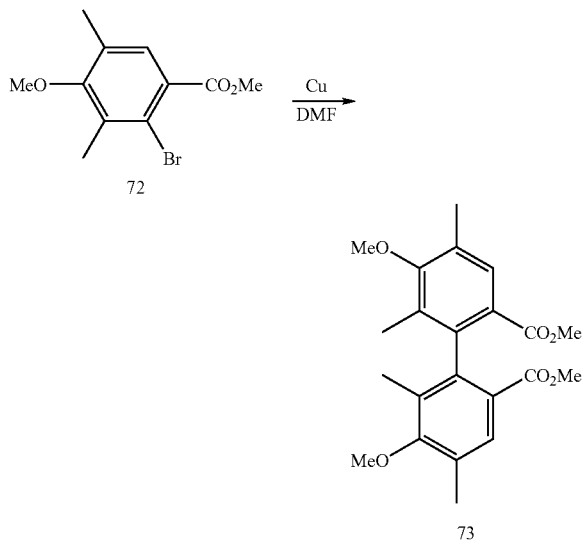

Under an argon atmosphere, activated Cu powder (3.81 g, 60 mmol) was added to a solution of the compound 72 obtained in Reference Example 35 (4.10 g, 15 mmol) in DMF (25 mL). After deaeration, this was heated to a gentl reflux. After four hours of heating under reflux, the reaction mixture was filtered. Then, 1 N HCl solution was added to the filtrate and the mixture was extracted with ethyl acetate. The organic layer was washed with saturated saline, dried over Na₂SO₄, and then concentrated under reduced pressure. The residue was purified by silica gel column chromatography (hexane/ethyl acetate=5/1 as eluent) to give the title compound 73 (4,6,4',6'-tetramethyl-5,5'-dimethoxydiphenate dimethyl ester) (2.27 g, 5.87 mmol/yield: 78%). The NMR spectrum of the obtained compound 73 is shown in Table 40.

TABLE 40

NMR spectrum of compound 73

400 MHz ¹H NMR (CDCl₃) δ 7.72 (2H, s, Ar—H), 3.75 (6H, s, OCH₃), 3.56 (6H, s, OCH₃), 2.36 (6H, s, CH₃), 1.80 (6H, s, CH₃).

Reference Example 37

Synthesis of Starting Material (Compound 74) for Synthesizing Quaternary Ammonium Salt

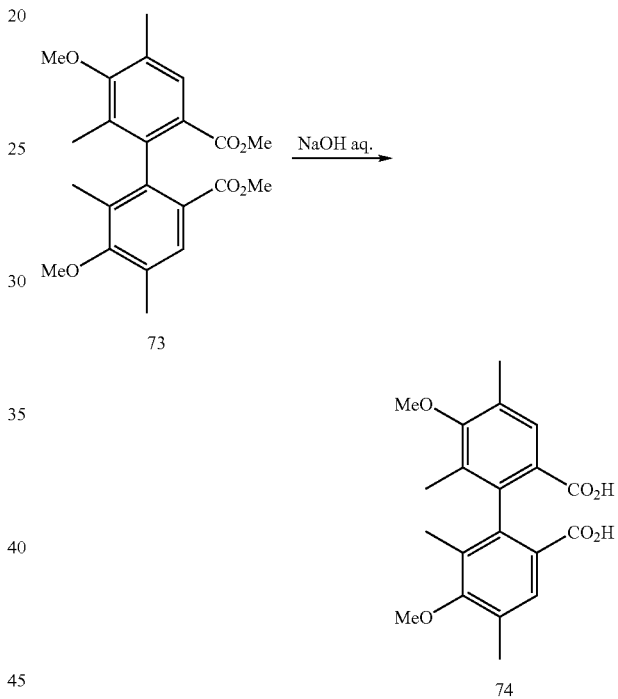

To a solution of the compound 73 obtained in Reference Example 36 (0.43 g, 1.1 mmol) in methanol (10 mL), 8 N KOH aqueous solution (4 mL) was added dropwise. The reaction mixture was refluxed for five hours, and then the methanol was removed under reduced pressure. To the residue was added 2 N hydrochloric acid tuntil the mixture turned acidic. The mixture was extracted with ethyl acetate. The organic layer was dried over Na₂SO₄, and then concentrated under reduced pressure. The title compound 74 (4,6,4',6'-tetramethyl-5,5'-dimethoxydiphenic acid) (0.39 g, 1.1 mmol) was obtained in quantitative yield. The NMR spectrum of the obtained compound 74 is shown in Table 41.

TABLE 41

NMR spectrum of compound 74

400 MHz ¹H NMR (CDCl₃) δ 7.72 (2H, s, Ar—H), 3.72 (6H, s, OCH₃), 2.36 (6H, s, CH₃), 1.75 (6H, s, CH₃).

Reference Example 38

Synthesis of Starting Material (Optically Active Compound 74) for Synthesizing Quaternary Ammonium Salt

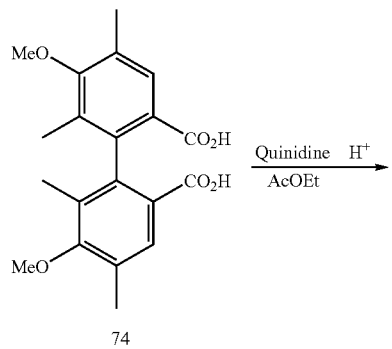

74

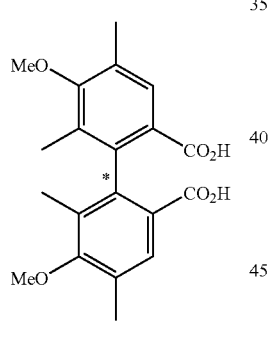

Optically active compound 74

Quinidine (0.71 g, 38.7 mmol) was added to a solution of the compound 74 obtained in Reference Example 37 (0.39 g, 1.1 mmol) in ethyl acetate (4 mL). The reaction mixture was refluxed for one hour and then cooled slowly to 0° C. The precipitated crystals were collected by filtration, washed with ethyl acetate and dried to give the bisquinidine salt of 4,6,4',6'-tetramethyl-5,5'-dimethoxydiphenic acid (0.50 g). Ethyl acetate (10 mL) and 1 N HCl aqueous solution (20 mL), were added thereto and the mixture was stirred at room temperature for one hour. The mixture was extracted with ethyl acetate and the organic layer was dried over $Na_2SO_4$ and concentrated under reduced pressure to give the title optically active compound 74 (optically active 4,6,4',6'-tetramethyl-5,5'-dimethoxydiphenic acid) (0.16 g, 0.45 mmol/yield: 41%).

The enantiomeric excess was analyzed by HPLC (Daicel Chiralcel AD-H, hexane/2-propanol/TFA=95:5:0.1, flow rate 0.7 mL/min, retention time: 16.6 min (minor), 34.1 min (major)). The optical purity of the optically active compound 74 was 99% ee.

Reference Example 39

Synthesis of Starting Material (Optically Active Compound 75) for Synthesizing Quaternary Ammonium Salt

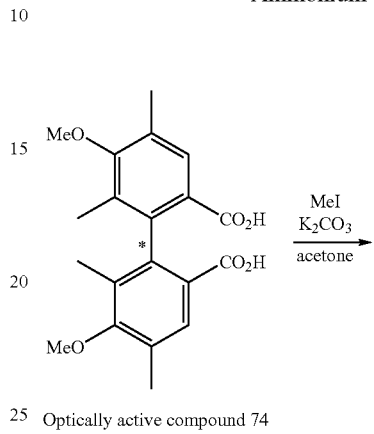

Optically active compound 74

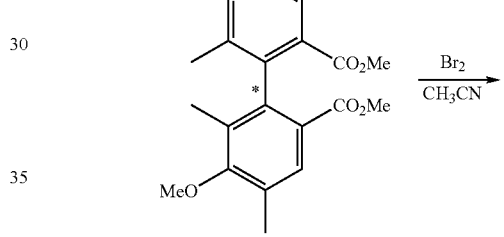

Optically active compound 73

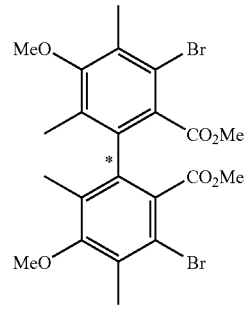

Optically active compound 75

Potassium carbonate (247 mg, 1.79 mmol) and methyl iodide (556 μL, 8.92 mmol) were added to a solution of the optically active compound 74 obtained in Reference Example 38 (0.16 g, 0.45 mmol) in acetone (5 mL). This reaction mixture was heated under reflux for five hours, and then a saturated $NaHCO_3$ solution was added to the reaction mixture. Extraction was then performed with ethyl acetate. The organic layer was dried over $Na_2SO_4$ and concentrated under reduced pressure. The optically active compound 73 (optically active 4,6,4',6'-tetramethyl-5,5'-dimethoxydiphenate dimethyl ester) (0.17 g, 0.45 mmol) was obtained in a quantitative yield.

Bromine (458 μL, 8.92 mmol) was added dropwise to a solution of the optically active compound 73 obtained above (0.17 g, 0.45 mmol) in CH₃CN (5 mL) at 0° C. The reaction mixture was stirred at room temperature for five hours and then poured into a saturated aqueous Na₂SO₃ solution and the mixture was extracted with ethyl acetate. The organic layer was dried over Na₂SO₄ and concentrated under reduced pressure. The title optically active compound 75 (optically active 3,3'-dibromo-4,6,4',6'-tetramethyl-5,5'-dimethoxydiphenate dimethyl ester) (0.24 g, 0.45 mmol) was obtained in a quantitative yield. The NMR spectrum of the obtained optically active compound 75 is shown in Table 42.

TABLE 42

NMR spectrum of optically active compound 75

400 MHz ¹H NMR (CDCl₃) δ 3.71 (6H, s, OCH₃), 3.59 (6H, s, OCH₃), 2.42 (6H, s, CH₃), 1.90 (6H, s, CH₃).

the filtrate was added a 1 N HCl solution, and the mixture was extracted with ethyl acetate. The organic layer was washed with saturated saline, dried over Na₂SO₄, and then concentrated under reduced pressure. The residue was purified by silica gel column chromatography (hexane/ethyl acetate=15/1 as eluent) to give the title optically active compound 76 (optically active 3,3'-bis(3,4,5-trifluorophenyl)-4,6,4',6'-tetramethyl-5,5'-dimethoxy diphenate dimethyl ester) (184 mg, 0.285 mmol/yield: 64%). The NMR spectrum of the obtained optically active compound 76 is shown in Table 43.

TABLE 43

NMR spectrum of optically active compound 76

400 MHz ¹H NMR (CDCl₃) δ 6.84 (4H, m, Ar—H), 3.76 (6H, s, OCH₃), 3.21 (6H, s, OCH₃), 2.36 (6H, s, CH₃), 1.80 (6H, s, CH₃).

Reference Example 40

Synthesis of Starting Material (Optically Active Compound 76) for Synthesizing Quaternary Ammonium Salt Reference Example 41

Synthesis of Starting Material (Optically Active Compound 77) for Synthesizing Quaternary Ammonium Salt

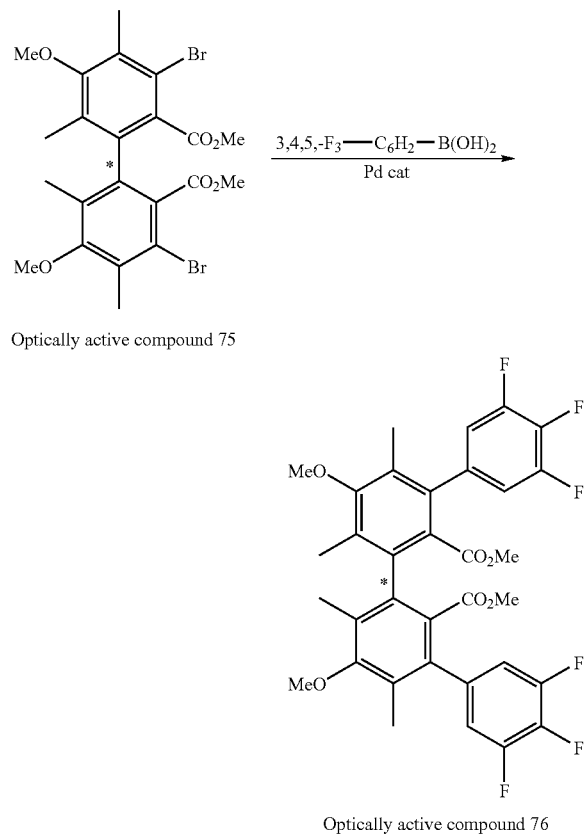

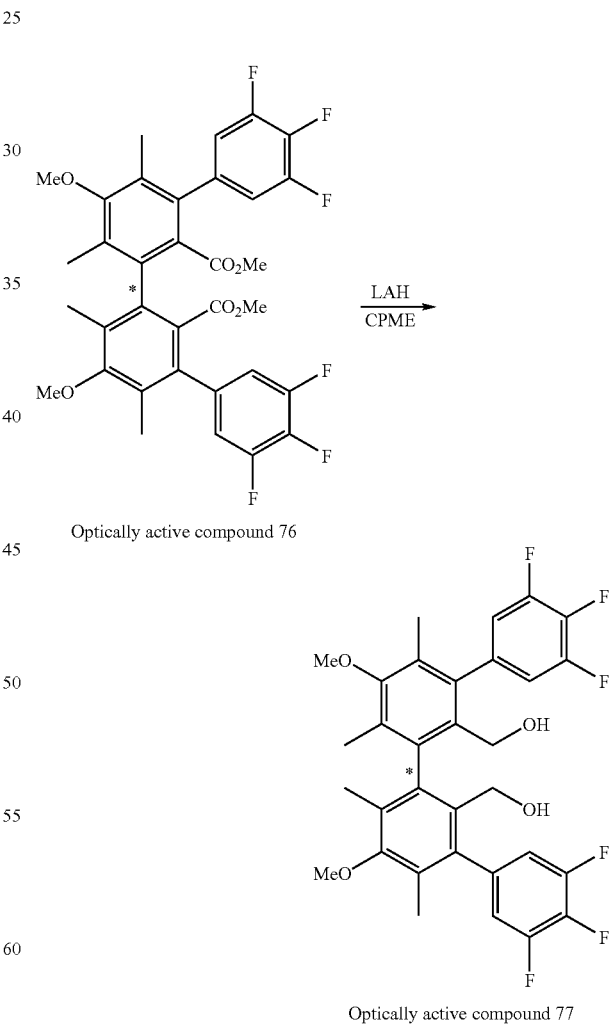

A mixture of the optically active compound 75 obtained in Reference Example 39 (0.24 g, 0.45 mmol), 3,4,5-trifluorophenylboronic acid (236 mg, 1.34 mmol), palladium acetate (20 mg, 0.089 mmol), tri-o-tolylphosphine (109 mg, 0.36 mmol), sodium methoxide (72 mg, 1.34 mmol), and DME (4 mL) was stirred with heating at 85° C. under an argon atmosphere. The disappearance of the starting material was confirmed by TLC, and then the suspension was filtered. To LiAlH₄ (54 mg, 1.42 mmol) was added to a solution of the optically active compound 76 obtained in Reference Example 40 (184 mg, 0.285 mmol) in CPME (3 mL) at −10° C. The reaction mixture was stirred at 0° C. for three hours, and then 1 N cold HCl was added carefully, and the mixture was extracted with ethyl acetate. The organic layer was dried over $Na_2SO_4$ and concentrated under reduced pressure. The title optically active compound 77 (optically active 3,3'-bis(3,4,5-trifluorophenyl)-4,6,4',6'-tetramethyl-5,5'-dimethoxybiphenyl-2,2'-dimethanol) (168 mg, 0.285 mmol) was obtained in a quantitative yield. The NMR spectrum of the obtained optically active compound 77 is shown in Table 44.

TABLE 44

NMR spectrum of optically active compound 77

400 MHz $^1$H NMR (CDCl$_3$) δ 7.06 (2H, m, Ar—H), 6.82 (2H, m, Ar—H), 3.93 (4H, s, ArCH$_2$O), 3.73 (6H, s, OCH$_3$), 3.27 (2H, s, OH), 2.02 (6H, s, CH$_3$), 1.83 (6H, s, CH$_3$).

Reference Example 42

Synthesis of Starting Material (Optically Active Compound 78) for Synthesizing Quaternary Ammonium Salt

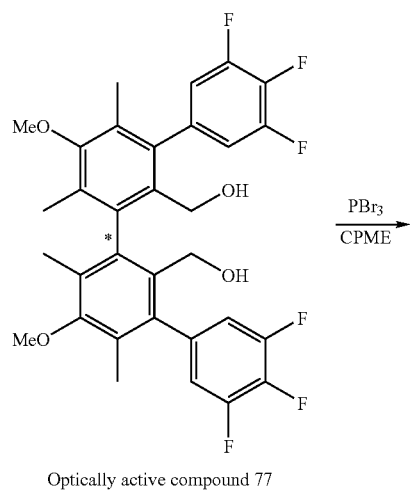

Optically active compound 77

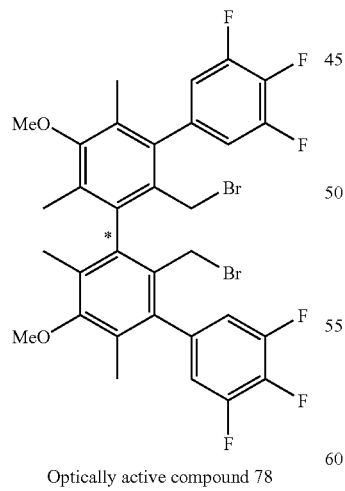

Optically active compound 78

Phosphorus tribromide (0.134 mL, 1.42 mmol) was added to a solution of the optically active compound 77 obtained in Reference Example 41 (168 mg, 0.285 mmol) in CPME (3 mL) at 0° C. The reaction mixture was stirred at 0° C. for four hours. A saturated aqueous NaHCO$_3$ solution was then added and the mixture was extracted with ethyl acetate. The organic layer was dried over Na$_2$SO$_4$ and concentrated under reduced pressure. The title optically active compound 78 (optically active 3,3'-bis(3,4,5,-trifluorophenyl)-4,6,4',6'-tetramethyl-5,5'-dimethoxybiphenyl-2,2'-dimethyl bromide) (204 mg, 0.285 mmol) was obtained in a quantitative yield. The NMR spectrum of the obtained optically active compound 78 is shown in Table 45.

TABLE 45

NMR spectrum of optically active compound 78

400 MHz $^1$H NMR (CDCl$_3$) δ 6.96 (4H, m, Ar—H), 3.91 (2H, d, J = 10.0 Hz, ArCH$_2$Br), 3.83 (2H, d, J = 10.0 Hz, ArCH$_2$Br), 3.78 (6H, s, OCH$_3$), 2.02 (12H, s, CH$_3$).

Example 17

Synthesis of Quaternary Ammonium Salt (Optically Active Compound 79)

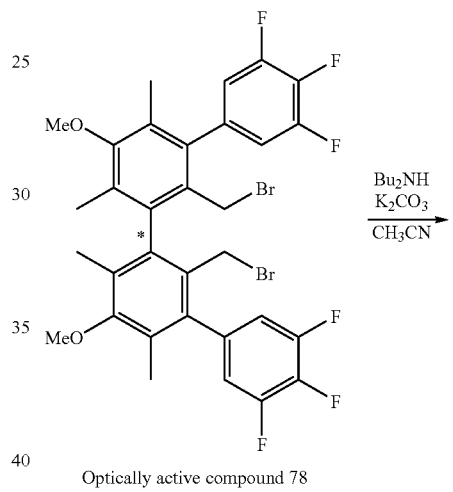

Optically active compound 78

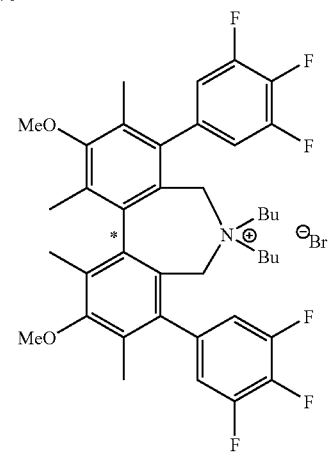

Optically active compound 79

Dibutylamine (0.0728 mL, 0.427 mmol) was added to a suspension of potassium carbonate (157 mg, 1.14 mmol) and the optically active compound 78 obtained in Reference Example 42 (204 mg, 0.285 mmol) in acetonitrile (3 mL) under a nitrogen atmosphere. This reaction mixture was heated at 80° C. for three hours. Then, this was poured into water, and then the mixture was extracted with ethyl acetate.

The organic layer was dried over Na₂SO₄ and concentrated under reduced pressure. The residue was purified by silica gel column chromatography (methanol/ethyl acetate=1/5 as eluent) to give the title optically active quaternary ammonium bromide (optically active compound 79) (132 mg, 0.173 mmol/yield: 61%). The NMR spectrum of the optically active compound 79 that was obtained in this example is shown in Table 46.

TABLE 46

NMR spectrum of optically active compound 79 obatined in Example 17

400 MHz $^1$H NMR (CDCl₃) δ 7.24 (2H, m, Ar—H), 6.97 (2H, m, Ar—H), 4.19 (2H, d, J = 13.5 Hz, ArCH₂N), 3.88 (6H, s, OCH₃), 3.80 (2H, d, J = 13.6 Hz, ArCH₂N), 2.93 (2H, m, NCH₂), 2.66 (2H, m, NCH₂), 2.13 (6H, s, CH₃), 2.12 (6H, s, CH₃), 1.15-1.00 (6H, m, CH₂), 0.81 (6H, t, J = 6.7 Hz, CH₃), 0.38 (2H, m, CH₂).

Example 18

Synthesis of Quaternary Ammonium Salt (Compound (R)-80)

mg, 0.2 mmol) in acetonitrile (5 mL) under a nitrogen atmosphere. This reaction mixture was heated at 80° C. for ten hours. Then, this was poured into water and the mixture was extracted with ethyl acetate. The organic layer was dried over Na₂SO₄ and concentrated under reduced pressure. The residue was purified by silica gel column chromatography (methanol/toluene=1/5 as eluent) to give the title optically active quaternary ammonium bromide (compound (R)-80) (R-form) (200 mg, 0.164 mmol/yield: 82%). The NMR spectrum of the obtained compound (R)-80 is shown in Table 47.

TABLE 47

NMR spectrum of compound (R)-80 obtained in Example 18

400 MHz $^1$H NMR (CDCl₃) δ 7.26 (2H, s, Ar—H), 7.00 (2H, s, Ar—H), 4.30 (2H, d, J = 13.4 Hz, ArCH₂N), 4.03 (6H, s, OCH₃), 3.93 (6H, s, OCH₃), 3.87 (2H, d, J = 13.4 Hz, ArCH₂N), 3.75 (6H, s, OCH₃), 2.84 (4H, m, NCH₂), 1.30-1.03 (62H, m, CH₂), 0.88 (6H, t, J = 7.0 Hz, CH₃), 0.23 (2H, m, CH₂).

Example 19

Synthesis of Quaternary Ammonium Salt (Compound (R,R)-82)

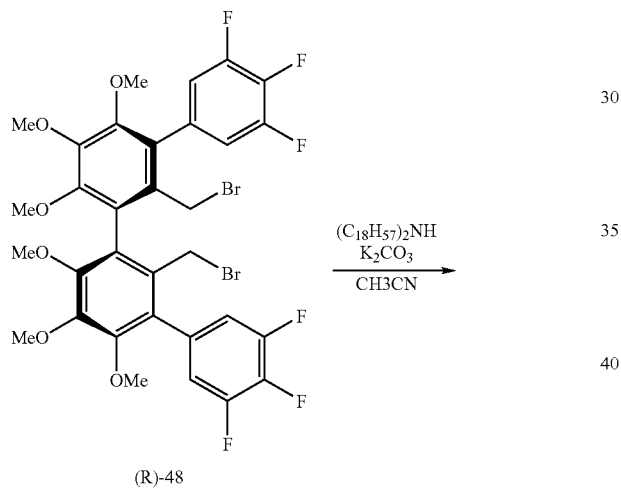

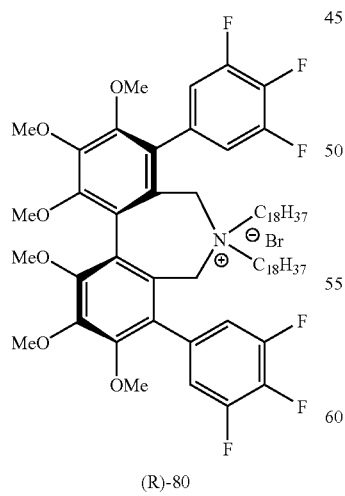

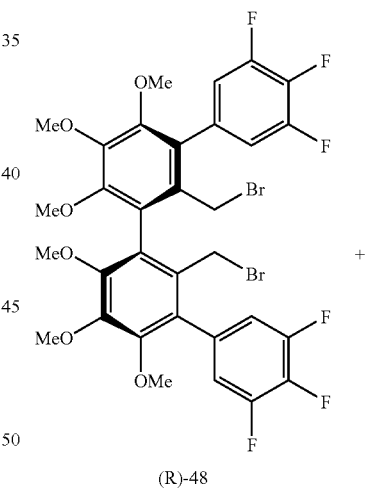

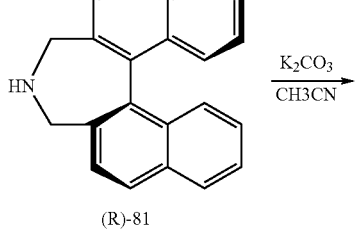

Dioctadecylamine (104 ng, 0.2 mmol) was added to a suspension of potassium carbonate (55 mg, 0.4 mmol) and the compound (R)-48 obtained in Reference Example 15 (156

147

-continued

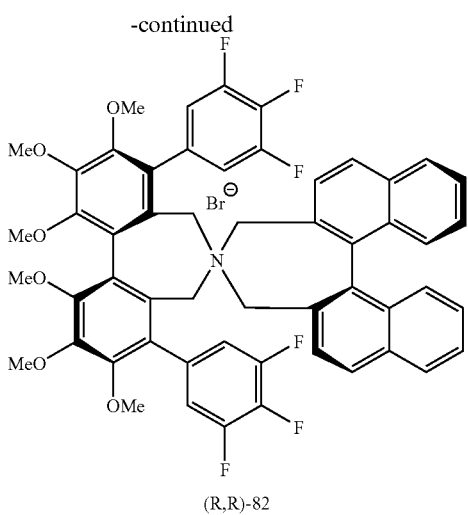

(R,R)-82

To a suspension of potassium carbonate (207 mg, 1.5 mmol) and the compound (R)-48 obtained in Reference Example 15 (390 mg, 0.5 mmol) in acetonitrile (20 mL), (R)-3,5-dihydro-4H-dinaphth[2,1-c:1'2'-e]azepine (compound (R)-81) (148 mg, 0.5 mmol) was added under a nitrogen atmosphere. This reaction mixture was heated at 80° C. for two hours. Then, this was poured into water and then the mixture was extracted with ethyl acetate. The organic layer was dried over $Na_2SO_4$ and concentrated under reduced pressure. The residue was purified by silica gel column chromatography (methanol/toluene=1/4 as eluent) to give the title optically active quaternary ammonium bromide (compound (R,R)-82) (R,R-form) (0.48 g, 0.48 mmol/yield: 96%) The NMR spectrum of the obtained compound (R,R)-82 is shown in Table 48.

TABLE 48

NMR spectrum of compound (R,R)-82 obtained in Example 19

400 MHz $^1$H NMR (CDCl$_3$) δ 7.92 (2H, d, J = 8.2 Hz, Ar—H), 7.56-7.49 (4H, m, Ar—H), 7.27-7.10 (6H, m, Ar—H), 6.79 (2H, m, Ar—H), 6.46 (2H, d, J = 8.4 Hz, Ar—H), 4.63 (2H, d, J = 13.7 Hz, ArCH$_2$N), 4.41 (4H, t, J = 14.0 Hz, ArCH$_2$N), 4.10 (6H, s, OCH$_3$), 3.90 (6H, s, OCH$_3$), 3.75 (6H, s, OCH$_3$), 3.60 (2H, d, J = 13.0 Hz, ArCH$_2$N).

Example 20

Confirmation of α-benzylation of Glycine (90)

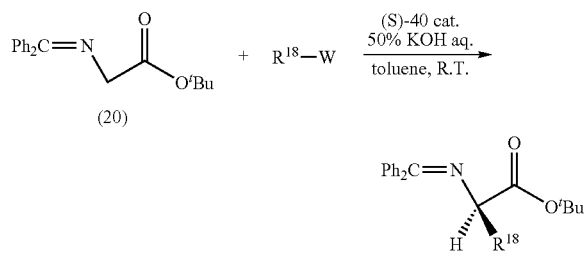

A mixture of the compound (S)-40 obtained in Example 13 (1 mol %; phase-transfer catalyst) and benzyl bromide (1.5 equivalents, 36 μL, 0.3 mmol) as the compound represented by $R^{18}$—W in the above formula was added to a mixture of 50% KOH aqueous solution (1 mL) and a toluene solution (1.5 mL) of N-(biphenylmethylene)glycine tert-butyl ester (compound 20) (59.1 mg, 0.2 mmol), and this was stirred vigorously at room temperature under an argon atmosphere. Completion of the reaction was confirmed by TLC, and then the reaction mixture was poured into water and the mixture was extracted with ether. The organic extract was washed with saline and dried over $Na_2SO_4$. The solvent was evaporated under reduced pressure, and then the residual oil was purified by silica gel column chromatography (ether/hexane=1/10 as eluent) to give the corresponding compound 21 ((R)-tert-butyl N-(diphenylmethylene)phenylalanine) (75.6 mg, 0.196 mmol/yield: 98%). The optical purity of the compound 21 obtained in this example was analyzed by HPLC [Daicel Chiralcel OD; eluent: hexane/2-propanol=100/1, flow rate 0.5 mL/min; retention time: (R)-form=14.8 min, (S)-form=28.2 min]. The optical purity of the compound 21 obtained in this example was 96% ee.

Example 21

Confirmation of α-Benzylation of Glycine (91)

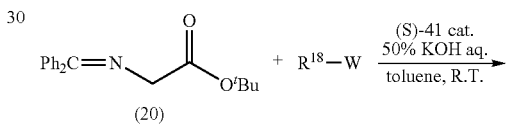

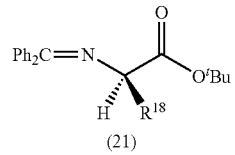

(21)

A mixture of the compound (S)-41 obtained in Example 14 (1 mol %; phase-transfer catalyst) and benzyl bromide (1.5 equivalents, 36 μL, 0.3 mmol) as the compound represented by $R^{18}$—W in the above formula was added to a mixture of 50% KOH aqueous solution (1 mL) and a toluene solution (1.5 mL) of N-(biphenylmethylene)glycine tert-butyl ester (compound 20) (59.1 mg, 0.2 mmol), and this was stirred vigorously at room temperature under an argon atmosphere. Completion of the reaction was confirmed by TLC, and then the reaction mixture was poured into water and the mixture was extracted with ether. The organic extract was washed with saline and dried over $Na_2SO_4$. The solvent was evaporated under reduced pressure, and then the residual oil was purified by silica gel column chromatography (ether/hexane=1/10 as eluent) to give the corresponding compound 21 ((R)-tert-butyl N-(diphenylmethylene)phenylalanine) (76.3 mg, 0.198 mmol/yield: 99%). The optical purity of the compound 21 obtained in this example was analyzed by HPLC [Daicel Chiralcel OD; eluent: hexane/2-propanol=100/1, flow rate 0.5 mL/min; retention time: (R)-form=14.8 min, (S)-form=28.2 min]. The optical purity of the compound 21 obtained in this example was 96% ee.

Example 22

Confirmation of α-Benzylation of Glycine (92)

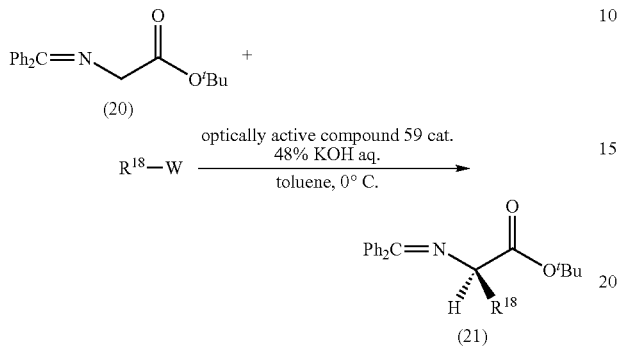

A mixture of the optically active compound 59 obtained in Example 15 (0.06 mol %; phase-transfer catalyst) and benzyl bromide (1.06 equivalents, 250 μL, 2.1 mmol) as the compound represented by $R^{18}$—W in the above formula was added to a mixture of 48% KOH aqueous solution (6.7 mL) and a toluene solution (6.7 mL) of N-(biphenylmethylene) glycine tert-butyl ester (590 mg, 2 mmol), and this was stirred vigorously at 0° C. Completion of the reaction was confirmed by TLC, and then the reaction mixture was poured into water and the mixture was extracted with ethyl acetate. The organic extract was washed with saline and dried over $Na_2SO_4$. The solvent was evaporated under reduced pressure to give (R)-tert-butyl N-(diphenylmethylene) phenylalanine (0.72 g, 1.86 mmol/yield: 93%). The optical purity of the obtained (R)-tert-butyl N-(diphenylmethylene)phenylalanine was analyzed by HPLC [Daicel Chiralcel OD-H; eluent: hexane/2-propanol=100/1, flow rate 1 mL/min; retention time: (R)-form=9.2 min, (S)-form=15.6 min]. The optical purity of the compound 21 obtained in this example was 97% ee.

Example 23

Confirmation of α-Benzylation of Glycine (93)

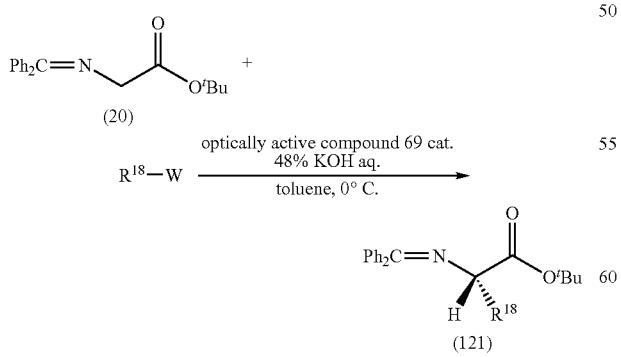

A mixture of the optically active compound 69 obtained in Example 16 (0.05 mol %; phase-transfer catalyst) and benzyl bromide (1.05 equivalents, 250 μL, 2.1 mmol) as the compound represented by $R^{18}$—W in the above formula was added to a mixture of 48% KOH aqueous solution (6.7 mL) and a toluene solution (6.7 mL) of N-(biphenylmethylene) glycine tert-butyl ester (590 mg, 2 mmol), and this was stirred vigorously at 0° C. Completion of the reaction was confirmed by TLC, and then the reaction mixture was poured into water and the mixture was extracted with ethyl acetate. The organic extract was washed with saline and dried over $Na_2SO_4$. The solvent was evaporated under reduced pressure to give (R)-tert-butyl N-(diphenylmethylene) phenylalanine (0.81 g, 1.67 mmol/yield: 84%). The optical purity of the (S)-tert-butyl N-(diphenylmethylene)phenylalanine thus obtained was analyzed by HPLC [Daicel Chiralcel OD-H; eluent: hexane/2-propanol=100/1, flow rate 1 mL/min; retention time: (R)-form=9.2 min, (S)-form=15.6 min]. The optical purity of the compound 121 obtained in this example was 90% ee.

Example 24

Confirmation of α-Benzylation of Glycine (94)

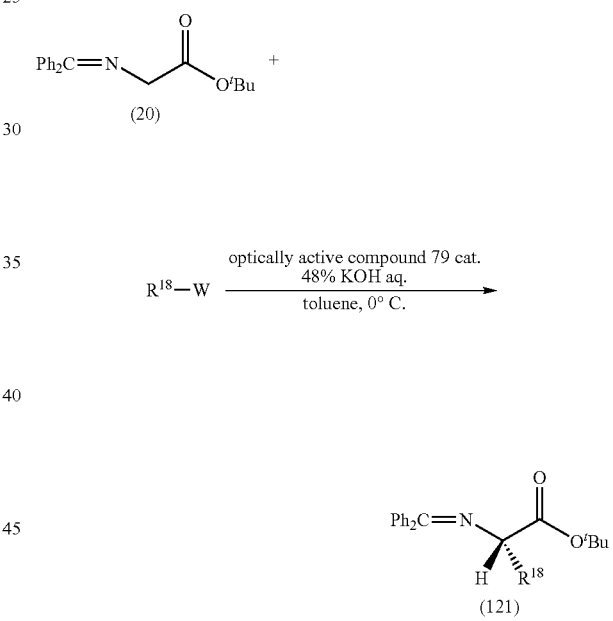

A mixture of the optically active compound 79 obtained in Example 17 (0.06 mol %; phase-transfer catalyst) and benzyl bromide (1.05 equivalents, 250 μL, 2.1 mmol) as the compound represented by $R^{18}$—W in the above formula was added to a mixture of 48% KOH aqueous solution (6.7 mL) and a toluene solution (6.7 mL) of N-(biphenylmethylene) glycine tert-butyl ester (590 mg, 2 mmol), and this was stirred vigorously at 0° C. Completion of the reaction was confirmed by TLC, and then the reaction mixture was poured into water and the mixture was extracted with ethyl acetate. The organic extract was washed with saline and dried over $Na_2SO_4$. The solvent was evaporated under reduced pressure to give (S)-tert-butyl N-(diphenylmethylene) phenylalanine (0.76 g, 1.72 mmol/yield: 86%). The optical purity of the obtained (S)-tert-butyl N-(diphenylmethylene)phenylalanine was analyzed by HPLC [Daicel Chiralcel OD-H; eluent: hexane/2-propanol=100/1, flow rate 1 mL/min; retention time: (R)- form=9.2 min, (S)-form=15.6 min]. The optical purity of the compound 121 obtained in this example was 97% ee.

Example 25

Confirmation of α-Benzylation of Glycine (95)

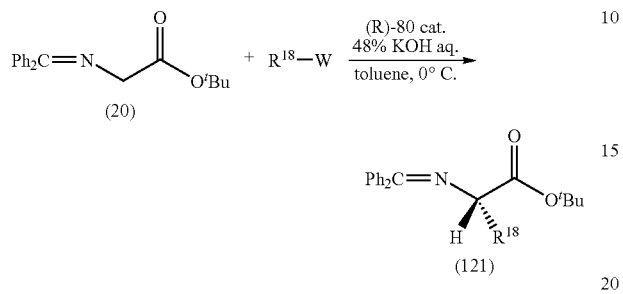

A mixture of the compound (R)-80 obtained in Example 18 (0.05 mol %; phase-transfer catalyst) and benzyl bromide (1.05 equivalents, 250 μL, 2.1 mmol) as the compound represented by $R^{18}$—W in the above formula was added to a mixture of 48% KOH aqueous solution (6.7 mL) and a toluene solution (6.7 mL) of N-(biphenylmethylene)glycine tert-butyl ester (590 mg, 2 mmol), and this was stirred vigorously at 0° C. Completion of the reaction was confirmed by TLC, and then the reaction mixture was poured into water and the mixture was extracted with ethyl acetate. The organic extract was washed with saline and dried over $Na_2SO_4$. The solvent was evaporated under reduced pressure to give (S)-tert-butyl N-(diphenylmethylene) phenylalanine (0.75 g, 1.82 mmol/yield: 91%). The optical purity of the obtained (S)-tert-butyl N-(diphenylmethylene)phenylalanine was analyzed by HPLC [Daicel Chiralcel OD-H; eluent: hexane/2-propanol=100/1, flow rate 1 mL/min; retention time: (R)-form=9.2 min, (S)-form=15.6 min]. The optical purity of the compound 121 obtained in this example was 96% ee.

Example 26

Confirmation of α-Benzylation of Glycine (96)

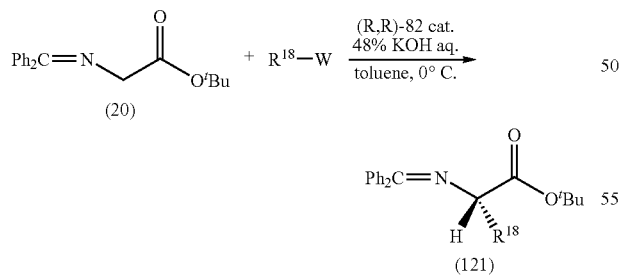

A mixture of the compound (R,R)-82 obtained in Example 19 (0.5 mol %; phase-transfer catalyst) and benzyl bromide (1.05 equivalents, 250 μL, 2.1 mmol) as the compound represented by $R^{18}$—W in the above formula was added to a mixture of 48% KOH aqueous solution (6.7 mL) and a toluene solution (6.7 mL) of N-(biphenylmethylene) glycine tert-butyl ester (590 mg, 2 mmol), and this was stirred vigorously at 0° C. Completion of the reaction was confirmed by TLC, and then the reaction mixture was poured into water and the mixture was extracted with ethyl acetate. The organic extract was washed with saline and dried over $Na_2SO_4$. The solvent was evaporated under reduced pressure to give (S)-tert-butyl N-(diphenylmethylene)phenylalanine (0.87 g, 2.0 mmol) in a quantitative yield. The optical purity of the obtained (S)-tert-butyl N-(diphenylmethylene)phenylalanine was analyzed by HPLC [Daicel Chiralcel OD-H; eluent: hexane/2-propanol=100/1, flow rate 1 mL/min; retention time: (R)-form=9.2 min, (S)-form=15.6 min]. The optical purity of the compound 121 obtained in this example was 96% ee.

Reference Example 43

Synthesis of Starting Material (Compound 109a) for Synthesizing Quaternary Ammonium Salt

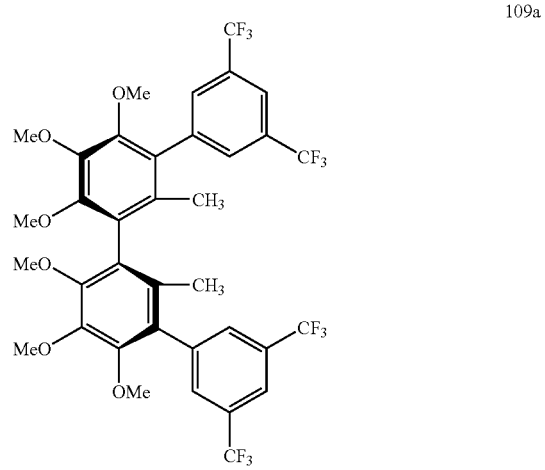

A mixture of the compound 8a obtained in Reference Example 5 (0.26 g, 0.5 mmol), 3,5-bis(trifluoromethyl)boronic acid (0.516 g, 2.0 mmol), palladium acetate (0.0225 g, 0.10 mmol), tri-o-tolylphosphine (0.122 g, 0.40 mmol), potassium phosphate n-hydrate (1.27 g, 6.0 mmol), and THF (7 mL) was stirred with heating at 75° C. under an argon atmosphere. The disappearance of the starting material was confirmed by TLC, and then the suspension was filtered through alumina and $Na_2SO_4$. The pad was washed with ethyl acetate, and then the organic layer was washed with 1 N hydrochloric acid. The organic layer was then concentrated under reduced pressure. The residue was purified by silica gel column chromatography (hexane/ethyl acetate=10/1 and 5/1 as eluent) to give the title compound 109a ((S)-3,3'-bis(3,5-bis (trifluoromethyl)phenyl)-4,5,6,4',5',6'-hexamethoxybiphenyl-2,2'-dimethane) (0.294 g, 0.37 mmol/yield: 75%). The NMR spectrum of the obtained compound 109a is shown in Table 49.

TABLE 49

NMR spectrum of compound 109a

400 MHz $^1$H NMR (CDCl$_3$) δ 7.87 (2H, s, Ar—H), 7.75 (4H, d, J = 20 Hz, Ar—H), 3.95 (6H, s, OMe), 3.80 (6H, s, OMe), 3.71 (6H, s, OMe), 1.71 (6H, s, CH$_3$)

Reference Example 44

Synthesis of Starting Material (Compound 110a) for Synthesizing Quaternary Ammonium Salt

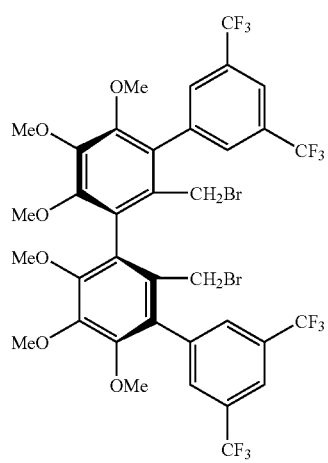

110a

A solution of the compound 109a obtained in Reference Example 43 (0.079 g, 0.1 mmol), N-bromosuccinimide (0.04 g, 0.22 mmol), and 2,2'-azobisisobutyronitrile (AIBN; 0.0033 g, 0.02 mmol) in benzene (5 mL) was heated under reflux for four hours. A saturated aqueous Na$_2$SO$_3$ solution was added thereto to quench the reaction, and the mixture was extracted with ether. The organic layer was dried over Na$_2$SO$_4$, and was concentrated under reduced pressure. The residue was purified by silica gel column chromatography (hexane/ethyl acetate=5/1 as eluent) to give the title compound 110a ((S)-3,3'-bis(3,5-bis(trifluoromethyl)phenyl)-4,5,6,4',5',6'-hexamethoxybiphenyl-2,2'-dimethyl bromide) (0.094 g, 0.1 mmol) in a quantitative yield. The NMR spectrum of the obtained compound 110a is shown in Table 50.

TABLE 50

NMR spectrum of compound 110a

400 MHz $^1$H NMR (CDCl$_3$) δ 7.95 (4H, d, J = 13 Hz, Ar—H), 7.87 (2H, s, Ar—H), 3.98 (6H, s, OMe), 3.80-3.95 (10H, m, OMe + CH$_2$Br), 3.73 (6H, s, OMe)

Example 27

Synthesis of Quaternary Ammonium Salt ((S)-111)

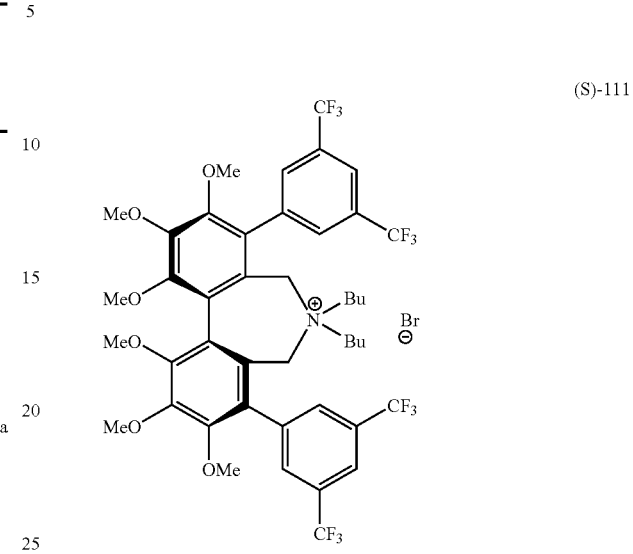

(S)-111

Dibutylamine (0.025 mL, 0.15 mmol) was added to a suspension of the compound 110a obtained in Reference Example 44 (0.094 g, 0.10 mmol) and potassium carbonate (0.0166 g, 0.12 mmol) in acetonitrile (10 mL) under an argon atmosphere. This reaction mixture was heated at 80° C. for 10 hours. Then, this was poured into a 1 N HBr aqueous solution and the mixture was extracted with CH$_2$Cl$_2$. The organic layer was dried over Na$_2$SO$_4$ and concentrated under reduced pressure. The residue was purified by silica gel column chromatography (methanol/CH$_2$Cl$_2$=1/20 and 1/10 as eluent) to give the title optically active quaternary ammonium bromide (compound (S)-111) (S-form) (0.088 g, 0.088 mmol/yield: 88%).

Reference Example 45

Synthesis of Starting Material (Compound (S)-108) for Synthesizing Quaternary Ammonium Salt

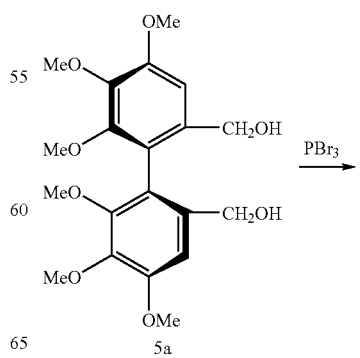

5a

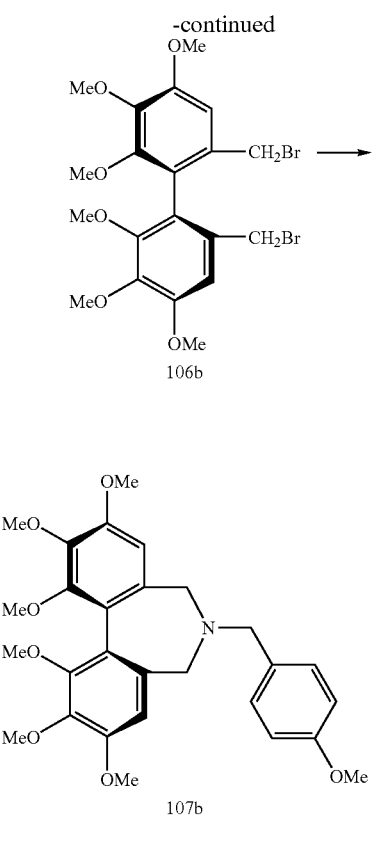

106b

107b (S)-108

Phosphorus tribromide (0.095 mL, 1.0 mmol) was added to a solution of compound 5a obtained in Reference Example 3 (0.131 g, 0.33 mmol) in CH$_2$Cl$_2$ (5 mL) at 0° C. The reaction mixture was stirred at room temperature for five hours. Then, the reaction was quenched with water and the mixture was extracted with hexane/ethyl acetate (1/1). This was dried over Na$_2$SO$_4$ and concentrated under reduced pressure to give the crude compound 106b.

Then, the entire quantity of the crude compound 106b obtained above and p-methoxybenzylamine were dissolved in THF and the solution was stirred overnight. After the disappearance of 106b was confirmed, the mixture was concentrated to give the crude 107b (0.161 g, 0.325 mmol, yield: 98%).

To a solution of the entire quantity of the crude 107b obtained above in MeOH (5 mL), was added 10% Pd/C (30 mg), and stirred under a hydrogen atmosphere overnight. After filtration through Celite, the filtrate was concentrated, and the residue was purified by silica gel column chromatography (methanol/CH$_2$Cl$_2$=1/1 as eluent) to give the title optically active secondary amine (S)-108 (S-form) (0.118 g, 0.31 mmol/yield: 95%).

Example 28

Synthesis of Quaternary Ammonium Salt ((S,S)-112)

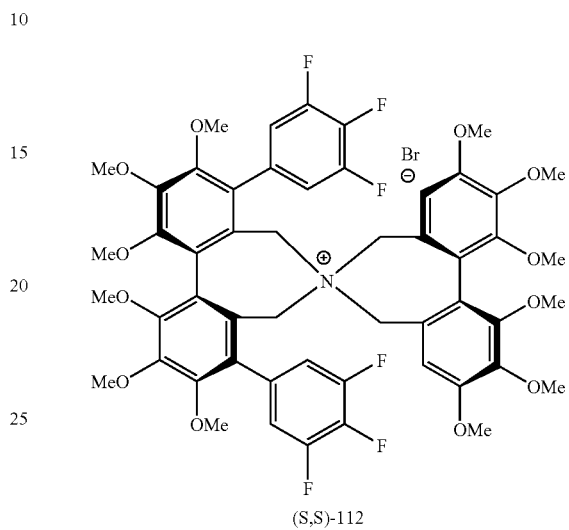

(S,S)-112

Phosphorus tribromide (0.038 mL, 0.4 mmol) was added to a solution of compound 5b obtained in Reference Example 9 (0.131 g, 0.2 mmol) in CH$_2$Cl$_2$ (5 mL) at 0° C. The reaction mixture was stirred at room temperature for one hour. Then, the reaction was quenched with water and the mixture was extracted with ether. The organic layer was washed with saline, dried over Na$_2$SO$_4$ and concentrated under reduced pressure to give the crude compound 6b quantitatively.

Then, part of the crude compound 6b (0.0245 g, 0.031 mmol) was transferred to a suspension of potassium carbonate (0.069 g, 0.5 mmol) and the secondary amine (S)-108 obtained in Reference Example 45 (0.014 g, 0.038 mmol) in acetonitrile (2 mL) under an argon atmosphere. Then, this mixture was heated at 40° C. for 10 hours. The reaction mixture was then poured into 1 N HBr to quench the reaction. The mixture was extracted with CH$_2$Cl$_2$. The organic layer was dried over Na$_2$SO$_4$ and concentrated under reduced pressure. The residue was purified by silica gel column chromatography (methanol/CH$_2$Cl$_2$=1/10 as eluent) to give the title optically active quaternary ammonium bromide (compound (S,S)-112) (S,S-form) (0.029 g, 0.027 mmol/yield: 87%). The mass spectrum of the obtained compound 112 was as follows: M$^+$=994.46.

Example 29

Confirmation of α-Benzylation of Glycine (211)

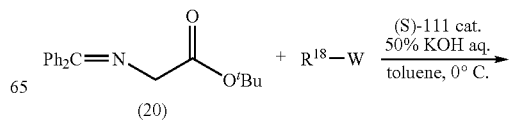

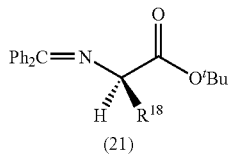

(21)

A mixture of the compound (S)-111 obtained in Example 27 (1 mol %; phase-transfer catalyst) and benzyl bromide (1.5 equivalents, 36 µL, 0.3 mmol) as the compound represented by $R^{18}$—W in the above formula was added to a mixture of 50% KOH aqueous solution (1 mL) and a toluene solution (1.5 mL) of N-(biphenylmethylene)glycine tert-butyl ester (compound 20) (59.1 mg, 0.2 mmol), and the mixture was stirred vigorously at 0° C. under an argon atmosphere. Completion of the reaction was confirmed by TLC, and then the reaction mixture was poured into water and the mixture was extracted with ether. The organic extract was washed with saline and dried over $Na_2SO_4$. The solvent was evaporated under reduced pressure, and then the residual oil was purified by silica gel column chromatography (ether/hexane=1/10 as eluent) to give the corresponding compound 21 ((R)-tert-butyl N-(diphenylmethylene) phenylalanine) (68.6 mg, 0.178 mmol/yield: 89%). The optical purity of the compound 21 obtained in this example was analyzed by HPLC [Daicel Chiralcel OD; eluent: hexane/2-propanol=100/1, flow rate 0.5 mL/min; retention time: (R)-form=14.8 min, (S)-form=28.2 min]. The optical purity of the compound 21 obtained in this example was 95% ee.

Example 30

Confirmation of α-Benzylation of Glycine (212)

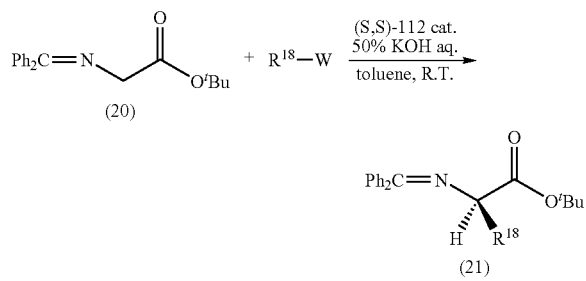

A mixture of the compound (S,S)-112 obtained in Example 28 (1 mol %; phase-transfer catalyst) and benzyl bromide (1.5 equivalents, 36 µL, 0.3 mmol) as the compound represented by $R^{18}$—W in the above formula was added to a mixture of 50% KOH aqueous solution (1 mL) and a toluene solution (1.5 mL) of N-(biphenylmethylene)glycine tert-butyl ester (compound 20) (59.1 mg, 0.2 mmol), and the mixture was stirred vigorously at room temperature under an argon atmosphere. Completion of the reaction was confirmed by TLC, and then the reaction mixture was poured into water and the mixture was extracted with ether. The organic extract was washed with saline and dried over $Na_2SO_4$. The solvent was evaporated under reduced pressure, and then the residual oil was purified by silica gel column chromatography (ether/hexane=1/10 as eluent) to give the corresponding compound 21 ((R)-tert-butyl N-(diphenylmethylene)phenylalanine) (72.5 mg, 0.188 mmol/yield: 94%). The optical purity of the compound 21 obtained in this example was analyzed by HPLC [Daicel Chiralcel OD; eluent: hexane/2-propanol=100/1, flow rate 0.5 mL/min; retention time: (R)-form=14.8 min, (S)-form=28.2 min]. The optical purity of the compound 21 obtained in this example was 77% ee.

Example 31

Confirmation of α-Benzylation of Glycine (31)

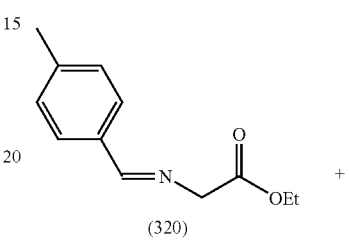

(320)

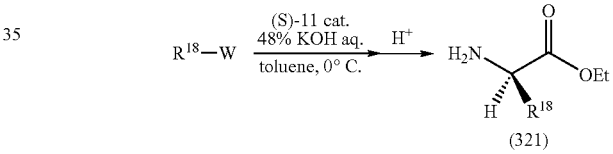

(321)

To a mixture of the compound (S)-11 obtained in Example 2 (0.1 mol %; phase-transfer catalyst), benzyl bromide (1.37 equivalents, 1.63 mL, 13.7 mmol) as the compound represented by $R^{18}$—W in the above formula, and a toluene solution (10 mL) of N-(4-methylphenylmethylene) glycine ethyl ester (2.05 g, 10 mmol), 48% KOH aqueous solution (2.3 g) was added, and the mixture was stirred vigorously at 0° C. Completion of the reaction was confirmed by TLC, and then the reaction mixture was poured into water and the mixture was extracted with ethyl acetate. The organic extract was washed with saline and dried over $Na_2SO_4$. The solvent was evaporated under reduced pressure, and then 1 N hydrochloric acid (20 mL) was added and the mixture was stirred at room temperature for one hour. The aqueous mixture was washed with toluene (20 mL×3). Sodium bicarbonate was added carefully to avoid too vigorous bubbling until pH of the solution reached not lower than 11 (confirmed with universal pH test paper). The mixture was extracted with ethyl acetate (20 mL×3). The ethyl acetate solution obtained was dried over sodium sulfate and concentrated under reduced pressure to give the title compound 321 ((R)-phenylalanine ethyl ester) (1.18 g, 6.11 mmol/yield: 61%). The optical purity of the obtained (R)-phenylalanine ethyl ester was analyzed by HPLC [Daicel Chiralcel OD-H; eluent: hexane/2-propanol/diethylamine=98/2/0.1, flow rate 0.5 mL/min; retention time:

(R)-form=23.2 min, (S)-form=24.9 min]. The optical purity of the compound 321 obtained in this example was 77% ee.

Example 32

Confirmation of α-Benzylation of Glycine (31)

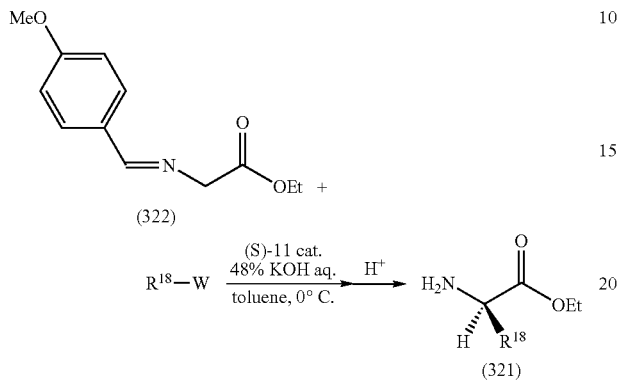

To a mixture of the compound (S)-11 obtained in Example 2 (0.1 mol %; phase-transfer catalyst), benzyl bromide (1.37 equivalents, 1.63 mL, 13.7 mmol) as the compound represented by $R^{18}$—W in the above formula, and a toluene solution (10 mL) of N-(4-methylphenylmethylene)glycine ethyl ester (2.05 g, 10 mmol), 48% KOH aqueous solution (2.3 g) was added, and the mixture was stirred vigorously at 0° C. Completion of the reaction was confirmed by TLC, and then the reaction mixture was poured into water and the mixture extracted with ethyl acetate. The organic extract was washed with saline and dried over $Na_2SO_4$. The solvent was evaporated under reduced pressure, and then 1 N hydrochloric acid (20 mL) was added thereto and the mixture was stirred at room temperature for one hour. The aqueous layer was washed with toluene (20 mL×3), and sodium bicarbonate was added carefully to avoid too vigorous bubbling until pH of the solution reached not lower than 11 (confirmed with universal pH test paper). The mixture was extracted with ethyl acetate (20 mL×3). The obtained ethyl acetate solution was dried over sodium sulfate and concentrated under reduced pressure to give the title compound 321 ((R)-phenylalanine ethyl ester) (1.32 g, 6.83 mmol/yield: 68%). The optical purity of the obtained (R)-phenylalanine ethyl ester was analyzed by HPLC [Daicel Chiralcel OD-H; eluent: hexane/2-propanol/diethylamine=98/2/0.1, flow rate 0.5 mL/min; retention time: (R)-form=23.2 min, (S)-form=24.9 min]. The optical purity of the compound 321 obtained in this example was 74% ee.

INDUSTRIAL APPLICABILITY

According to the present invention, a chiral phase-transfer catalyst having a simpler structure is provided. This phase-transfer catalyst can be produced by a fewer number of process steps than conventional ones, which leads to reduction in the production cost. Such a phase-transfer catalyst is extremely useful in the synthesis of α-alkyl-α-amino acids and derivatives thereof, and α,α-dialkyl-α-amino acids and derivatives thereof. The amino acids and their derivatives thus synthesized play an important and special role in the design of peptides having enhanced activity (pharmacological or physiological activity, for example), as effective enzyme inhibitors, and as chiral building blocks for the synthesis of compounds having various biological activities. Therefore, they are useful for the development of novel foods and pharmaceuticals.

The invention claimed is:
1. A compound represented by the following formula (I):

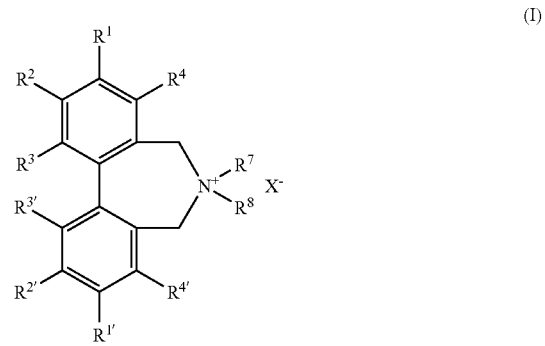

wherein
$R^1$ and $R^{1'}$ are each independently:
  a hydrogen atom;
  a $C_1$ to $C_5$ alkyl group that may be substituted with an aryl group, and/or that may be branched or form a cyclic group if a $C_3$ to $C_5$ alkyl group; or
  a $C_1$ to $C_5$ alkoxy group that may be substituted with an aryl group, and/or that may be branched or form a cyclic group if a $C_3$ to $C_5$ alkoxy group;
$R^2$ and $R^{2'}$ are each independently:
  a hydrogen atom; or
  a $C_1$ to $C_5$ alkoxy group that may be substituted with an aryl group, and/or that may be branched or form a cyclic group if a $C_3$ to $C_5$ alkoxy group;
$R^3$ and $R^{3'}$ are each independently:
  a $C_1$ to $C_5$ alkyl group that may be substituted with an aryl group, and/or that may be branched or form a cyclic group if a $C_3$ to $C_5$ alkyl group; or
  a $C_1$ to $C_5$ alkoxy group that may be substituted with an aryl group, and/or that may be branched or form a cyclic group if a $C_3$ to $C_5$ alkoxy group;
$R^4$ and $R^{4'}$ are each independently:
  (xv) an aryl group selected from the group consisting of phenyl, naphthyl, anthracenyl and phenanthryl, and which is optionally substituted with at least one group selected from the group consisting of:
    a $C_1$ to $C_4$ alkyl group that may be branched if a $C_3$ to $C_4$ alkyl group,
    a $C_1$ to $C_5$ alkoxy group that may be branched if a $C_3$ to $C_5$ alkoxy group,
    an aryl group that may be substituted with, a $C_1$ to $C_4$ alkyl group that may be branched if a $C_3$ to $C_4$ alkyl group, a cyano group, —$NR^{30}R^{31}$ (where $R^{30}$ and $R^{31}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched if a $C_3$ to $C_4$ alkyl group),
    a cyano group,
    —$NR^{30}R^{31}$ (where $R^{30}$ and $R^{31}$ are each independently a hydrogen atom or a $C_1$ to $C_4$ alkyl group),
    a nitro group,
    a carbamoyl group,
    an N—($C_1$ to $C_4$ alkyl)carbamoyl group, an N,N-di($C_1$ to $C_4$ alkyl)carbamoyl group,
—NHCOR$^9$ (where R$^9$ is a $C_1$ to $C_4$ alkyl group that may be branched if a $C_3$ to $C_4$ alkyl group), and
a halogen atom;
or may be substituted with —O—(CH$_2$)$_p$—O— (where p is 1 or 2) at positions 3 and 4 that are taken together;
R$^7$ and R$^8$ are each independently:
(i) a $C_1$ to $C_{12}$ alkyl group that may be branched or form a cyclic group if a $C_3$ to $C_{12}$ alkyl group;
(x) —(CH$_2$)$_n$Y—OR$^{12}$ (where Y is a $C_1$ to $C_4$ divalent saturated hydrocarbon group that may be branched, and R$^{12}$ is a group selected from the group consisting of:
  (1) a hydrogen atom; and
  (2) a $C_1$ to $C_4$ alkyl group that may be branched if a $C_3$ to $C_4$ alkyl group;
and n is an integer from 1 to 12);
(xi) —(CH$_2$)$_n$—OR$^{12}$ (where R$^{12}$ is a group selected from the group consisting of:
  (1) a hydrogen atom; and
  (2) a $C_1$ to $C_4$ alkyl group that may be branched if a $C_3$ to $C_4$ alkyl group;
and n is an integer from 1 to 12); or
R$^7$ and R$^8$ are taken together to form a divalent group selected from the group consisting of:

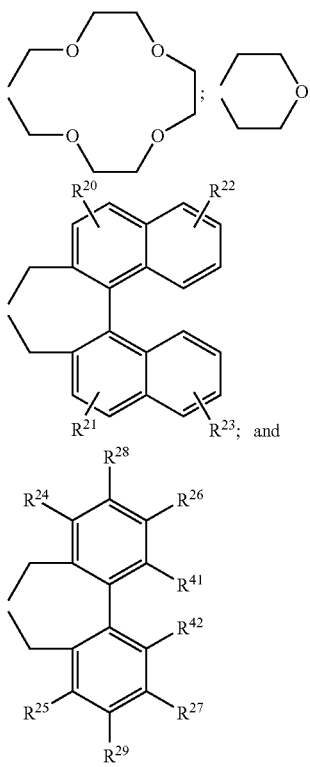

(wherein R$^{20}$, R$^{21}$, R$^{22}$, R$^{23}$, R$^{24}$, R$^{25}$, R$^{26}$, R$^{27}$, R$^{28}$, and R$^{29}$, are hydrogen atoms;
with the proviso that in the four combinations of four groups, that is, the combinations R$^{24}$, R$^{25}$, R$^4$ and R$^{4'}$, R$^{26}$, R$^{27}$, R$^2$ and R$^{2'}$, R$^{28}$, R$^{29}$, R$^1$ and R$^{1'}$, and, R$^3$ and R$^{3'}$, the four groups of at least one of the combinations are not identical); and
X$^-$ is an anion selected from the group consisting of a halide anion, SCN$^-$, HSO$_4^-$, and HF$_2$.

2. The compound of claim 1, wherein each of R$^1$, R$^{1'}$, R$^2$, R$^{2'}$, R$^3$, and R$^{3'}$ of the compound represented by the formula (I) is a $C_1$ to $C_5$ alkoxy group that may be branched or form a cyclic group if a $C_3$ to $C_5$ alkoxy group.

3. The compound of claim 1, wherein each of R$^1$, R$^{1'}$, R$^2$, R$^{2'}$, R$^3$, and R$^{3'}$ of the compound represented by the formula (I) is a methoxy group, an ethoxy group, or a benzyloxy group.

4. The compound of claim 1, wherein each of R$^4$ and R$^{4'}$ of the compound represented by the formula (I) is a 3,4,5-trifluorophenyl group.

5. The compound of claim 1, wherein R$^7$ and R$^8$ of the compound represented by the formula (I) are each independently a $C_1$ to $C_{12}$ alkyl group that may be branched or form a cyclic group if a $C_3$ to $C_{12}$ alkyl group.

6. The compound of claim 5, wherein R$^7$ and R$^8$ of the compound represented by the formula (I) are both an n-butyl group.

7. A method for producing the compound represented by the formula (I) of claim 1, comprising:
a step of reacting a compound represented by the following formula (II):

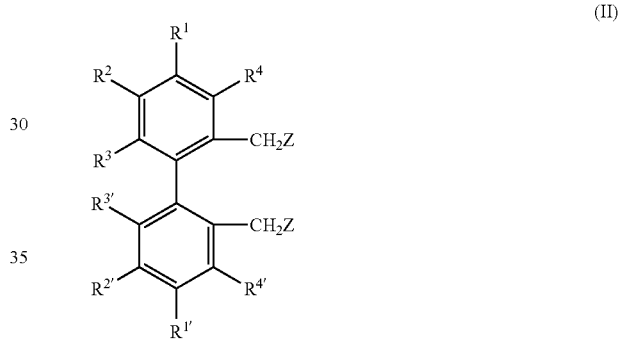

with a secondary amine represented by the following formula (III):

in an organic solvent in the presence of an acid scavenging agent;
wherein in the formula (II):
R$^1$ and R$^{1'}$ are each independently:
  a hydrogen atom;
  a $C_1$ to $C_5$ alkyl group that may be substituted with an aryl group, and/or that may be branched or form a cyclic group if a $C_3$ to $C_5$ alkyl group; or
  a $C_1$ to $C_5$ alkoxy group that may be substituted with an aryl group, and/or that may be branched or form a cyclic group if a $C_3$ to $C_5$ alkoxy group;
R$^2$ and R$^{2'}$ are each independently:
  a hydrogen atom; or
  a $C_1$ to $C_5$ alkoxy group that may be substituted with an aryl group, and/or that may be branched or form a cyclic group if a $C_3$ to $C_5$ alkoxy group;

$R^3$ and $R^{3'}$ are each independently:
- a $C_1$ to $C_5$ alkyl group that may be substituted with an aryl group, and/or that may be branched or form a cyclic group if a $C_3$ to $C_5$ alkyl group; or
- a $C_1$ to $C_5$ alkoxy group that may be substituted with an aryl group, and/or that may be branched or form a cyclic group if a $C_3$ to $C_5$ alkoxy group;

$R^4$ and $R^{4'}$ are each independently:
(xv) an aryl group selected from the group consisting of phenyl, naphthyl, anthracenyl and phenanthryl, and which is optionally substituted with at least one group selected from the group consisting of:
- a $C_1$ to $C_4$ alkyl group that may be branched if a $C_3$ to $C_4$ alkyl group,
- a $C_1$ to $C_5$ alkoxy group that may be branched if a $C_3$ to $C_5$ alkoxy group,
- an aryl group that may be substituted with, a $C_1$ to $C_4$ alkyl group that may be branched if a $C_3$ to $C_4$ alkyl group, a cyano group, —$NR^{30}R^{31}$ (where $R^{30}$ and $R^{31}$ are each independently a hydrogen atom or a $C_1$ to $C_4$ alkyl group), a nitro group, a carbamoyl group, an N—($C_1$ to $C_4$ alkyl)carbamoyl group, an N,N-di($C_1$ to $C_4$ alkyl)carbamoyl group, or —$NHCOR^9$ (where $R^9$ is a $C_1$ to $C_4$ alkyl group that may be branched if a $C_3$ to $C_4$ alkyl group),
- a cyano group,
- —$NR^{30}R^{31}$ (where $R^{30}$ and $R^{31}$ are each independently a hydrogen atom or a $C_1$ to $C_4$ alkyl group),
- a nitro group,
- a carbamoyl group,
- an N—($C_1$ to $C_4$ alkyl)carbamoyl group,
- an N,N-di($C_1$ to $C_4$ alkyl)carbamoyl group,
- —$NHCOR^9$ (where $R^9$ is a $C_1$ to $C_4$ alkyl group that may be branched if a $C_3$ to $C_4$ alkyl group), and
- a halogen atom;

or may be substituted with —O—$(CH_2)_p$—O— (where p is 1 or 2) at positions 3 and 4 that are taken together; and
Z is a halogen atom;
and in the formula (III):
$R^7$ and $R^8$ are each independently:
(i) a $C_1$ to $C_{12}$ alkyl group that may be branched or form a cyclic group if a $C_3$ to $C_{12}$ alkyl group;
(x) —$(CH_2)_n$Y—$OR^{12}$ (where Y is a $C_1$ to $C_4$ divalent saturated hydrocarbon group that may be branched, and $R^{12}$ is a group selected from the group consisting of:
(1) a hydrogen atom; and
(2) a $C_1$ to $C_4$ alkyl group that may be branched if a $C_3$ to $C_4$ alkyl group;
and n is an integer from 1 to 12);
(xi) —$(CH_2)_n$—$OR^{12}$ (where $R^{12}$ is a group selected from the group consisting of:
(1) a hydrogen atom; and
(2) a $C_1$ to $C_4$ alkyl group that may be branched if a $C_3$ to $C_4$ alkyl group;
and n is an integer from 1 to 12); or
$R^7$ and $R^8$ are taken together to form a divalent group selected from the group consisting of:

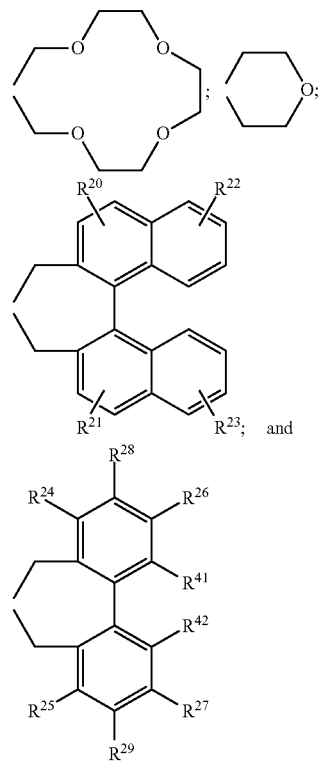

(wherein $R^{20}$, $R^{21}$, $R^{22}$, $R^{23}$, $R^{24}$, $R^{25}$, $R^{26}$, $R^{27}$, $R^{28}$, and $R^{29}$, are hydrogen atoms;
with the proviso that in the four combinations of four groups, that is, the combinations $R^{24}$, $R^{25}$, $R^4$ and $R^{4'}$, $R^{26}$, $R^{27}$, $R^2$ and $R^{2'}$, $R^{28}$, $R^{29}$, $R^1$ and $R^{1'}$, and, $R^3$ and $R^{3'}$, the four groups of at least one of the combinations are not identical).

8. The method of claim 7, wherein each of $R^1$, $R^{1'}$, $R^2$, $R^{2'}$, $R^3$, and $R^{3'}$ of the compound represented by the formula (II) is a $C_1$ to $C_5$ alkoxy group that may be branched or form a cyclic group if a $C_3$ to $C_5$ alkoxy group.

9. The method of claim 7, wherein each of $R^1$, $R^{1'}$, $R^2$, $R^{2'}$, $R^3$, and $R^{3'}$ of the compound represented by the formula (II) is a methoxy group, an ethoxy group, or a benzyloxy group.

10. The method of claim 7, wherein each of $R^4$ and $R^{4'}$ of the compound represented by the formula (II) is a 3,4,5-trifluorophenyl group.

11. The method of claim 7, wherein $R^7$ and $R^8$ of the compound represented by the formula (III) are each independently a $C_1$ to $C_{12}$ alkyl group that may be branched or form a cyclic group if a $C_3$ to $C_{12}$ alkyl group.

12. The method of claim 11, wherein $R^7$ and $R^8$ of the compound represented by the formula (III) are both an n-butyl group.

* * * * *

UNITED STATES PATENT AND TRADEMARK OFFICE
CERTIFICATE OF CORRECTION

PATENT NO. : 8,614,316 B2  
APPLICATION NO. : 11/910364  
DATED : December 24, 2013  
INVENTOR(S) : Keiji Maruoka et al.

Page 1 of 1

It is certified that error appears in the above-identified patent and that said Letters Patent is hereby corrected as shown below:

In the Claims

Column 161, Claim 1, line 67, "$HF_2$" should read --$HF_2^-$--.

Signed and Sealed this
Twenty-second Day of April, 2014

Michelle K. Lee
*Deputy Director of the United States Patent and Trademark Office*